(12) United States Patent
Xia

(10) Patent No.: US 12,268,834 B2
(45) Date of Patent: Apr. 8, 2025

(54) INTRODUCTION NEEDLE AND TATTOO DEVICE

(71) Applicant: Tingting Xia, Jiangsu (CN)

(72) Inventor: Tingting Xia, Jiangsu (CN)

( * ) Notice: Subject to any disclaimer, the term of this patent is extended or adjusted under 35 U.S.C. 154(b) by 0 days.

(21) Appl. No.: 18/651,482

(22) Filed: Apr. 30, 2024

(65) Prior Publication Data

US 2024/0299720 A1    Sep. 12, 2024

Related U.S. Application Data

(63) Continuation of application No. PCT/CN2023/128493, filed on Oct. 31, 2023, and a continuation-in-part of application No. 18/243,097, filed on Sep. 6, 2023, now Pat. No. 11,998,714, which is a continuation of application No. PCT/CN2022/071557, filed on Jan. 12, 2022, application No. 18/651,482 is a continuation-in-part of application No. 18/243,091, filed on Sep. 6, 2023, now Pat. No. 11,998,713, which is a continuation of application No. PCT/CN2022/071556, filed on Jan. 12, 2022, application No. 18/651,482 is a continuation of application No. PCT/CN2023/108804, filed on Jul. 24, 2023, and a continuation of application No. PCT/CN2023/102338, filed on Jun. 26, 2023, and a continuation of application No. PCT/CN2023/102336, filed on Jun. 26, 2023.

(30) Foreign Application Priority Data

| Apr. 14, 2021 | (CN) | .......................... 202110402463.0 |
| Apr. 14, 2021 | (CN) | .......................... 202110402475.3 |
| Jul. 26, 2022 | (CN) | .......................... 202210887446.5 |
| Jul. 26, 2022 | (CN) | .......................... 202210887448.4 |
| Jul. 26, 2022 | (CN) | .......................... 202221945575.7 |
| Oct. 24, 2022 | (CN) | .......................... 202222804046.1 |

(51) Int. Cl.
*A61M 37/00* (2006.01)

(52) U.S. Cl.
CPC ... *A61M 37/0076* (2013.01); *A61M 2205/106* (2013.01)

(58) Field of Classification Search
CPC .......... A61M 37/0076; A61M 37/0084; A61M 2202/0007; A61M 2205/106; A61M 2205/8281; A61M 2210/04; A61M 5/46

See application file for complete search history.

(56) References Cited

U.S. PATENT DOCUMENTS

| 4,798,582 A | 1/1989 | Sarath et al. |
| 7,695,486 B2 | 4/2010 | Dixon |
| D888,240 S | 6/2020 | Parcon |

(Continued)

*Primary Examiner* — Robert A Lynch

(57) ABSTRACT

An operating rod for a tattoo device includes: a drive mechanism, configured to drive an injection needle of the tattoo device to move; a first rod body, having a receiving cavity and a first fastening portion, wherein the receiving cavity is configured to receive the drive mechanism, and the first fastening portion is configured to fastened with the injection needle; and a second rod body, connected to at least part of the first rod body in a sleeved manner and configured with a second fastening portion, wherein the second fastening portion is configured to connect to the injection needle.

20 Claims, 81 Drawing Sheets

(56) References Cited

U.S. PATENT DOCUMENTS

| | | |
|---|---|---|
| 2011/0009860 A1 | 1/2011 | Chornenky et al. |
| 2015/0025561 A1* | 1/2015 | La Fontaine ..... A61M 37/0076 |
| | | 606/186 |
| 2017/0266045 A1 | 9/2017 | Kangastupa |
| 2017/0354810 A1* | 12/2017 | O'Brien, III ............ A61M 5/46 |
| 2019/0217072 A1 | 7/2019 | Xiao |
| 2020/0330740 A1 | 10/2020 | Bonnett |

* cited by examiner

INTRODUCTION NEEDLE AND TATTOO DEVICE

CROSS REFERENCE TO RELATED APPLICATIONS

The present application is a continuation-in-part application of the U.S. patent application Ser. No. 18/243,097, filed on Sep. 6, 2023, and the U.S. patent application Ser. No. 18/243,091, filed on Sep. 6, 2023. The present application is a continuation application of: the international patent application PCT/CN2023/128493, filed on Oct. 31, 2023, which claims priority of the Chinese patent application No. 202222804046.1, filed on Oct. 24, 2022; the international patent application of PCT/CN2023/102338, filed on Jun. 26, 2023, which claims priority of the Chinese patent application No. CN202210887448.4, filed on Jul. 26, 2022; the international patent application of PCT/CN2023/108804, filed on Jul. 24, 2023, which claims priority of the Chinese patent application No. CN202221945575.7, filed on Jul. 26, 2022; and the international patent application of PCT/CN2023/102336, filed on Jun. 26, 2023, which claims priority of the Chinese patent application No. CN202210887446.5, filed on Jul. 26, 2022. Contents of which are incorporated herein by their entireties.

TECHNICAL FIELD

The present disclosure relates to the field of tattoo tools, and in particular to an introduction needle and a tattoo device.

BACKGROUND

Tattoo is a method of embellish a face by introducing a colour pigment into a certain depth of the skin, and the colour pigment may be retained for months to years. A working principle of tattoo is disrupting the skin and applying color to the skin. An essential component of a tattoo tool in the art is a metal needle filament having one sharpened end. As demands of users are changed, semi-permanent tattoo has emerged in the art. For the semi-permanent tattoo, based on the principle of disrupting the skin and applying color to the skin, the pigment is retained at a shallower layer of the skin, i.e., at a layer between the epidermis and the dermis, or at a layer of the dermis near the epidermis. For a tattoo obtained in this way, the colour may be retained for 1-2 years and may be metabolized naturally.

Tattoo is actually coloring the skin by minimal invasion. The pigment is planted in the skin tissue to form a stable colour block. Since the epidermis is quite thin and is semi-translucent, the color of the pigment can be observed through the epidermis layer to cover up defects, to express the beauty but avoid shortcomings, and to modify and embellish the skin. Any pigment that is introduced into the skin is in a form of a small particle, and a diameter of the small particle is less than one micrometer. The small particle may be quickly surrounded by collagen but cannot be phagocytosed by phagocytes, and therefore, a mark is formed on the skin.

While producing a tattoo, a tattooist needs to use a tattoo tool to leave a mark on the skin. In order to produce the tattoo, which may be retained in the skin for 1 to 2 year and metabolized naturally afterwards, the tattooist needs to accurately control, while producing the tattoo, a depth that the needle reaches in the skin, and that is, a length that a needle projects out of the tattoo tool must be accurately adjusted.

However, in the art, the tattoo tool cannot accurately control a length that the metal needle filament at a front end of the tattoo tool projects out of the tattoo tool and the depth that the needle reaches in the skin. The tattooist has to adjust, by naked eyes and based on experience, the length that the metal needle filament at the front end of the tattoo tool projects out of the tattoo tool. While the tattoo tool is started up for adjustment, the tattooist has to adjust, by naked eyes, the length that the metal needle filament projects out of the tattoo tool while the needle filament is extending and retracting at a high speed. The adjustment, performed based on experience, may have a large error rate, it may be difficult for learners to learn the method, and the tattoo method may not be easily industrialized.

Therefore, it is urgent to propose a technical solution to solve the problems in the art.

SUMMARY OF THE DISCLOSURE

The present disclosure provides an operating rod for a tattoo device includes: a drive mechanism, configured to drive an injection needle of the tattoo device to move; a first rod body, having a receiving cavity and a first fastening portion, wherein the receiving cavity is configured to receive the drive mechanism, and the first fastening portion is configured to fastened with the injection needle; and a second rod body, connected to at least part of the first rod body in a sleeved manner and configured with a second fastening portion, wherein the second fastening portion is configured to connect to the injection needle.

The present disclosure further provides a tattoo device, including: the operating rod according to claim 1; and an injection needle, at least partially received in the operating rod and connected to the drive mechanism, wherein the drive mechanism is configured to drive the injection needle to reciprocately extend out of or to be received in the operating rod.

BRIEF DESCRIPTION OF THE DRAWINGS

In order to more clearly illustrate the technical solutions in the embodiments of the present disclosure or in the art, the accompanying drawings for the description of the embodiments or the art will be briefly introduced below. Obviously, the accompanying drawings in the following description are only some of the embodiments of the present disclosure. Any ordinary skilled person in the art may obtain other drawings based on the accompanying drawings without creative work.

FIG. 70b is a structural schematic view of an end face of a first docking portion according to another embodiment of the present disclosure.

FIG. 71 is a bottom plain view of the first docking portion being fastened to the first fastening portion according to an embodiment of the present disclosure.

FIG. 72 is a structural schematic view of an injection needle according to another embodiment of the present disclosure.

FIG. 73 is a structural schematic view of the operating rod connected to the injection needle according to an embodiment of the present disclosure.

FIG. 74 is another structural schematic view of the operating rod connected to the injection needle according to an embodiment of the present disclosure.

FIG. 75 is a perspective view of a bottom portion of the operating rod according to an embodiment of the present disclosure.

FIG. 76 is a structural schematic view of the top threads and the bottom threads when the injection needle being loosened from the operating rod according to an embodiment of the present disclosure.

FIG. 77 is another structural schematic view of the operating rod connected to the injection needle according to an embodiment of the present disclosure.

FIG. 78 is a perspective view of a bottom portion of the operating rod according to another embodiment of the present disclosure.

DETAILED DESCRIPTION

Figure 1A:
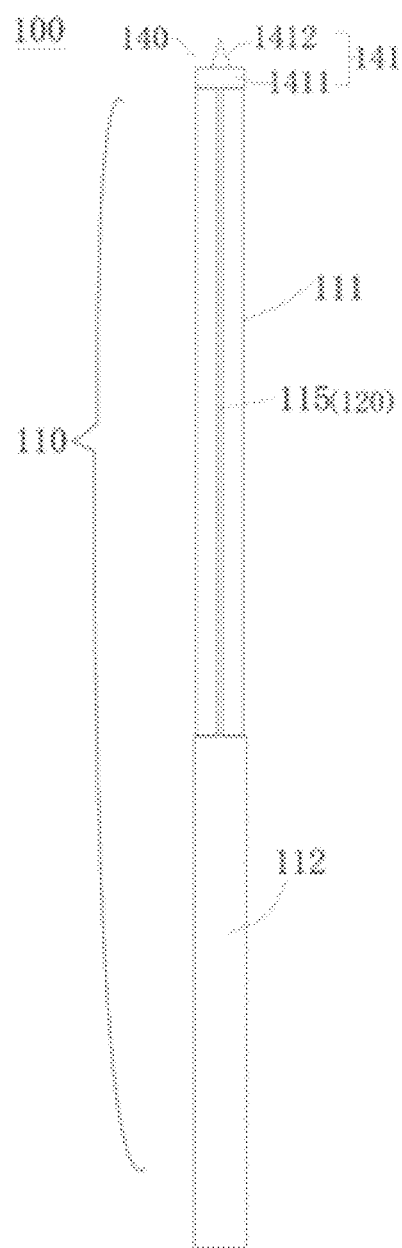
FIG. 1(a) is a structural schematic view of an introduction needle according to an embodiment of the present disclosure.

The technical solutions of the embodiments of the present disclosure will be described clearly and completely in the following by referring to the accompanying drawings. Obviously, the described embodiments show only a part of but not all of the embodiments of the present disclosure. All other embodiments obtained, based on the embodiments of the present disclosure, by any ordinary skilled person in the art without making creative work shall fall within the scope of the present disclosure.

In the description of the present disclosure, it is to be understood that any orientation or positional relationship indicated by the terms "top", "bottom", "top", "bottom", "inside", "outside", and so on, is an orientation or a positional relationship as shown in the accompanying drawings. The terms are used only to facilitate and simplify the description of the present disclosure, but do not indicate or imply that the device or element referred to must have a particular orientation or must be constructed and operated in a particular orientation. Therefore, the terms cannot be interpreted as limiting the present disclosure. In the present disclosure, the term "a plurality of" means two or more, unless otherwise expressly and specifically limited.

In the present disclosure, unless otherwise expressly provided and limited, the terms "mounted", "connected", "coupled", "fixed", and so on, shall be understood in a broad sense. For example, connection may be fixed connection, detachable connection, or two elements being configured as a one-piece structure; or may be mechanical connection or electrical connection; or may be direct connection, indirect connection through an intermediate medium, or two elements being internally connected or being interactive with each other. Any ordinary skilled person in the art shall understand specific meanings of the above terms in the present disclosure in a case-by-case manner.

The present disclosure will be illustrated in the following by referring to the drawings and the embodiments.

Figure 22A:
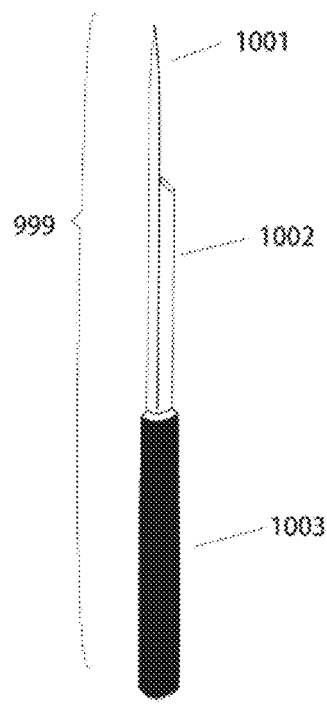
FIG. 22(a) is a structural schematic view of a single needle device.
Figure 22B:
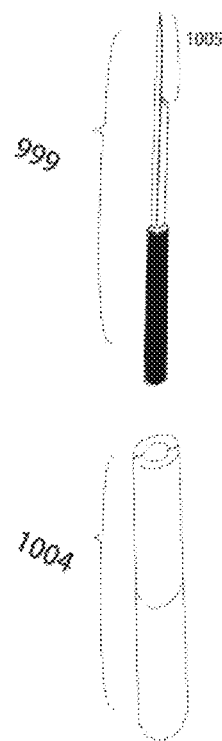
FIG. 22(b) is a schematic view of the single needle device shown in FIG. 22(a) being separated from a tattoo rod.

In order to perform fine colouring on a small area on the skin, for a tattoo device in the art, a single metal needle filament has a sharpened tip, serving as an operating end, and the single needle filament is welded to a needle handle. Further, the needle handle is secured, through a fixation end of the needle handle, to a tattoo rod. In this way, a single needle device is formed. As shown in FIG. 22(a), FIG. 22(a) shows a structural schematic view of the single needle device. The single needle device 999 includes a metal needle filament 1001, a needle handle 1002, a fixation end 1003 of the needle handle, a tattoo rod 1004, and a needle tip portion 1005. The single needle device 999 of FIG. 22(a) includes the single metal needle filament 1001 having a sharpened end, the needle handle 1002, the fixation end 1003 of the needle handle, the tattoo rod 1004, and the needle tip portion 1005. The needle tip portion 1005 is a part of the sharpened end of the single metal needle filament and protrudes from the needle handle. A length of the needle tip of the single needle device in the art is in a range from 3 mm to 10 mm. The needle tip 1005 of the single needle device 999 in the present embodiment is 3 mm. FIG. 22(b) is a schematic view of the single needle device shown in FIG. 22(a) being separated from a tattoo rod.

In an embodiment, the above single needle device may be taken to perform point-pricking to colour the skin. The point-pricking refers to the device repetitively pricking single points of the skin to bring the pigment into the skin. Alternatively, the above single needle device may be taken to draw lines to the colour the skin. Drawing lines to the colour the skin refers to the device breaking the skin from a single point and subsequently streaking the skin to bring the pigment into the skin. Although a process of manufacturing the single needle device in the art may be simple and the single needle device may be easily produced, the operating end of the single needle device in the art may cause the following colouring and safety problems. While colouring the skin to produce the tattoo, the operating end may prick the skin to reach an excessively large depth, and in this case, the pigments may spread outside a target colour area under the skin. Therefore, the pigment may be unable to be completely metabolized for several years, also known as "colour fading" in the tattoo industry.

According to scientific data, an average thickness of the epidermis of the human face is in a range from 0.2 mm to 1.0 mm, an average thickness of the epidermis at the eyebrow region is 0.5 mm, and an average thickness of the epidermis at the eyelid region is 0.33 mm. A thickness of one piece of conventional A4 paper of 80 g is 0.11 mm. That is, a thickness of the epidermis at the relatively thinner region of the human face is approximately equal to thicknesses of 2 to 3 pieces of conventional A4 paper. It may be difficult to control, based on subjective experience, a depth that is reached by the single needle device in the art piercing into the skin having the above thickness. By analyzing a large number of cases, "colour fading" cases may occur highly frequently, and this is because a piercing depth of the single needle device of the tattoo tool in the art may not be limited effectively, and a large error may be resulted due to the piercing depth being controlled by subjective determination of the operator only. Therefore, the piercing depth of tattoo may be determined and controlled in advance according to the thickness of the epidermis of various operating regions, such that a bleeding rate may be reduced to prevent occurrence of "colour fading".

According to accumulated data from the industry and experimental analysis, when the skin at the eyebrow region is pierced for a depth of 0.05 mm to 1.0 mm, the pigment may be retained at the skin for 3 months to 10 years in average. As the skin is pierced more deeply, the pigment may be retained longer. When the piercing depth is more than 1.0 mm, an average time length that the colour can be retained is more than 10 years. In the art, semi-permanent tattoo is the main demand in the market. The semi-permanent tattoo refers to the colour being retained for 1-2 years, and the piercing depth into the skin shall be controlled in the range of 0.3 mm to 0.6 mm, i.e., approximately thicknesses of 2-4 pieces of conventional A4 paper, each in the weight of 80 g.

In order to verify a relationship between the depth that the single needle device pierces into the skin and the time length that the colour is retained, a following verification experiment is performed.

For the tattoo tool in the art, a single needle device in a commonly used model (i.e., a diameter of the needle filament is 0.30 mm, a length of the needle tip is 3 mm) is taken to perform various pricking tests. For each of the various pricking tests, the single needle device is taken to prick a simulated silicone skin, and all simulated silicone skins applied in the various pricking tests are in a same specification. For the various pricking tests, an average height that the needle tip leaves the simulated silicone skin is 5 mm, and the needle tip pricks the simulated silicone skin twice per second in average. When an average depth that the needle tip pierces into the simulated silicone skin is 0.7 mm, approximately 0.06 kg force is applied to achieve the average depth. When an average depth that the needle tip pierces into the simulated silicone skin is 0.3 mm, approximately 0.04 kg force is applied to achieve the average depth. That is, that is, a difference of 0.02 kg force causes a 0.4 mm error in the depth that the needle tip pierces into the simulated silicone skin. The difference of 0.02 kg force is equivalent to a weight of 4-5 pieces of conventional A4 paper. It may be difficult to achieve this precision subjectively by human experience. For example, at the eyebrow region, when the depth that the skin is pierced is in a range of 0.3 mm to 0.6 mm, the colour may be retained to for 1-2 years. The error of only 0.02 kg force may cause the needle tip to pierce into the skin excessively deeply, resulting in the colour being retained for an excessively long period of time. Therefore, the main demand of retaining the colour in the skin for 1-2 years may not be met, customer complaints may be caused easily.

Therefore, the depth that the single needle device of the tattoo tool in the art pierces into the skin cannot be precisely controlled, causing the "colour fading" problems. Further, the depth that the single needle device pierces into the skin is closely related to the time length that the pigment is retained in the skin. An effect of the tattoo may be affected since depths of various piercings are inconsistent and not controllable.

In order to solve deficiencies of the single needle device in the art, the present disclosure provides a tattoo needle, wherein the depth that the tattoo needle may pierce into the skin may be accurately defined in advance, such that the tattoo needle may be prevented from piercing into the skin excessively deeply, and therefore, the pigments may be prevented from spreading to a non-target colouring region.

A specific structure of the introduction needle provided by the present disclosure will be described in detail below by referring to the accompanying drawings.

Embodiment 1:

As shown in FIG. 1(a) to FIG. 1(d), in an embodiment, an introduction needle 100 may include a liquid guiding member 110 and a needle piercing portion 140 disposed at an end of the liquid guiding member 110. The needle piercing portion 140 includes a piercing projection 141. The piercing projection 141 includes a substrate 1411 and a needle tooth 1412. The needle tooth 1412 is fixedly arranged on an end face of the substrate 1411. A central axis of the needle tooth 1412 is perpendicular to the end face of the substrate 1411. When the needle is piercing the skin, the substrate 1411 may limit a depth that the needle pierces the skin. The substrate 1411 presses against the skin to limit the depth that the needle tooth 1412 pierces into the skin. The liquid guiding member 110 may be columnar. The other end face of the substrate 1411 is fixed to an end of the columnar liquid guiding member 110. A central axis of the columnar liquid guiding member 110 is parallel to the central axis of the needle tooth 1412. The structure of the introduction needle 100 may be similar to a pen. The liquid guiding member 110 may be similar to a barrel of the pen. The needle piercing portion 140 may be similar to a tip of the pen. The liquid guiding member 110 may pierce the skin in the vertical direction, ensuring that a piercing position may not be shifted, the needle tip may not slip, and a redundant wound may not be generated.

As shown in FIG. 1(a) to FIG. 1(d), in an embodiment, the liquid guiding member 110 may include a liquid guiding post 111 and a connecting rod 112 connected to the liquid guiding post 111. That is, the liquid guiding member 110 includes two parts, one of the two parts guides ink to flow, and the other one of the two parts is configured for connection and driving. The connecting rod 112 is connected to a drive portion. The liquid guiding member 110 reciprocates, driven by the drive portion, along the central axis of the liquid guiding member 110. In a case, the drive portion may be a motorized rod, and that is, the connecting rod 112 of the liquid guiding member 110 is directly connected to the motorized rod (which may be fixed connection or a non-fixed connection (including abutting connection, hanging connection, and contact connection)). The motorized rod directly drives the liquid guiding member 110 to move. In another case, the drive portion may be an elastic member 170, such as a spring. The connecting rod 112 of the liquid guiding member 110 is connected to an end of the spring. A case (or a member fixedly connected to the case) is connected to the other end of the spring. Further, an external force is applied to drive the spring to be deformed. When the liquid guiding member 110 is moving along an axial direction of the case 150 towards a needle outlet end, the liquid guiding member 110 may be reset by a force from the deformed elastic member, such that the liquid guiding member 110 moves reciprocately within the case 150. In still another case, an operator may also hold the connecting rod 112 by hand to directly tattoo.

In order to achieve various tattoo patterns and tattoo positions, the present embodiment provides a piercing projection 141, as shown in FIG. 3(*d*). The piercing projection 141 may include a substrate 1411 and a needle tooth 1412 arranged on the substrate 1411. The substrate 1411 serves as a depth limiting plate to limit a depth that the needle tooth 1412 pierces into the skin. The substrate 1411 and the needle tooth 1412 may be configured as a one-piece and integral structure, or configured as separated elements being fixedly connected with each other. When the substrate 1411 and the needle tooth 1412 are configured as the one-piece and integral structure, connection strength and stability of the needle tooth 1412 may be enhanced. Further, safety of the needle tooth 1412 may be improved while the needle tooth 1412 is piercing the skin. The one-piece and integral structure may be suitable for a high frequency piercing process.

The advantages of the introduction needle in the present disclosure, compared to the single needle device in the art, will be illustrated below by referring to FIGS. 23(*a*), 23(*b*), 24(*a*), and 24(*b*).

Figure 23A:
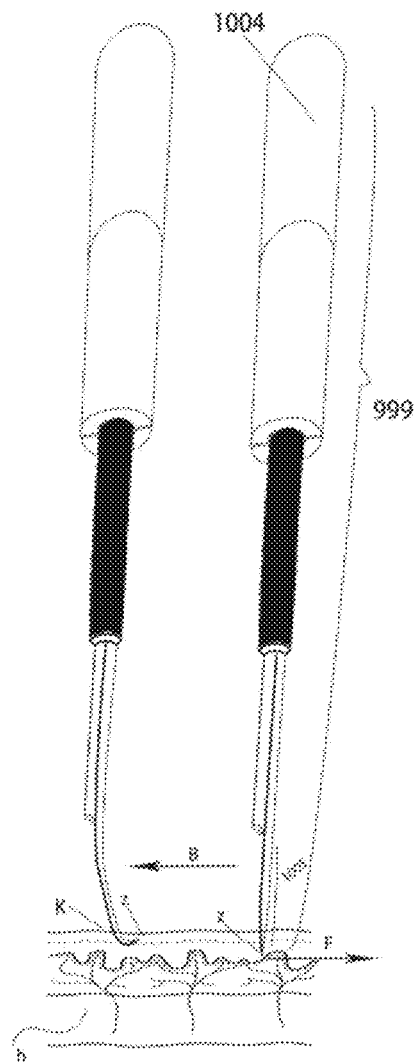
FIG. 23(a) is a cross-sectional of piercing a single needle device in the art into the skin.
Figure 23B:
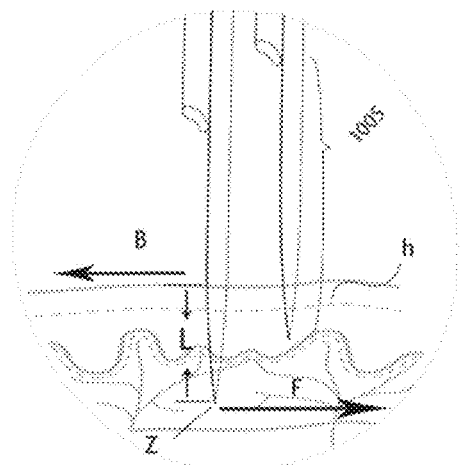
FIG. 23(b) is a schematic view of a force applied to a tip of the metal needle filament of the single needle device in the art, as shown in FIG. 34(a), while the single needle device is piercing into the skin.

As shown in FIG. 23(*a*), a cross-sectional structure of the skin is noted as h. The single needle device 999 of the tattoo tool in the art is connected to the tattoo rod 1004. The operator may hold the tattoo rod 1004 by hand to repetitively streak the skin along a direction indicated by an arrow B to colour the skin. A front end Z of the needle tip 1005 is under the skin and may be subjected to a resistance force F in a direction opposite to the direction B. The front end Z of the needle tip 1005 may be bent, as shown at K. Further, as shown in FIG. 23(*b*), the front end Z of the needle tip 1005 under the skin may be bent because of a force moment. The force moment=force arm*force (M=L*F). In a case that all forces in the horizontal direction are the same, as the needle tip pierces into the skin more deeply, the force arm L is larger, and the force moment M applied to the front end Z of the needle tip 1005 is larger. Therefore, the front end Z of the needle tip 1005 may be bent more easily. Therefore, the introduction needle provided by the present disclosure may limit the depth that the needle tip pierces into the skin, and that is, a maximum moment applied to the needle tip is limited, and the needle tip may be prevented from being bent.

Figure 24A:
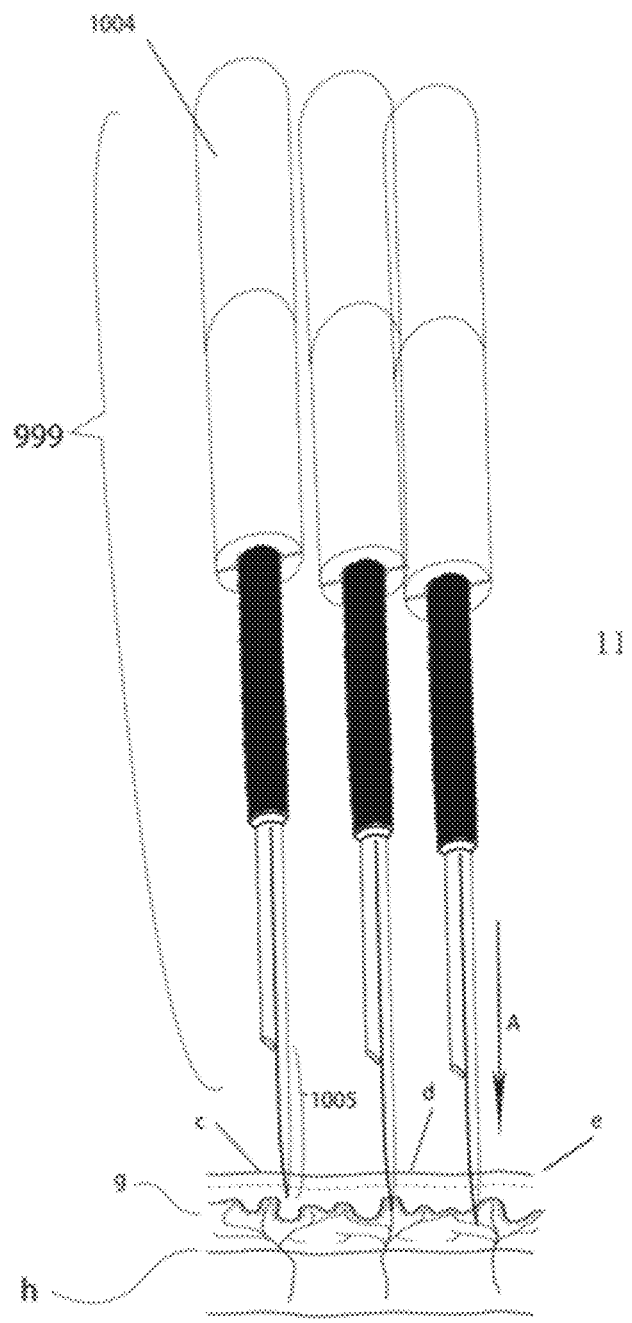
FIG. 24(a) is a cross-sectional view of the single needle device in the art piercing into the skin.
Figure 24B:
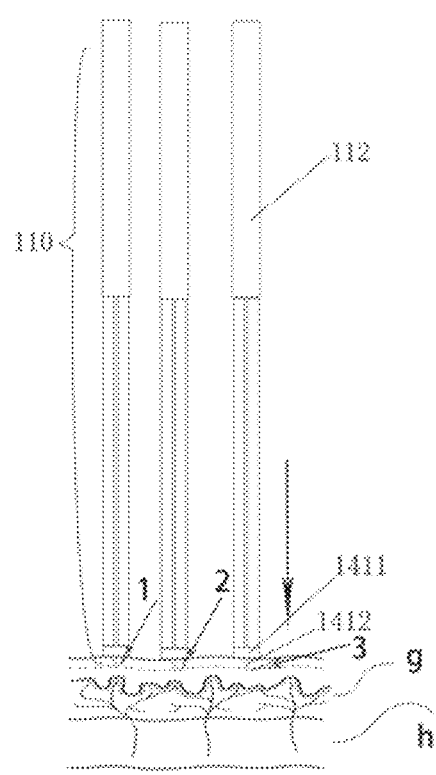
FIG. 24(b) is a cross-sectional view of the single needle device, according to an embodiment of the present disclosure, piercing into the skin.

As shown in FIG. 24(*a*), the cross-sectional structure of the skin is noted as h, and subcutaneous blood vessels are noted as g. The operator holds the tattoo rod 1004 by hand to repeatedly prick the skin along the arrow A in an up-down direction to colour the skin. The needle tip 1005 pierces into the skin to reach position as indicated by c, d, and e, in FIG. 24(*a*), and the position c, d, and e refer to different depths under the skin. The depths of the positions d and e show that the needle tip has reached locations at which the subcutaneous blood vessels are located. As shown in FIG. 24(*b*), the operator may alternatively directly hold the connecting rod 112 to repeatedly prick the skin to colour the skin. The needle tooth 1412 having a predetermined piercing length pierces into the skin, and the substrate 1411 contacts the skin to form a barrier, such that the piercing depth is limited. As indicated by points 1, 2, and 3 shown in FIG. 24(*b*), the piercing depths are controllable and are consistent. A height of the needle tooth 1412 is predetermined within a certain range to prevent the subcutaneous blood vessels from being pierced and to prevent the tip from being bent due to an excessive large force moment.

Embodiment 2:

As shown in FIG. 3(*c*) to FIG. 3(*d*), in an embodiment, the needle tooth 1412 of the present disclosure may be a protrusion protruding from the substrate 1411. A size of a cross sectional area of the protrusion decreases along a direction that the needle teeth piece into the skin. For example, the size of the cross sectional area of the protrusion decreases in a direction from the substrate 1411 towards a free end of the protrusion. A bottom of the needle tooth is connected to the substrate 1411, and the free end of the needle tooth is a top end. Based on repeated experiments, in order to achieve a better effect of guiding the pigments, a height range $h1412$ of the needle tooth is $50\ \mu m \leq h1412 \leq 1000\ \mu m$, and a diameter range $D1412$ of the bottom of the needle teeth is $20\ \mu m \leq D1412 \leq 500\ \mu m$, in general, $D1412 \leq h1412$.

In an embodiment, the substrate 1411 is in an arbitrary polygonal shape. The needle tooth 1412 is disposed on an end face of the substrate 1411. In order to achieve the better effect of guiding the pigments, a minimum edge length of the substrate 1411 is recorded as $D1411$. In the case $D1411 > D1412$, the pigments may flow to reach the substrate 1411 from the relatively thick liquid guiding post 111 and may further be guided from the substrate to the needle tooth 1412.

As shown in FIG. 4(*d*), a diameter of a first end face 1111 of the liquid guiding post 111 is $D1111$. Based on repeated experiments, in order to achieve the better effect of guiding the pigments and to have a certain extent of rigidity, $180\ \mu m \leq D1111 \leq 1800\ \mu m$, and $D1111 > D1411$. Further as shown in FIG. 4(*c*) and FIG. 4(*d*), three channels 115 are defined in the liquid guiding post 111 (CH1, CH2, and CH3 in FIG. 4(*c*) each represents one of the three channels). As shown in FIG. 4(*c*), a length of the liquid guiding post 111 is $L111$, and $L111 > D1111$. In an embodiment, in order to allow the device to carry an increased amount of ink and to release the ink continuously and slowly, $L111 > 2 \times D1111$. That is, the length of the liquid guiding post 111 is greater than two times of the diameter of the first end face of the liquid guiding post 111. Of course, a cross section of the piercing projection 141, taken by the substrate 1411, may be arbitrary polygonal, for example, the cross section may be triangular, quadrilateral, pentagonal, or in other regular or irregular polygonal shapes. When the shape of the substrate 1411 is arbitrary polygonal, an axial length of the liquid guiding post 111 is at least two times of the length of the shortest edge of the first end face 1111 of the liquid guiding post 111, and the axial length of the liquid guiding post 111 is greater than a length of the longest edge of the first end face 1111.

Figure 5A:
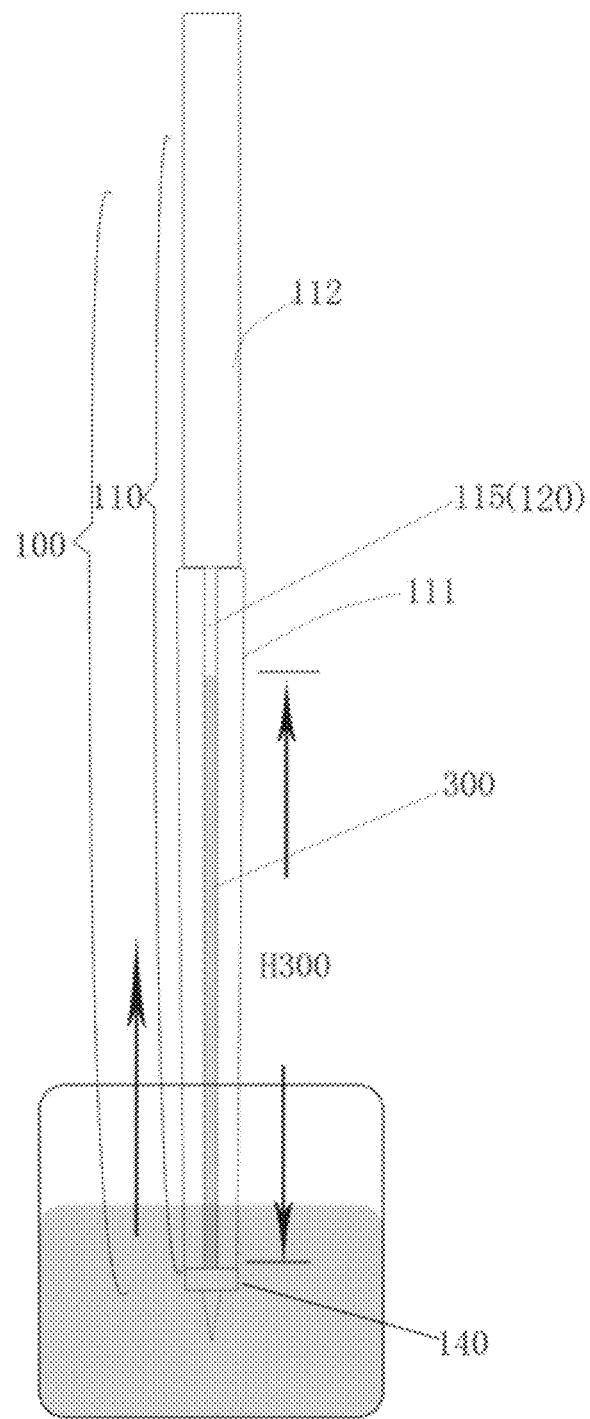
FIG. 5(a) is a schematic view showing a state of the introduction needle while the introduction needle is intaking ink, according to an embodiment of the present disclosure.
Figure 5B:
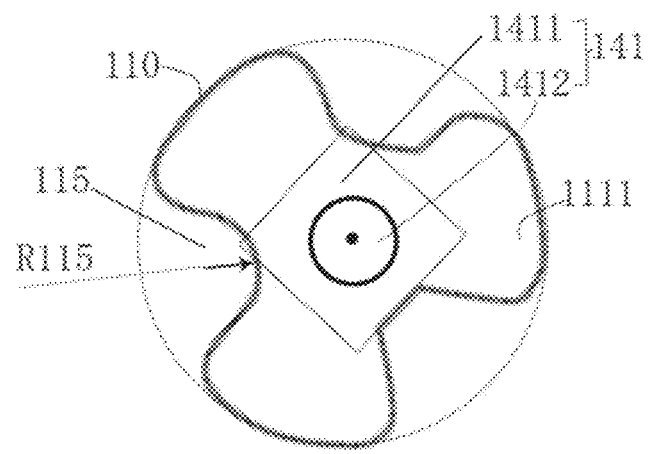
FIG. 5(b) is a top view of the introduction needle shown in FIG. 5(a), viewed from a viewing angle.
Figure 5C:
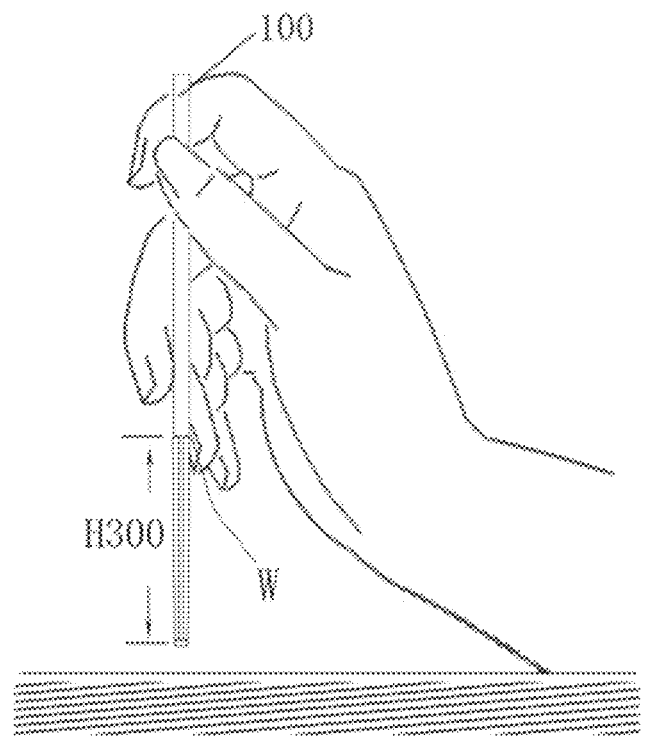
FIG. 5(c) is a schematic view showing a state of the introduction needle in FIG. 5(a), which has intaken the ink, piercing into the skin, according to an embodiment of the present disclosure.
Figure 6:
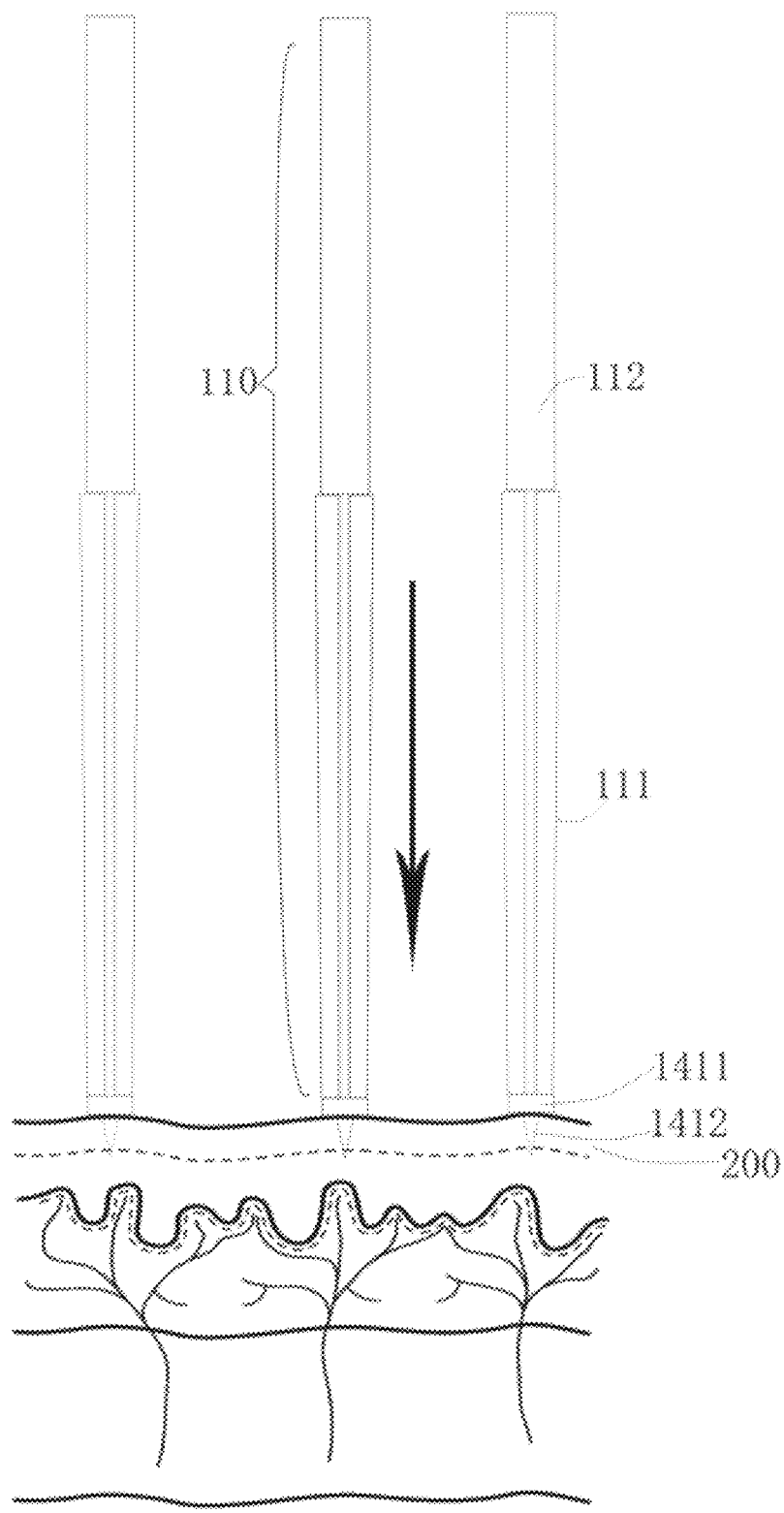
FIG. 6 is a schematic view showing a state of the introduction needle piercing into the skin according to an embodiment of the present disclosure.

As shown in FIG. 5(*a*), the liquid guiding member 110 is arranged with a capillary liquid storage unit 120. A channel 115 in the capillary liquid storage unit 120 is defined in an outer wall of the liquid guiding member 110. Further, a capillary principle is applied to enable the channel 115 to store the pigments (the pigments and the ink in the present disclosure both refer to dyes that can colour the skin). The needle piercing portion 140 of the introduction needle 100 and a bottom of the channel 115 are submerged into the pigments, and the pigments rises along the channel 115 against the gravity. In this case, the channel 115 serves as a capillary liquid storage unit 120 that can temporarily store the pigments. When the introduction needle that has adsorbed the pigments is being used, the capillary liquid storage unit may continuously supply ink to the needle tooth of the needle piercing portion. When the liquid guiding member 110 is dipped into the pigments to intake the pigments, the pigments rises along the capillary liquid storage unit 120 to form a pigment column. For simple illustration, a height of the pigment column is recorded as H300.

As shown in FIG. 5(*b*), the piercing projection 141 is fixed to the first end face 1111 of the liquid guiding member 110, and a radius of the channel 115 in the outer wall of the liquid guiding member 110 may be recorded as R115.

By collecting and analyzing data, a density of the pigments in the art at room temperature is about 0.7-1.31 g/ml, and a surface tension of the pigments at the room temperature is almost equal to a surface tension of water, which is about 72 mN/m. A capillary formula is as follows: a height h that the liquid rises along a capillary tube=2*surface tension coefficient*cosθ/(density of the liquid* gravitational acceleration g*radius of the capillary tube r). The θ is an angle between a liquid surface and a wall of the capillary tube. The radius of the channel R115 of the liquid storage unit 120 corresponds to the radius of the capillary tube r in the capillary formula. According to the experimental test and verification of the capillary formula, as a value of the R115 is reduced, a value of the H300 is increased. That is, as the channel of the capillary liquid storage unit 120 is thinner, the height of the pigment column H300 is higher, and more pigments may be carried. Therefore, the needle may not dip the pigments frequently, the tattooing may be performed continuously and efficiently.

In an embodiment, the liquid guiding member 110 of the introduction needle 100 is made of polycarbonate. Based on precision of the main production process in the art, the radius of the channel of the capillary liquid storage unit 120 may be made to have a precision of 0.1 mm, and the height of the pigment column H300 may be more than 100 mm. However, as shown in FIG. 5(*c*), according to a conventional way that the operator holds the introduction needle 100 by hand and a measurement of dimensions of a general human hand, a lowest position W of the introduction needle 100 that is held by the hand is generally not more than 50 mm from the needle tip. Therefore, the height H300 of the channel of the capillary liquid storage unit 120 arranged on the introduction needle 100 in the present embodiment is <50 mm.

Figure 2:
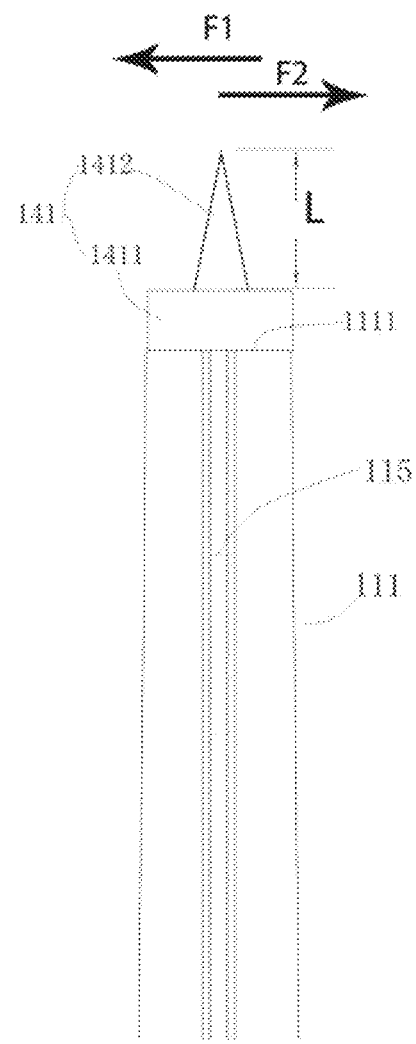
FIG. 2 is a structural schematic view of a liquid guiding post and a piercing projection according to an embodiment of the present disclosure.
Figure 3A:
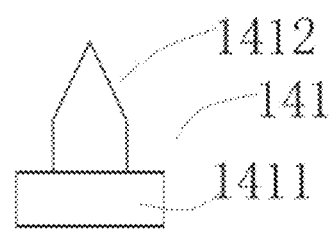
FIG. 3(a) is a front view of the piercing projection according to an embodiment of the present disclosure.
Figure 3B:
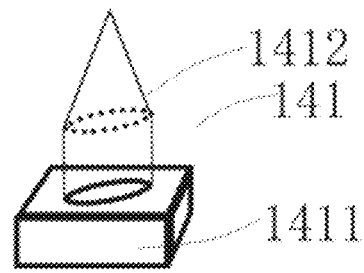
FIG. 3(b) is a perspective view of the piercing projection shown in FIG. 3(a).
Figure 3C:
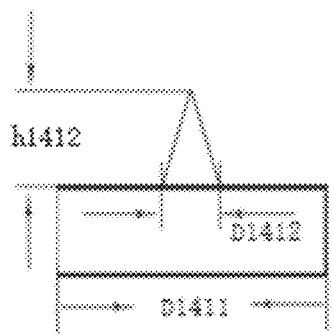
FIG. 3(c) is a front view of the piercing projection according to another embodiment of the present disclosure.
Figure 3D:
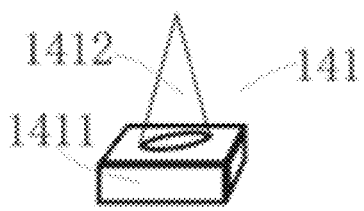
FIG. 3(d) is a perspective view of the piercing projection shown in FIG. 3(c).

As shown in FIG. 2, in an embodiment, in order to achieve the better effect of guiding the pigments, the liquid guiding post 111 is fixed, by adhering, to the substrate 1411 of the piercing projection 141. As shown in FIG. 4(*e*), at least one corner V1, V2, and/or an edge M of the substrate 1411 on which the piercing projection 1411 is arranged is aligned with (infinitely approach) an edge of the outer wall of the liquid guiding post 111.

In an embodiment, the substrate 1411 of the piercing projection 141 is disposed at a middle of an end face of the liquid guiding member 110, and a distance from the edge of the outer wall of the liquid guiding member to one corner or one edge of the substrate is not more than 0.18 mm. That is, in an embodiment, the substrate may be disposed at a center of the first end face. However, in order to achieve the better effect of guiding the pigments, a distance from the edge of the outer wall of the liquid guiding member to one corner or one edge of the substrate is not more than 0.18 mm.

As shown in FIG. 7(*a*), for the introduction needle in the present embodiment an adhesive seam is defined between the liquid guiding member 110 and the piercing projection 141. After use, the introduction needle 100 may be functionally destroyed by separating, by any sharp instrument, the liquid guiding member 110 from the piercing projection 141.

Embodiment 3:

In an embodiment, FIG. 1(*a*) shows an introduction needle 100, and a depth that the introduction needle 100 pierces into the skin from a single point, may be accurately predefined. The introduction needle 100 includes a liquid guiding member 110, a needle piercing portion 140, and a channel 115 defined in an outer wall of the liquid guiding member 110. The channel 115 serves as a capillary liquid storage unit 120.

In an embodiment, as shown in FIG. 4(*a*), the liquid guiding post 111 includes three metal filaments ZC1, ZC22, and ZC3 that are cut flat. The metal filaments ZC1, ZC22, ZC3 are adjacent to each other and are not fixedly connected to each other. A gap between the filaments has a capillary effect and serves as the capillary liquid storage unit. In an embodiment, the liquid guiding post 111 is fixedly connected to the connecting rod 112. The liquid guiding post 111 is welded and fixed to the substrate 1411 of the piercing projection 141.

In an embodiment, as shown in FIG. 3(*a*) and FIG. 3(*b*), the needle tooth 1412 of the present disclosure includes a tail pin and a top pin integrally formed with an end of the tail pin. The tail pin may be columnar, and the top pin may be protruding from the tail pin. A size of a cross sectional area of the top pin decreases in a direction extending from the tail pin to a free end of the top pin away from the tail pin, and the other end of the columnar tail pin is fixedly connected to the substrate.

In an embodiment, as shown in FIG. 4(*b*), the edge of the outer wall of the liquid guiding post 111 is aligned with (indefinitely approach) at least one corner J1, J2, J3 of the substrate 1411 and/or with one edge P of the substrate 1411.

In an embodiment, the liquid guiding post 111 is welded and fixed to the piercing projection 141 of the introduction needle 100, in the present embodiment. The piercing projection 141 is made of monocrystalline silicon. After usage, the introduction needle 100 may be functionally destroyed by knocking, by any sharp instrument, off the needle tooth 1412. The destroyed introduction needle may be shown as FIG. 7(*b*).

FIG. 1(*d*) shows an introduction needle 100, and a depth that the introduction needle 100 pierces into the skin from a single point, may be accurately predefined. The introduction needle 100 includes a piercing projection 141, a liquid guiding post 111, and a capillary liquid storage unit 120. The piercing projection 141 includes one needle tooth 1412 and a substrate 1411. A depth that the needle tooth 1412 pierces into the skin may be predefined, and the needle tooth 1412 is mounted on the substrate 1411. The needle tooth 1412 is a protrusion protruding from the substrate 1411. A size of a cross sectional area of the protrusion decreases along a direction that the needle teeth piece into the skin. For example, the size of the cross sectional area of the protrusion decreases in a direction from the substrate 1411 towards a free end of the protrusion. For example, the needle tooth may be conical. The substrate 1411 and the needle tooth 1412 are configured as a one-piece and integral structure. The substrate 1411 limits the depth that the needle tooth 1412 pierces into the skin. In an embodiment, as shown in FIG. 1(d), the liquid guiding post 111 is a strip. A fibrous substance may be attached to the outer wall of the liquid guiding post 111. A gap in a body of the fibrous substance and a gap between the body of the fibrous substance and the outer wall of the liquid guiding post 111 cooperatively serve as the capillary liquid storage unit 120.

Figure 4A:
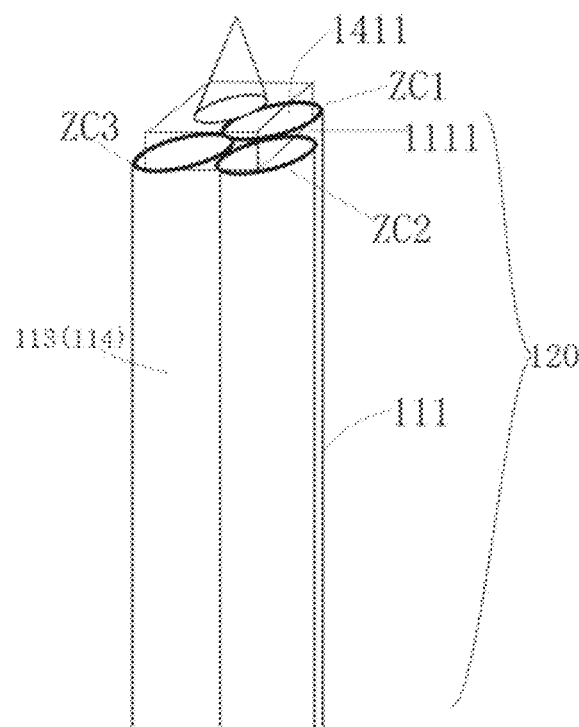
FIG. 4(a) is a perspective view of a portion of the introduction needle according to an embodiment of the present disclosure.
Figure 4B:
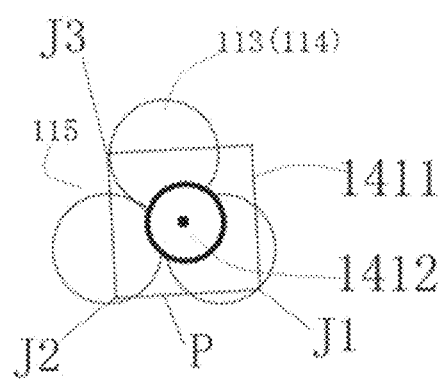
FIG. 4(b) is a schematic view of the introduction needle shown in FIG. 4(a), viewed from a viewing angle.
Figure 4C:
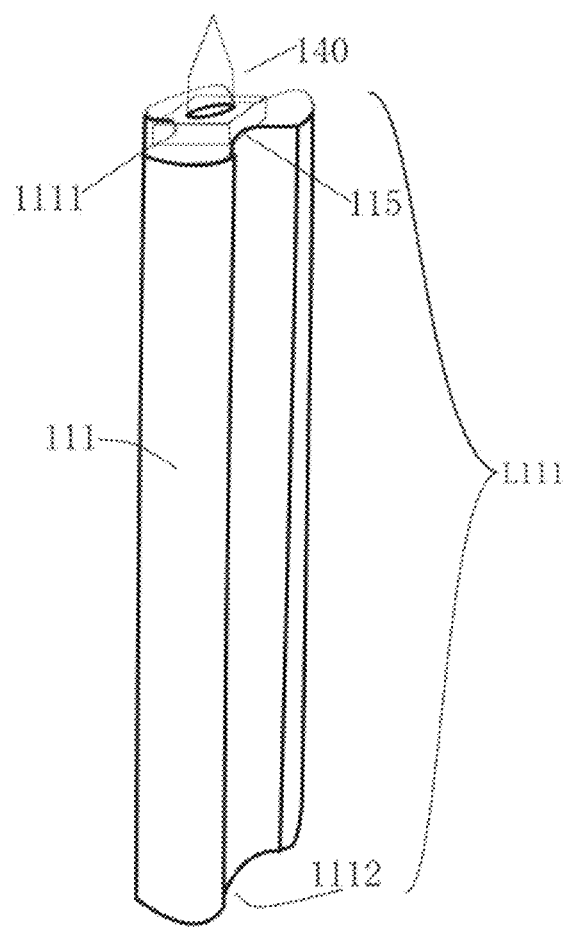
FIG. 4(c) is a perspective view of a portion of the introduction needle according to another embodiment of the present disclosure.
Figure 4D:
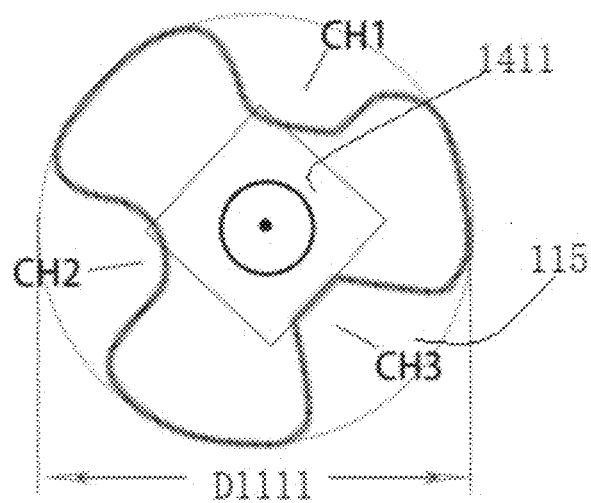
FIG. 4(d) is a schematic view of the introduction needle shown in FIG. 4(c), viewed from a viewing angle.
Figure 4E:
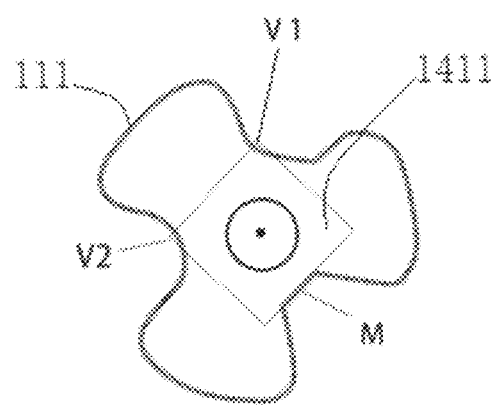
FIG. 4(e) is a schematic view of the introduction needle according to another embodiment of the present disclosure.

Embodiment 4:

As shown in FIG. 4(c), in an embodiment, the liquid guiding post 111 may have a first end face 1111 and a second end face 1112. The central axis of the liquid guiding column 111 extends through a center of the first end face 1111 and a center of the second end face 1112. The liquid guiding column 111 may be a column in any shape, such as a cylinder, a quadratic column, a cone-like column (or a circular truncated cone), an irregular column, and so on.

As shown in FIG. 1(a), a side face of the substrate 1411 is fixed to the first end face 1111 of the liquid guiding post 111 (the substrate may be adhered to and fixed to the first end face). The connecting rod 112 may be fixedly or detachably connected to the second end face 1112 of the liquid guiding post 111. The connecting rod 112 may be a column or in other shapes. The connecting rod 112 is substantially configured to connect the liquid guiding post 111 to the drive portion.

In an embodiment, a shape of the liquid guiding post 111 of the present disclosure may be arbitrary, as long as any one of the following conditions is met.

For a condition 1, a shape of the first end face 1111 is the same as a shape of the second end face 1112, and a size of the first end face 1111 is the same as a size of the second end face 1112.

For a condition 2, the shape of the first end face 1111 is the same as the shape of the second end face 1112, and the size of the first end face 1111 is less than the size of the second end face 1112.

For a condition 3, the shape of the first end face 1111 is different from the shape of the second end face 1112, and the size of the first end face 1111 is less than the size of the second end face 1112.

Based on the above conditions, the most basic characteristics of the liquid guiding member 110 is that the liquid guiding member 110 is a column. As long as the liquid guiding member 110, when being vertically disposed, may guide and direct liquid to flow, the shape of the liquid guiding member 110 is arbitrary. The shape of the liquid guiding member 110 may be determined based on the operator's demands. The accompanying drawings, which show that the shape is columnar and conical-like, are for illustrating the structure of the liquid guiding member only, and shall not be interpreted as limiting the shape of the shape of the liquid guiding member 110.

In an embodiment, the axial length of the liquid guiding post 111 is greater than a length of the longest edge or a diameter of a cross section of the first end face 1111 of the liquid guiding post 111. That is, the liquid guiding post 111 of the present disclosure is preferably an elongated column.

In an embodiment, the axial length of the liquid guiding post 111 is at least two times of the length of the shortest edge or the diameter of the first end face 1111 of the liquid guiding post 111, and the axial length of the liquid guiding post 111 is greater than the length of the longest edge or the diameter of the first end face 1111. When this length-to-diameter ratio is met, the shape of the liquid guiding member 110 is standardized, and the elongated liquid guiding member 110, when being vertically disposed, provides a better liquid guiding and storage effect.

Embodiment 5:

In the tattoo process, the tattoo ink 300 (or dye) may be introduced into a superficial layer of the skin through the tattoo tool. The tattoo tool in the art may not adsorb, when being submerged into the ink 300, a large amount of ink 300. In a process that the tool pierces into the skin highly frequently, the amount of ink in the tattoo tool does not reach the amount of ink required for one piercing stage. Therefore, a high rate of empty needle during piercing may be caused. In order to improve the above mentioned defects of the tattoo tool in the art, the liquid guiding member 110 of the introduction needle in the present disclosure is improved to meet the amount of ink required for one tattoo process. The structure of the liquid guiding member 110 will be described in detail below.

As shown in FIG. 4(a) to FIG. 4(d), FIG. 5(a), and FIG. 6, the capillary liquid storage unit 120 is arranged in the liquid guiding post 111. Liquid stored in the capillary liquid storage unit 120 (under the gravitational force or other forces) is guided to flow to the needle piercing portion 140. The needle tooth 1412 pierces into the surface of the skin 200, and at the same time, the liquid is introduced into the surface of the skin 200 along the needle tooth 1412. The capillary liquid storage unit 120 may temporarily store the ink 300. The liquid guiding member 110 may be submerged in an ink bottle, and the capillary liquid storage unit 120 in the liquid guiding member 110 may adsorb and temporarily store the ink. When the liquid guiding member 110 carries the needle tooth 1412 of the needle piercing portion 140 to pierce into the skin, the ink 300 stored in the capillary liquid storage unit 120 is gradually guided to flow to the tip of the needle tooth 1412. In the present disclosure, the capillary liquid storage unit 120 is arranged to allow the the liquid guiding member 110 to release the ink gradually, ensuring continuous supply of the ink and reducing a rate of empty needles.

Figure 7A:
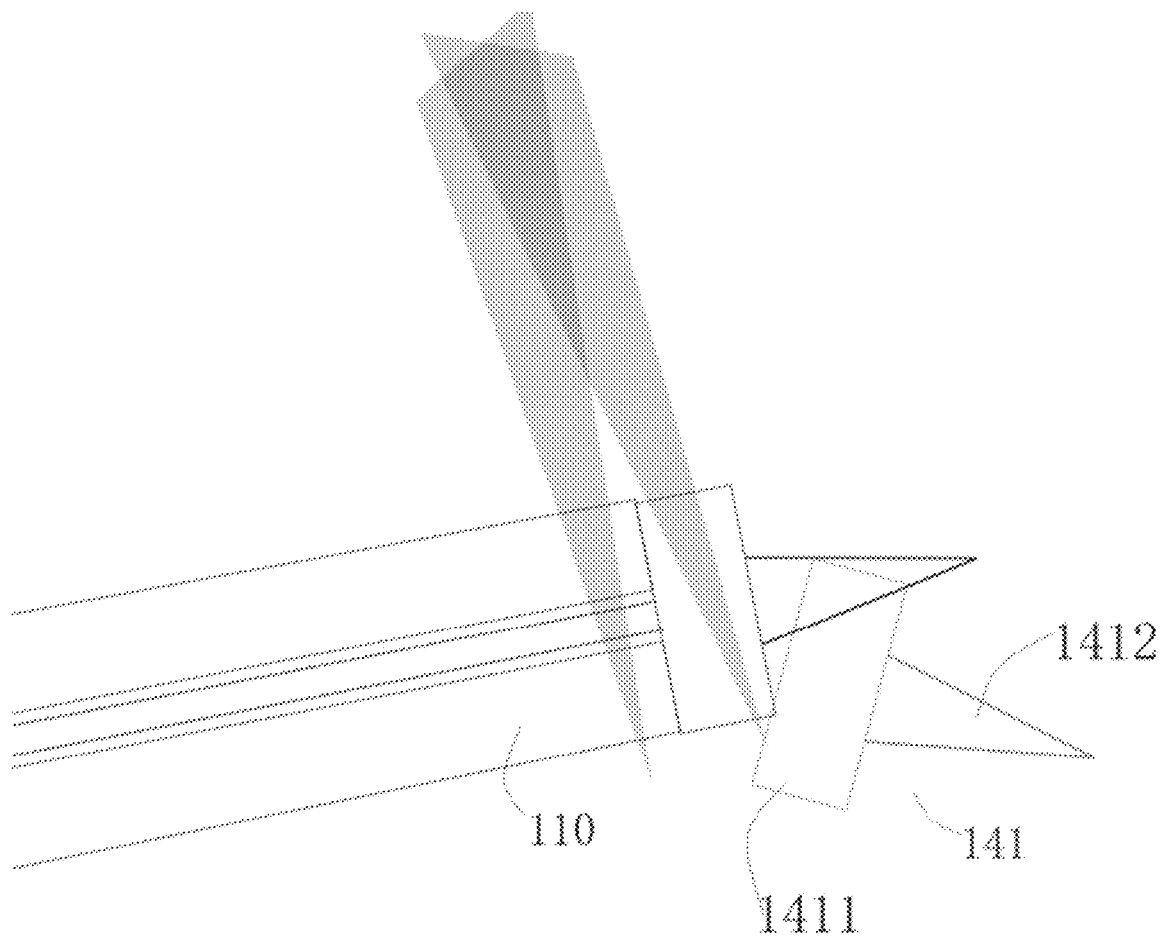
FIG. 7(a) is a schematic view showing a state of destroying an introduction needle after being used according to an embodiment of the present disclosure.
Figure 7B:
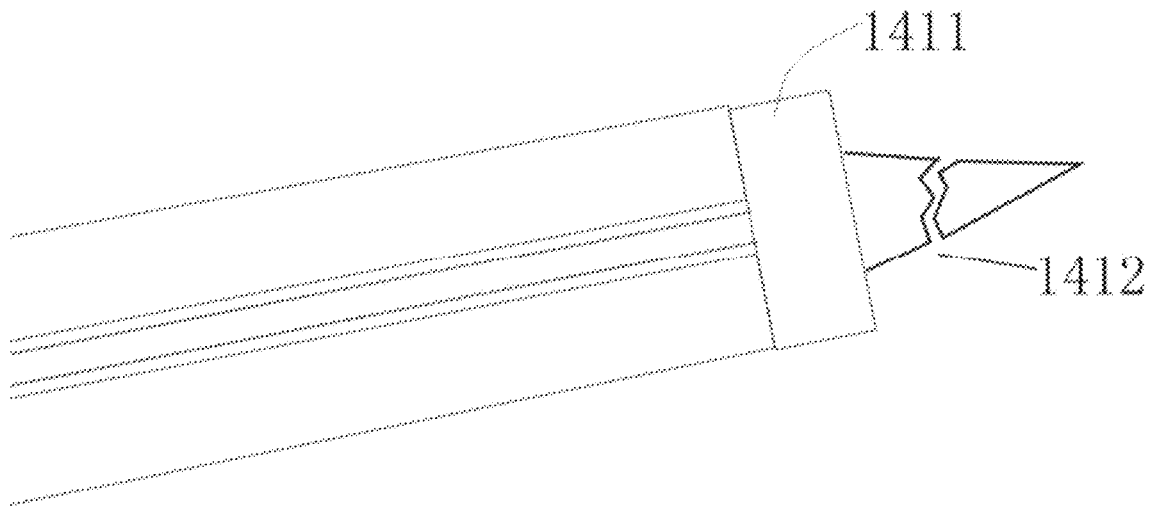
FIG. 7(b) is a schematic view showing a state of destroying an introduction needle after being used according to another embodiment of the present disclosure.

According to the above embodiments, the introduction needle is required to be break into the skin during the tattoo process. Therefore, the introduction needle that has been used needs to be destroyed to prevent microbial spread caused by secondary usage. The introduction needle provided by the present disclosure has taken this into account. Therefore, as shown in FIGS. 7(a) to 7(b), the needle tooth 1412 of the introduction needle are destroyed. Alternatively, the needle piercing portion of the introduction needle is directly destroyed, and the remaining liquid guiding post 111 may be further reused.

Figure 1B:
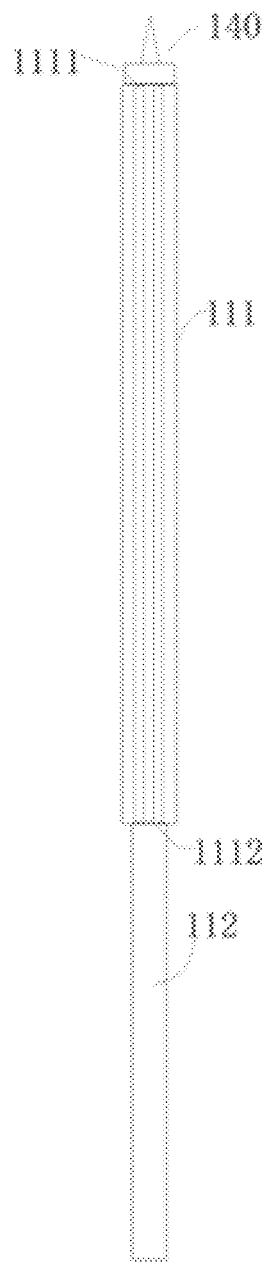
FIG. 1(b) is another structural schematic view of an introduction needle according to an embodiment of the present disclosure.
Figure 1C:
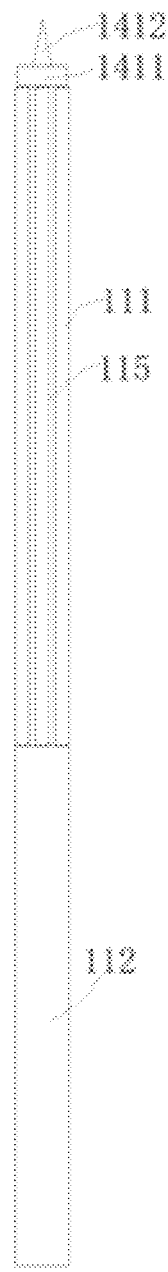
FIG. 1(c) is another structural schematic view of an introduction needle according to an embodiment of the present disclosure.
Figure 1D:
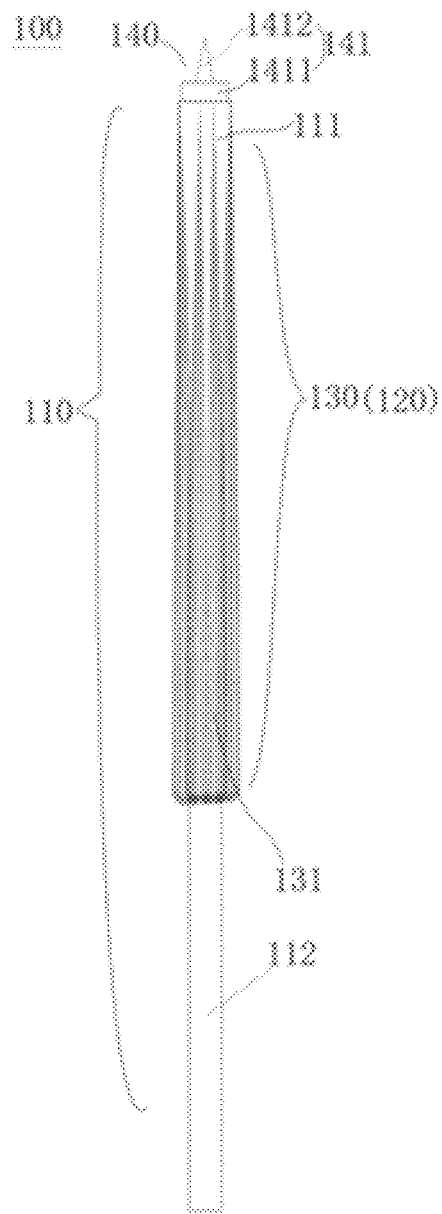
FIG. 1(d) is another structural schematic view of an introduction needle according to an embodiment of the present disclosure.

As shown in FIG. 1(a) to FIG. 1(c), in an embodiment, the liquid guiding post 111 of the present disclosure defines a plurality of channels 115. The plurality of channels 115 extend along the axial direction of the liquid guiding member 110 and are defined in the outer wall of the liquid guiding post 111 and/or at an interior of the liquid guiding post 111. The plurality of channels 115 cooperatively serve as the capillary liquid storage unit 120. The capillary liquid storage unit 120 is substantially configured to continuously supplying ink 300 to the tip of the needle tooth 1412. Therefore, at least one of the plurality of channels 115 temporarily stores the liquid, and the liquid in the at least one of the plurality of channels 115 may be guided by the gravitational force to flow to reach the needle tooth 1412 of the needle piercing portion 140. The plurality of channels 115 may be integrally defined in the outer wall of the liquid guiding member 110 by etching, cutting, engraving and grinding, or injection molding.

As shown in FIG. 1(*a*) to FIG. 1(*c*), in an embodiment, the plurality of channels 115 are arranged on the outer wall of the liquid guiding post 111. The plurality of channels 115 serve as the capillary liquid storage unit 120. The plurality of channels 115 in the present embodiment may be objects, such as a needle filament or a needle tube, that are connected to the liquid guiding post 111 and may form a gap.

As shown in FIG. 4(*a*) to FIG. 4(*b*), in an embodiment, the liquid guiding post 111 of the present disclosure may be formed by a plurality of needle filaments 113 having flat ends and/or a plurality of small posts 114. The plurality of needle filaments 113 having the flat ends and the plurality of small posts 114 are arranged adjacent to each other. Alternatively, the plurality of the needle filaments 113 having the flat ends are arranged adjacent to each other. Alternatively, the plurality of small posts 114 are arranged adjacent to each other. A gap between two adjacent needle filaments 113 having the flat ends serves as the channel 115 which serves as the capillary liquid storage unit 120. A gap between two adjacent small posts 114 serves as the channel 115 which serves as the capillary liquid storage unit 120. A gap between one needle filament 113 having the flat end and one small post 114 serves as the channel 115 which serves as the capillary liquid storage unit 120. The needle filament or the small post 114 in the present embodiment may be solid or hollow. The capillary may be formed by the gap, which is defined by splicing the needle filaments or the small posts 114. Alternatively, the needle filament or the small post 114 may be configured to be hollow to provide an auxiliary capillary.

In an embodiment, the channel (115) extends vertically or spirally from the first end face (1111) towards the second end face (1112). An end of the channel (115) may extend through or approach the second end face (1112). The channel (115) may extend vertically along the liquid guiding post (111) to reach the first end face (1111). The channel (115) may be an annular groove defined in the outer wall of the liquid guiding post (111), and a plurality of annular grooves are spaced apart from each other and are defined in the outer wall of the liquid guiding post (111).

Embodiment 6:

As shown in FIG. 1(*d*), the capillary liquid storage unit 120 in the present disclosure may be arranged by attaching a structure to an outside of the liquid guiding post. In the present embodiment, a liquid storage structure 130 is provided and includes one or more sheets. The sheets are attached to the outer wall of the liquid guiding post 111, and a gap is defined between the outer wall of the liquid guiding post 111 and the sheets. The gap serves as the capillary liquid storage unit 120. The capillary liquid storage unit 120 stores liquid temporarily. The liquid is guided to flow to the needle tooth 1412 of the needle piercing portion 140.

In an embodiment, the liquid storage structure 130 is formed by natural or man-made porous sheets.

In another embodiment, the liquid storage structure 130 includes a plurality of filaments. The plurality of filaments include fiber filaments 131. A gap between the plurality of fiber filaments 131 and a gap between the fiber filaments 131 and the outer wall of the liquid guiding post 111 serve as the capillary liquid storage unit 120. The capillary liquid storage unit 120 stores liquid temporarily. The liquid is guided to flow to the needle tooth 1412 of the needle piercing portion 140.

In an embodiment, the fiber filaments 131 may include animal hair, plant fiber filaments 131, chemical fiber filaments, and so on.

In an embodiment, the filaments may further include metal filaments. A gap between a plurality of metal filaments and a gap between the metal filaments and the outer wall of the liquid guiding member 110 serve as the capillary storage unit 120. The capillary storage unit 120 stores liquid temporarily, and the liquid is guided to flow to the needle tooth 1412 of the needle piercing portion 140.

In an embodiment, a position to which the liquid storage structure 130 is attached and area that the attached liquid storage structure 130 occupies may be determined based on a unit amount of ink stored in the liquid storage structure 130 and a target amount of stored ink of the liquid guiding member 110. Alternatively, the number of layers of the liquid storage structure 130 and the area of the liquid storage structure 130 may be determined based on the amount of ink used for tattoo.

Figure 17A:
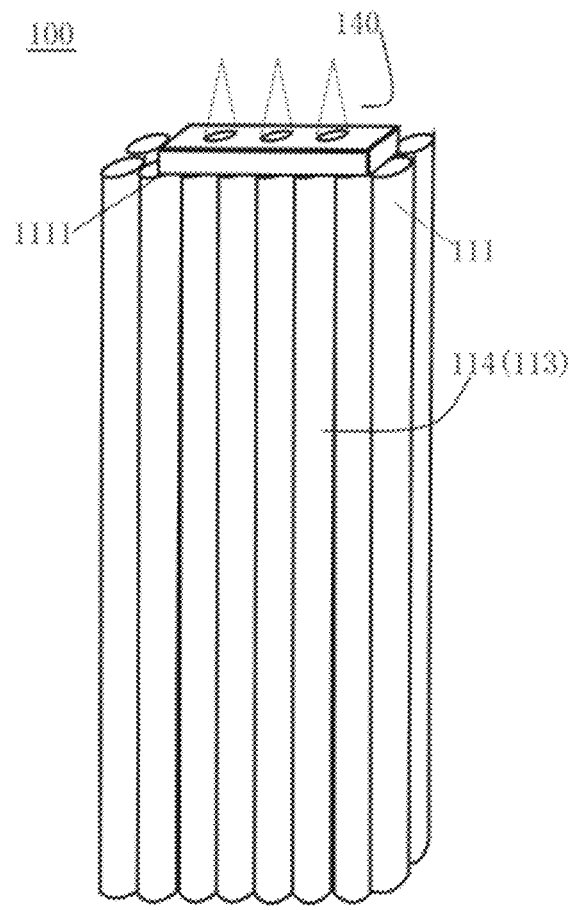
FIG. 17(a) is a perspective view of a portion of the introduction needle described according to an embodiment of the present disclosure.
Figure 17B:
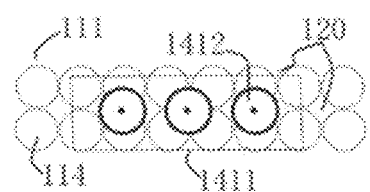
FIG. 17(b) is a planar schematic view of the introduction needle shown in FIG. 17(a), viewed from a viewing angle.
Figure 18A:
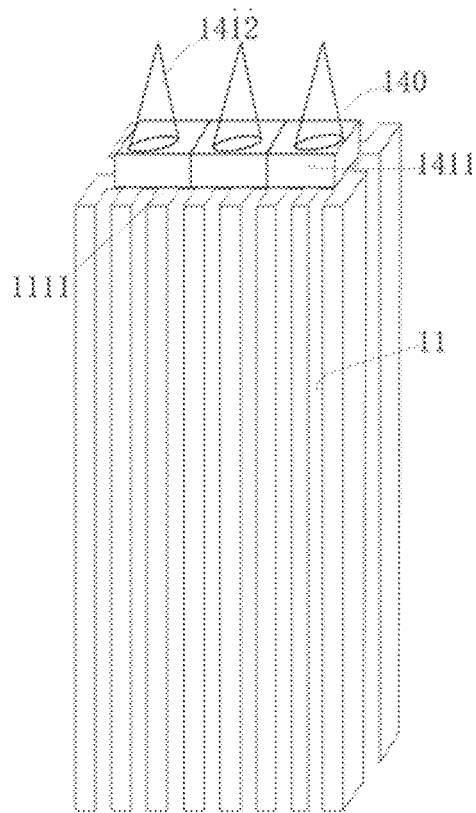
FIG. 18(a) is a perspective view of a portion of the introduction needle according to another embodiment of the present disclosure.
Figure 18B:
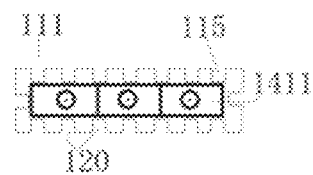
FIG. 18(b) is a planar schematic view of the introduction needle shown in FIG. 18(a), viewed from a viewing angle.

Embodiment 7:

The introduction needle provided in the present disclosure, serving as a tattoo tool, may introduce the tattoo ink 300 into the superficial layer of the skin. Therefore, a liquid guiding path may be formed between the ink 300 adsorbed into the liquid guiding member 110 and the needle tooth 1412 to ensure the ink 300 in the liquid guiding member 110 to flow to the tip of the needle tooth 1412 to be further introduced into the skin. Therefore, in the introduction needle of the present disclosure, one corner or one edge of at least one substrate 1411 of the piercing projection 141 needs to be disposed near the edge of the outer wall of the liquid guiding member 110. In this way, the needle tooth 1412 arranged on the substrate 1411 may receive the liquid flowing from the liquid guiding member 110. The above structure is necessary to effectively define the liquid guiding path to reduce the rate of empty needles. As shown in FIG. 4(*b*) and FIG. 4(*d*), the outer edge of the substrate 1411 of the piercing projection 141 has a portion that is substantially aligned with the outer edge of the liquid guiding post 111. The aligned portion ensures that the ink in the liquid guiding post 111 may flow to the tip of the needle tooth 1412. Similar structures are shown in FIG. 17(*a*) to FIG. 17(*b*) or FIG. 18(*a*) to FIG. 18(*b*).

In an embodiment, one corner or one edge of the substrate 1411 of the piercing projection 141 is substantially aligned with the edge of the outer wall of the liquid guiding member 110.

In another embodiment, the substrate 1411 of the piercing projection 141 is disposed at a middle of an end face of the liquid guiding member 110, and the corner or the edge of the substrate 1411 is no more than 0.18 mm away from the edge of the outer wall of the liquid guiding member 110.

Figure 8:
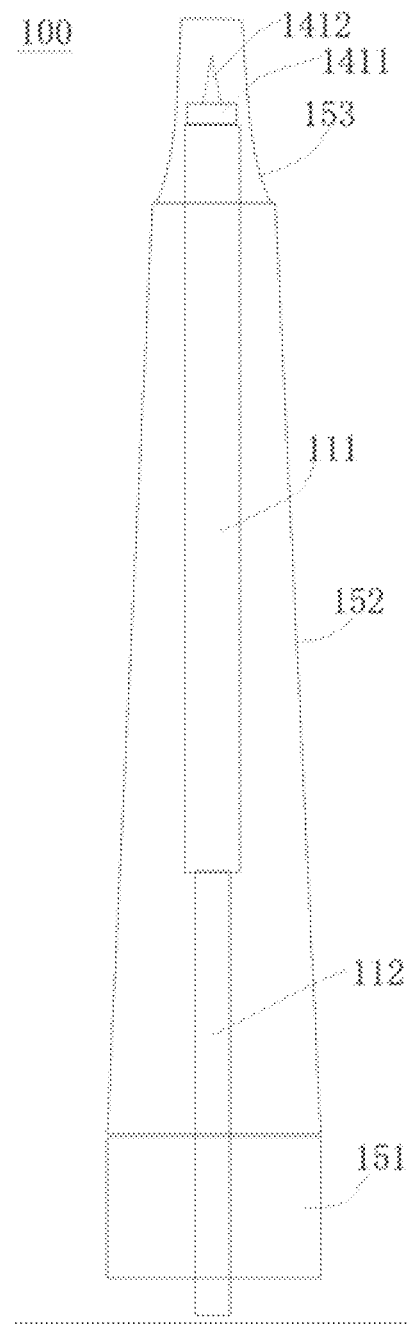
FIG. 8 is a schematic view of the introduction needle according to an embodiment of the present disclosure, wherein the introduction needle has a case.
Figure 9:
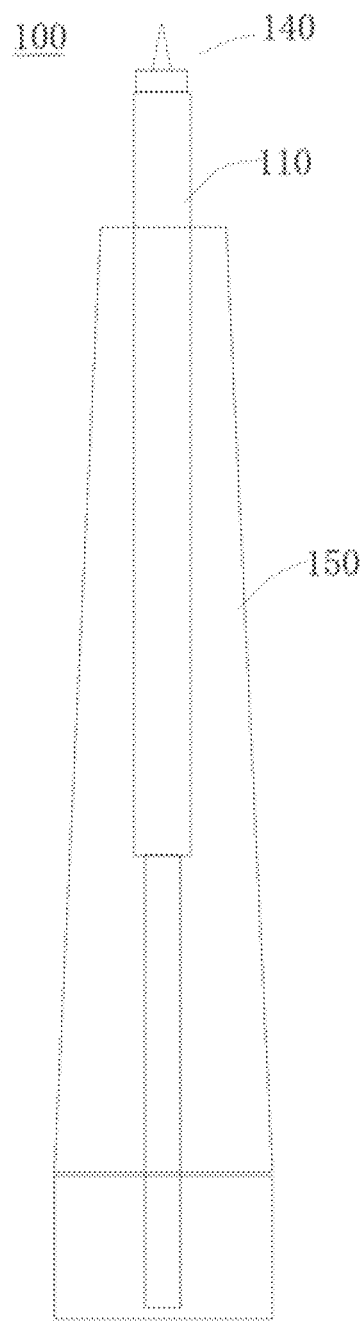
FIG. 9 is a schematic view of the structure shown in FIG. 8, wherein a needle outlet end of the case is omitted.
Figure 10:
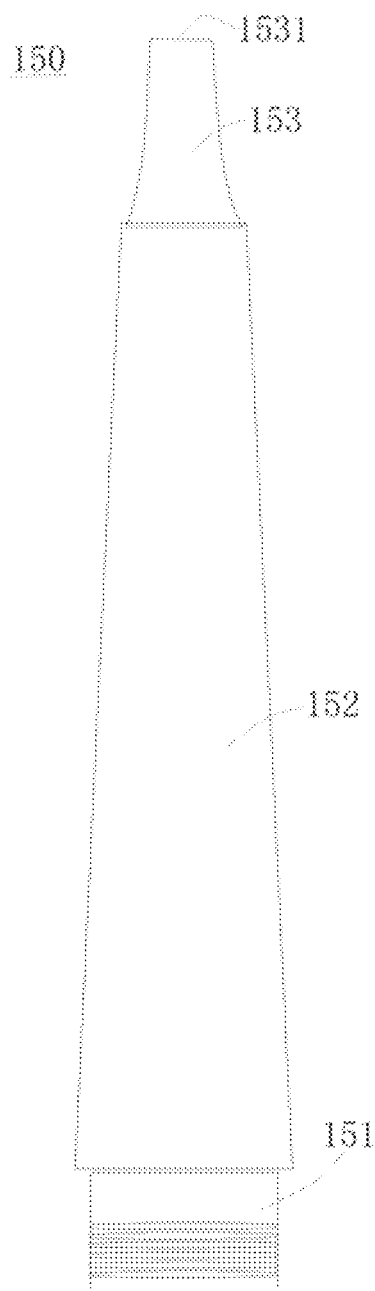
FIG. 10 is a schematic view of the case according to an embodiment of the present disclosure.

Embodiment 8:

As shown in FIG. 8 to FIG. 10, the introduction needle of the present disclosure may further be arranged with a case 150. The liquid guiding member 110 is arranged inside the case 150. The liquid guiding member 110 may move reciprocately inside the case 150 to achieve the piercing operations.

In an embodiment, the case 150 of the present disclosure may be a tubular cylinder. As shown in FIG. 10, the case 150 may have a fastening end 151, an intermediate connecting tube 152, and a needle outlet end 153. The fastening end 151, the intermediate connecting tube 152, and the needle outlet end 153 are connected to each other sequentially to define a channel for the liquid guiding member 110 to move reciprocactely. Each of a central axis of the fastening end 151 and a central axis of the intermediate connecting tube 152 coincides with a central axis of the case 150.

In an embodiment, the fastening end 151 of the present disclosure is detachably connectable to an external drive member (such that the introduction needle may be replaced easily). The needle outlet end 153 defines a needle outlet port 1531. The needle tooth 1412 moves reciprocately at a location near the needle outlet port 1531. The liquid guiding member 110 and the needle piercing portion 140 disposed at an end of the liquid guiding member 110 are mounted, along the central axis of the case 150, in the intermediate connecting tube 152 of the case 150. The needle piercing portion 140 is disposed near the needle outlet end 153. The liquid guiding member 110 moves reciprocately in the intermediate connecting tube 152. Further, the liquid guiding member 110 drives the needle tooth 1412 of the needle piercing portion 140 to move out of the needle outlet port 1531 or to move to be retracted into needle outlet port 1531. It will be understood that the needle tooth 1412 may alternatively be slightly retracted and disposed outside of the needle outlet port 1531.

In an embodiment, the needle outlet end 153 of the case 150 of the present disclosure may be tubular.

The needle outlet port 1531 may have a flat port or a sloped port.

In the case that the needle outlet port 1531 is the flat port, when the liquid guiding member 110 moves freely and reciprocately at the needle outlet port 1531 of the needle outlet end 153 of the case 150, a gap between the outer wall of the liquid guiding member 110 and an inner wall of the needle outlet end 153 serves as a combined capillary space. Liquid may be temporarily stored in the combined capillary space when the needle is intaking the liquid. The liquid temporarily stored in the combined capillary may be guided by the gravitational force to flow to the needle piercing portion 140 and may be introduced into the surface layer 200 of the skin while the needle tooth 1412 of the needle piercing portion 140 is piercing into the skin.

In the case that the needle outlet port 1531 is the sloped port, when the liquid guiding member 110 is moving freely and reciprocately at the needle outlet port 1531 at the needle outlet end 153 of the case 150, a gap between the outer wall of the liquid guiding member 110 and an inner wall of the sloped port serves as a combined capillary space. Liquid is temporarily stored in the combined capillary space when the needle is intaking the liquid. The liquid temporarily stored in the combined capillary space is guided to flow to the needle piercing portion 140 and is introduced into the surface layer of the skin while the needle tooth 1412 of the needle piercing portion 140 is piercing the skin. The outer wall of the liquid guiding member 110 may abut against the inner wall of the sloped port. In this case, the sloped port serves as a limiting plate for the liquid guiding post, allowing the liquid guiding post to be vertically piercing into the skin surface layer. In an embodiment, an angle may be formed between the central axis of the case and a plane in which the plate of the sloped port is located. When the liquid guiding member is moving, the sloped port may provide abutting for the liquid guiding member.

Embodiment 9:

While performing tattoo, the introduction needle is operating at a relatively high frequency. Therefore, while the needle is piercing the skin, the needle may be deviated and skewed, resulting in needle slippage. Therefore, the present disclosure provides an introduction needle to limit the liquid guiding member 110, assisting the liquid guiding member 110 to pierce into and leave out of the skin in a straight direction, and the piercing may be accurately performed.

Figure 11A:
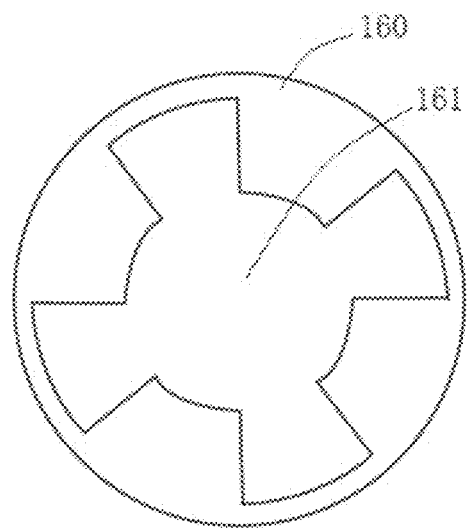
FIG. 11(a) is a cross-sectional view of a limiting structure according to an embodiment of the present disclosure, wherein the limiting structure is a knurled limiting hole.
Figure 11B:
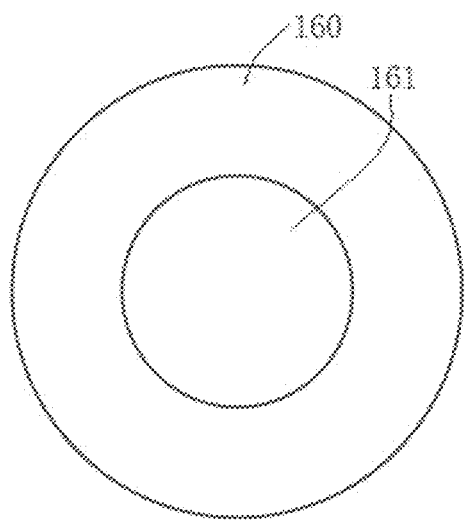
FIG. 11(b) is a cross-sectional view of a limiting structure according to another embodiment of the present disclosure, wherein the limiting structure is a circular limiting hole.

As shown in FIG. 12(*a*) to FIG. 12(*d*), FIG. 11(*a*), and FIG. 11(*b*), a limiting structure 160 is arranged inside the case 150 of the introduction needle in the present embodiment. The limiting structure 160 is disposed inside the intermediate connecting tube 152 of the case 150 and/or on the fastening end 151 of the case 150 and/or on the needle outlet end 153 of the case 150. When the liquid guiding member 110 is moving reciprocately along the central axis of the case 150, the liquid guiding member 110 may abut against the limiting structure 160. The limiting structure 160 limits the liquid guiding member 110 from swinging in a direction along a cross section of the case 150. In this way, the liquid guiding member 110 drives the needle tooth 1412 of the needle piercing portion 140 to vertically move out of the case 150 to pierce into the skin surface 200. Further, the liquid guiding member 110 drives the needle tooth 1412 of the needle piercing portion 140 to vertically move from the outside of the needle outlet port 1531 to the inside of the case 150. It will be understood that the needle tooth 1412 may alternatively be slightly retracted and still located outside the case 150.

In an embodiment, the limiting structure 160 of the present disclosure may be a limiting hole 161. The limiting hole 161 may be a through hole. A central axis of the through hole may or may not coincide with the central axis of the liquid guiding member 110. Preferably, the central axis of the through hole does not coincide with the central axis of the liquid guiding member 110. An inner diameter of the through hole may be adapted to an outer diameter of the liquid guiding member 110. For example, a shape and a size of the central through hole may be adapted to a shape and a size of the largest cross section of the liquid guiding member 110. The adaptation in this case may not refer to the shape and the size of the through hole being identical to the shape and the size of the largest cross section of the liquid guiding member, but allows the liquid guiding member to pass through the through hole. In an embodiment, a cylindrical liquid guiding member may be adapted with a square through hole. In this case, a gap between the cylindrical liquid guiding member and the square through hole may provide the capillary effect to store the liquid, ensuring the liquid guiding member 110 to move straight in the central through hole (the limiting structure provides abutting to the liquid guiding member to limit the liquid guiding member from swinging in a lateral direction and to ensure the liquid guiding member to move straight in central through hole). In this way, the central through hole limits a position of the liquid guiding member 110. The central through hole may be circular or irregularly shaped. As shown in FIG. 11(*a*), when the through hole is irregularly shaped, the through hole may be suitable for various shapes of liquid guiding members.

Figure 25:
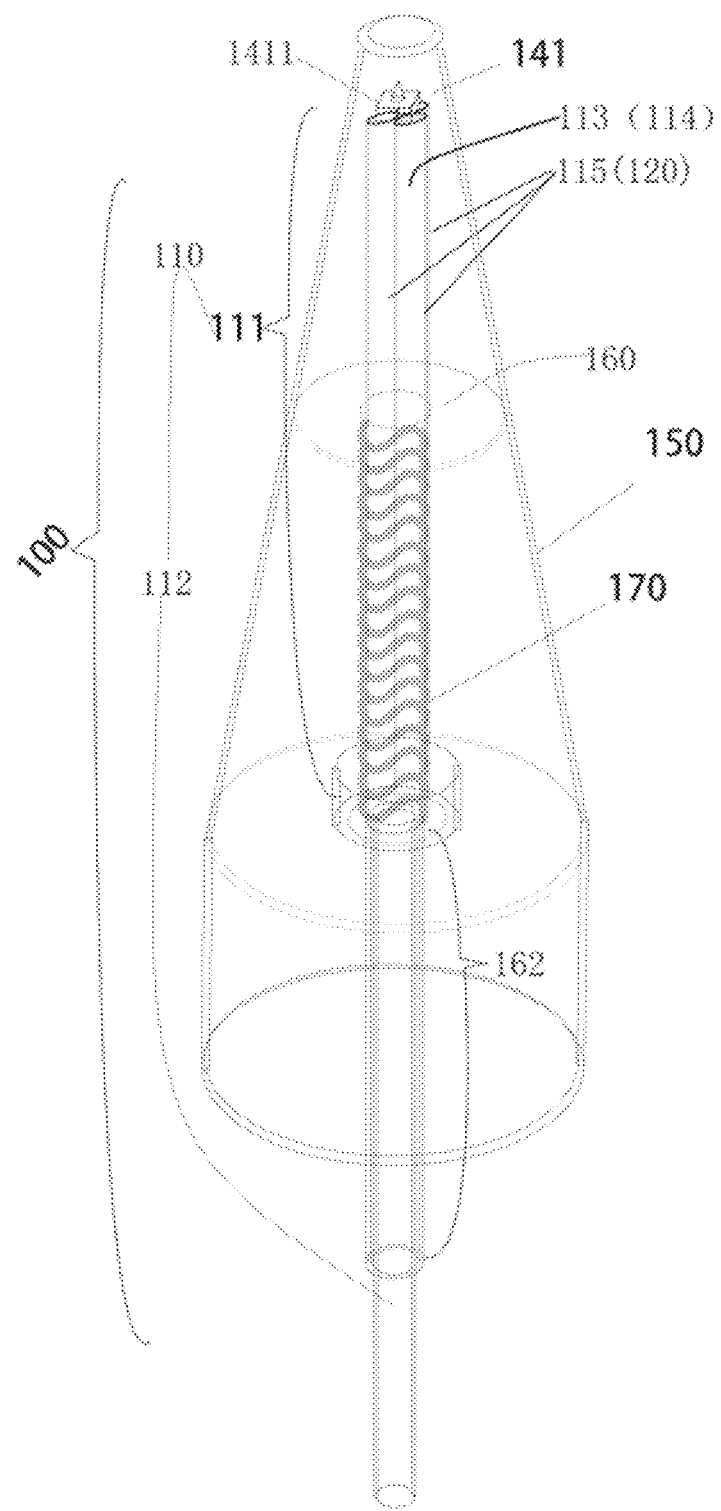
FIG. 25 is a structural schematic view of the introduction needle according to an embodiment of the present disclosure.

In an embodiment, as shown in FIG. 25, the limiting structure 160 of the present disclosure may be a limiting tube 162. The limiting tube 162 has a channel. A central axis of the channel may or may not coincide with the central axis of the liquid guiding member 110. An inner diameter of the channel is adapted to the outer diameter of the liquid guiding member 110. A shape and a size of the channel are adapted to the shape and the size of the largest cross section of the liquid guiding member 110. The adaptation in this case may not refer to the shape and the size of the channel being identical to the shape and the size of the largest cross section of the liquid guiding member, but allows the liquid guiding member to pass through the channel. In an embodiment, the cylindrical liquid guiding member may be adapted with a square channel. In this case, a gap between the cylindrical liquid guiding member and the square channel may provide the capillary effect to store the liquid, ensuring the liquid guiding member 110 to move straight in the central channel. The central channel limits the position of the liquid guiding member 110.

Figure 12A:
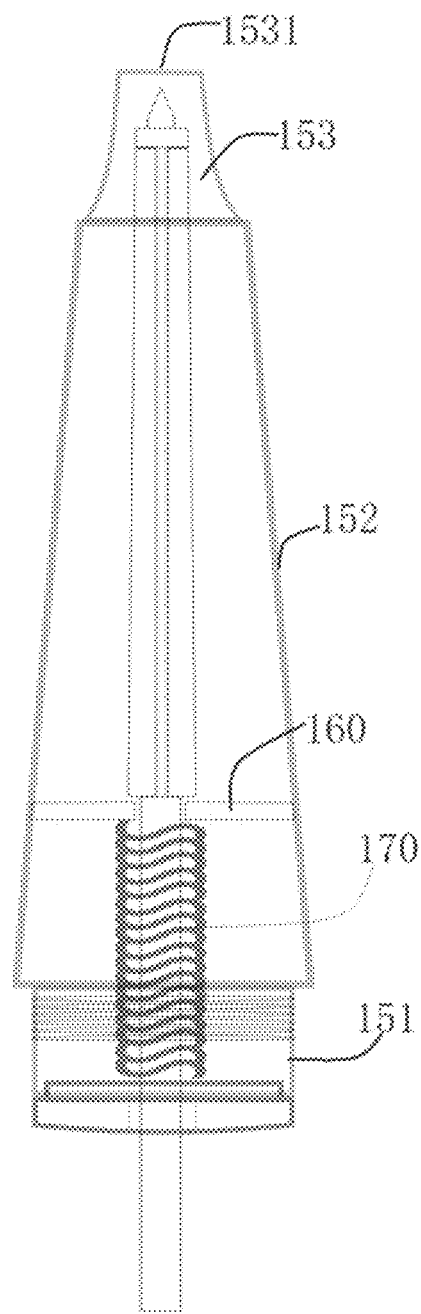
FIG. 12(a) is a structural schematic view of the introduction needle according to an embodiment of the present disclosure.
Figure 12B:
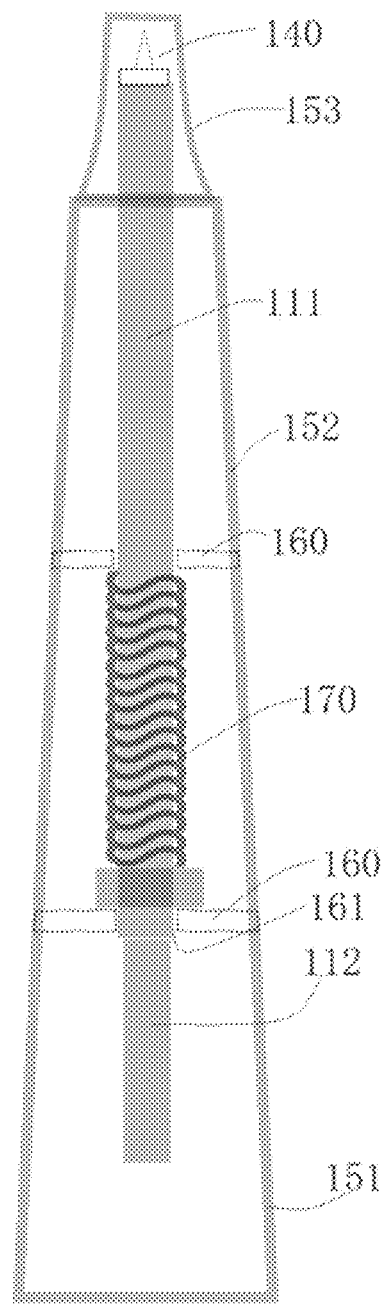
FIG. 12(b) is another structural schematic view of the introduction needle according to an embodiment of the present disclosure.
Figure 12C:
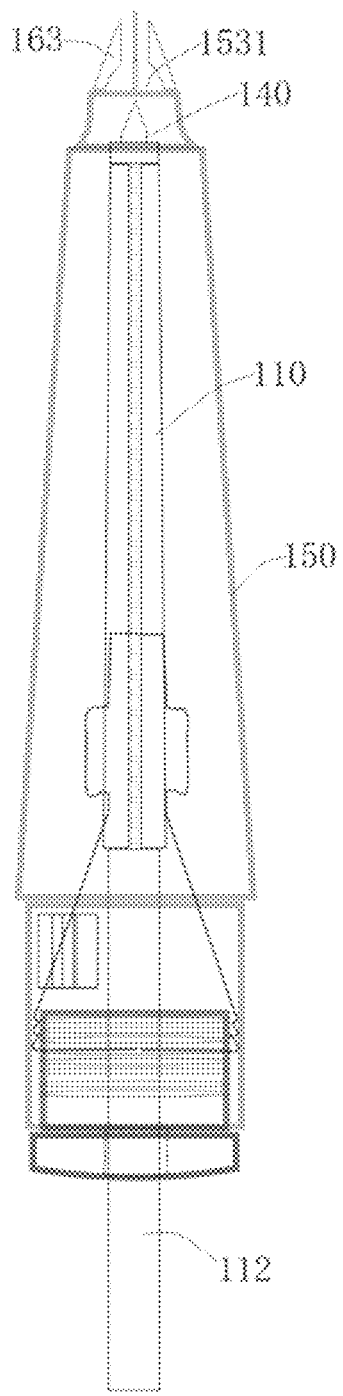
FIG. 12(c) is another structural schematic view of the introduction needle according to an embodiment of the present disclosure.
Figure 12D:
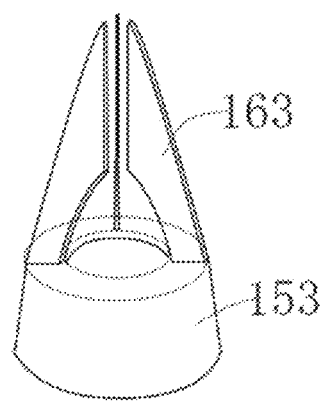
FIG. 12(d) is a perspective view of a needle outlet end of the introduction needle shown in FIG. 12(c).
Figure 12E:
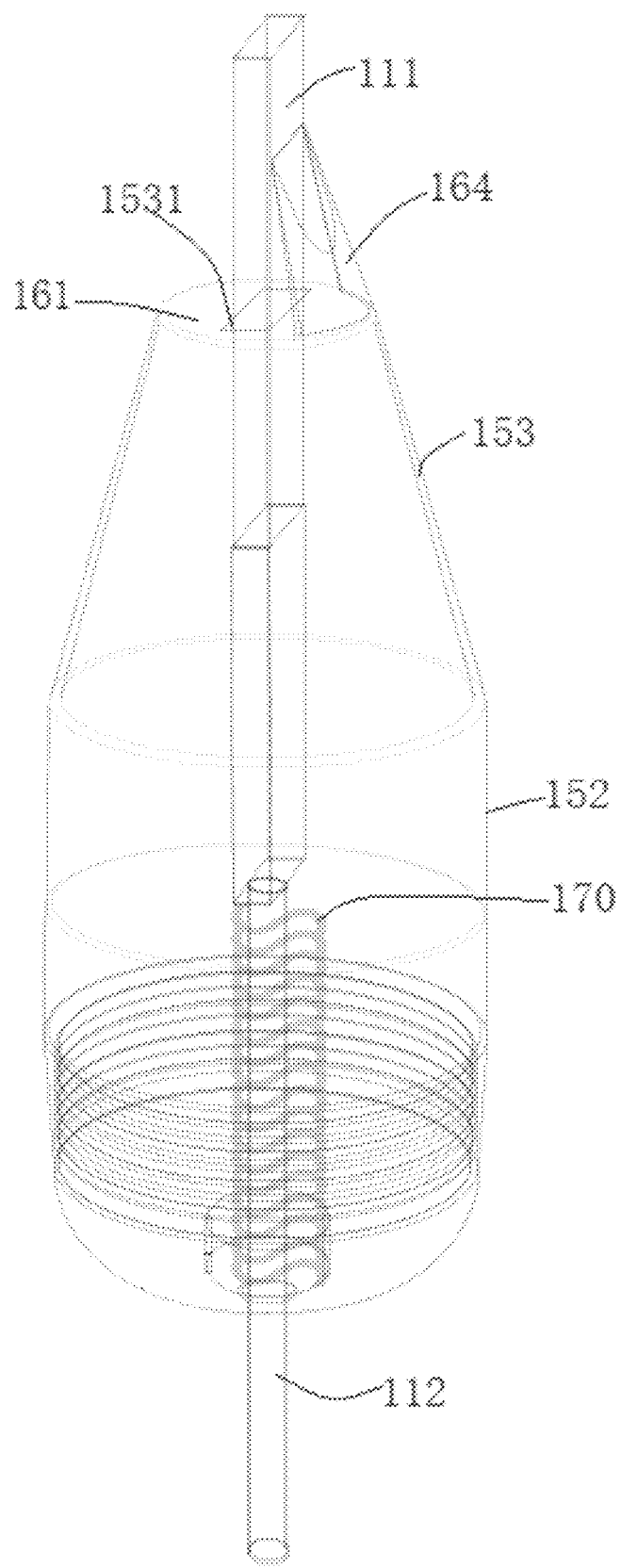
FIG. 12(e) is a structural schematic view of the introduction needle according to an embodiment of the present disclosure.
Figure 13A:
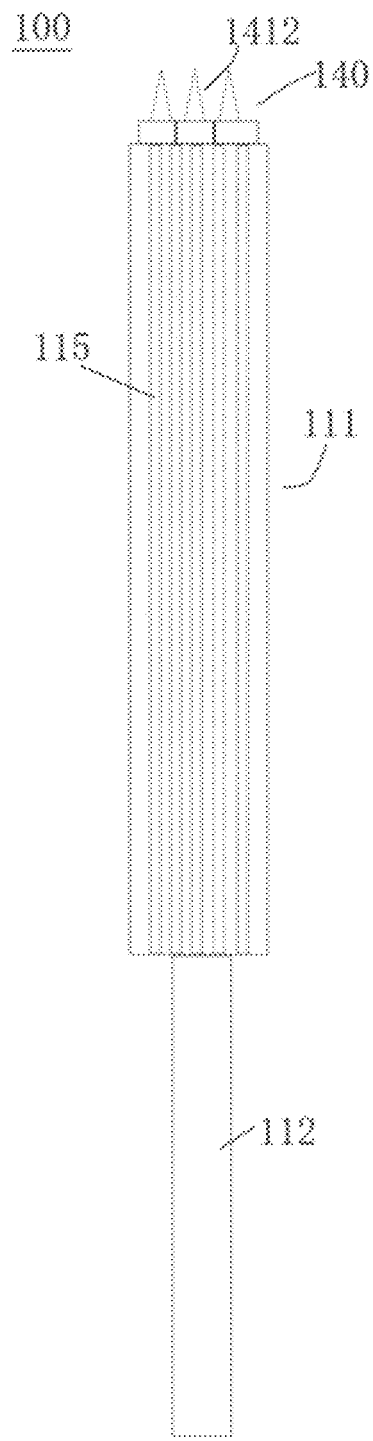
FIG. 13(a) is a structural schematic view of the introduction needle according to an embodiment of the present disclosure.
Figure 13B:
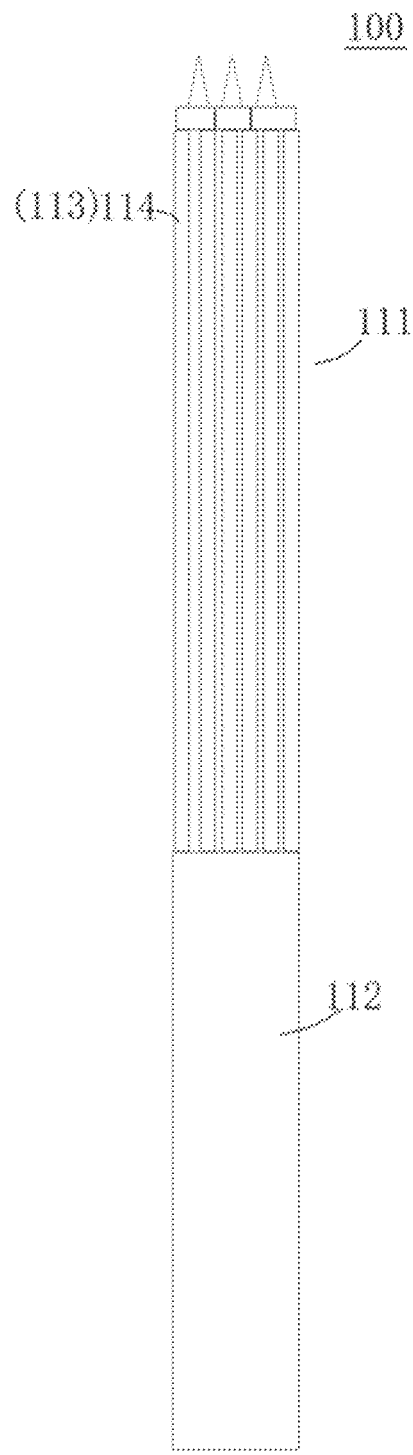
FIG. 13(b) is another structural schematic view of the introduction needle according to an embodiment of the present disclosure.
Figure 13C:
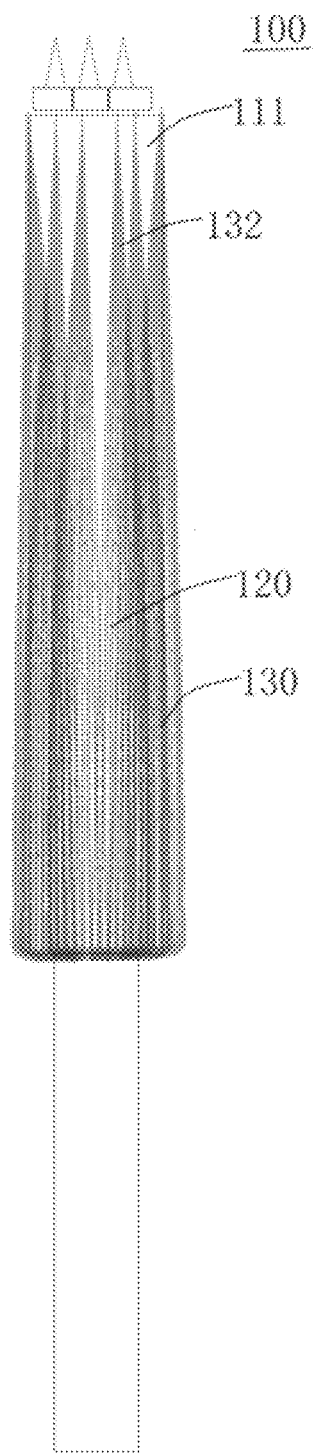
FIG. 13(c) is another structural schematic view of the introduction needle according to an embodiment of the present disclosure.
Figure 14A:
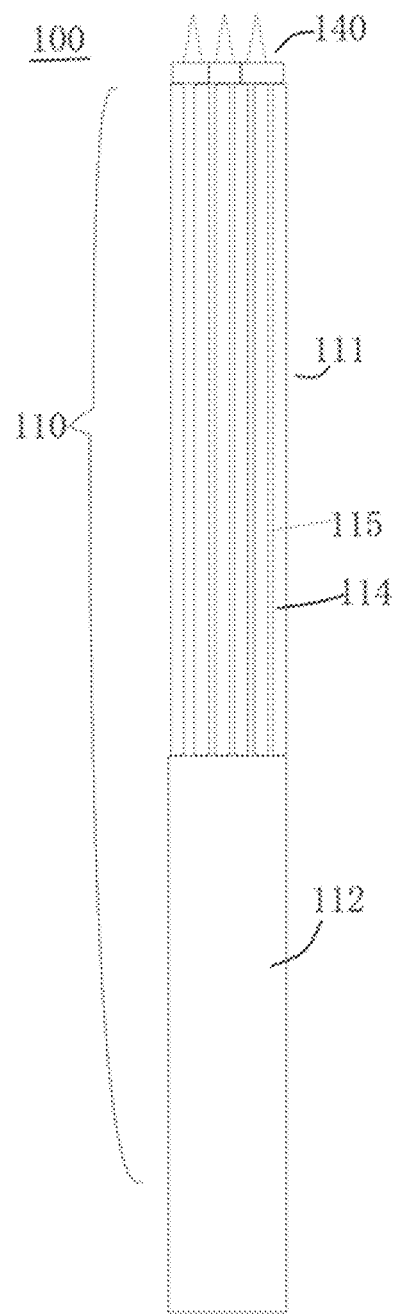
FIG. 14(a) is a structural schematic diagram of the introduction needle according to another embodiment of the present disclosure.
Figure 14B:
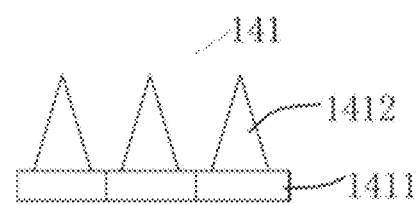
FIG. 14(b) is a planar schematic diagram of a piercing projection of a needle piercing portion according to an embodiment of the present disclosure.
Figure 14C:
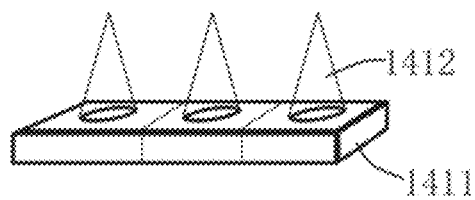
FIG. 14(c) is a perspective view of the piercing projection shown in FIG. 14(b).
Figure 15A:
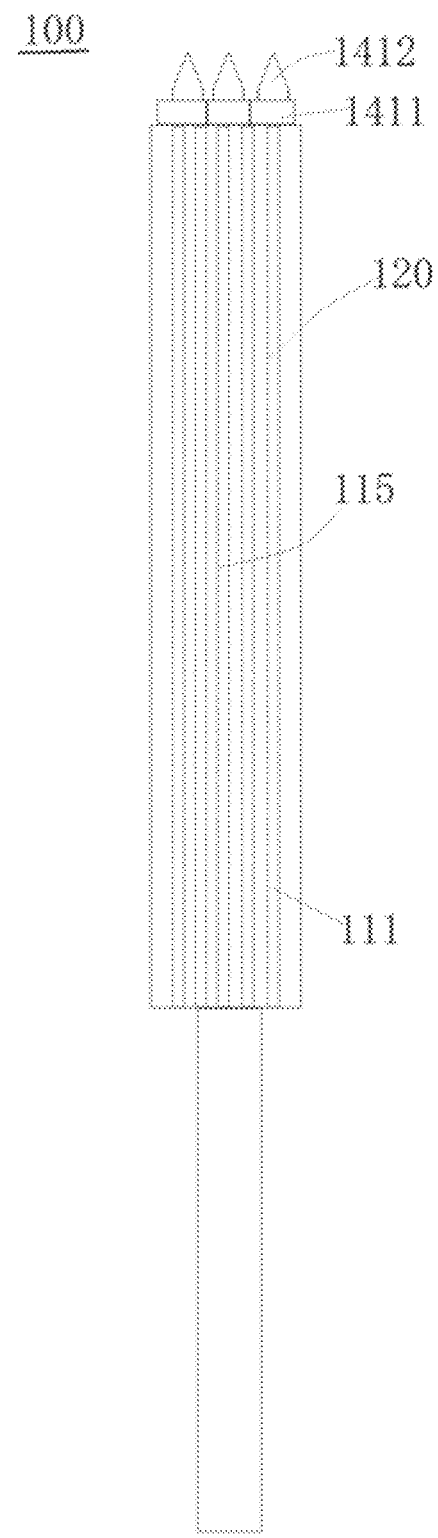
FIG. 15(a) is a structural schematic view of an introduction needle according to still another embodiment of the present disclosure.
Figure 15B:
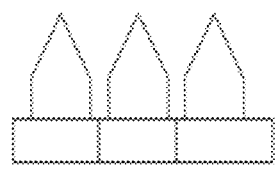
FIG. 15(b) is a planar schematic diagram of a piercing projection of a needle piercing portion according to an embodiment of the present disclosure.
Figure 15C:
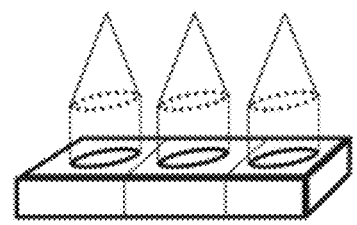
FIG. 15(c) is a perspective view of the piercing projection shown in FIG. 15(b).

In an embodiment, as shown in FIG. 12(e), the limiting structure 160 of the present disclosure may be a limiting plate 164. The limiting plate 164 has a limiting surface. An angle is generated between a plane in which the limiting surface is located and the central axis of the liquid guiding member 110. In one case, the plane in which the limiting surface is located may be parallel to the central axis of the liquid guiding member 110. When the liquid guiding member 110 is moving reciprocately along the central axis of the case 150, the liquid guiding member 110 abuts against the limiting surface. The limiting surface limits the liquid guiding member 110 from swinging in the direction of the cross section of the case 150. The limiting plate 164 of the present disclosure may be disposed at the needle outlet port 1531 of the needle outlet end 153 of the case 150. One or more limiting structures 164 may be arranged. When more than one limiting structures 164 are arranged, the more than one limiting structures 164 may be evenly distributed at the needle outlet port 1531 to define a channel, and the needle piercing portion 140 may move straight in and out of the channel.

As shown in FIG. 12(c) and FIG. 12(d), in an embodiment, the limiting structure 160 of the present disclosure may be a limiting bracket 163. The limiting bracket 163 is disposed at an end of the case 150 (or disposed inside the case). The limiting bracket 163 includes one or more sub-brackets. For each of the one or more sub-brackets, a side of the sub-bracket abuts against the liquid guiding member 110. The sub-brackets limit the liquid guiding member 110 from swinging in the direction of the cross section of the case 150. When the liquid guiding member 110 moves reciprocately along the central axis of the case 150, the liquid guiding member 110 abuts against a side of the sub-bracket. Further, due to abutting against the side of the sub-bracket, the liquid guiding member 110 is guided to move to the needle outlet port 1531 of the case 150.

The limiting structure 160 in the present embodiment may effectively limit and guide the liquid guiding member 110, ensuring the needle to pierce the skin at desired position accurately and preventing the needle from being skewed or from slipping.

Embodiment 10:

As shown in FIG. 12(a) to FIG. 12(c), the introduction needle 100 in the present embodiment may further include an elastic member 170, such as a spring, a silicone member, or a rubber band. An end of the elastic member 170 is connected to the case 150, and the other end of the elastic member 170 is connected to the connecting rod of the liquid guiding member 110. The elastic member may be connected to the case or the liquid guiding member in various ways, such as connection by abutting, encased connection, or connection by hooks, and so on. The case 150 is connected to the motorized rod. When the liquid guiding member 110 is driven by an external force (a motor of the motorized rod is activated to apply a driving force to the liquid guiding member 110) to move along the central axis of the case 150 towards the needle outlet port 1531 of the case 150, the elastic member 170 is elastically deformed to drive the liquid guiding member 110 to move back to its initial position.

Figure 16:
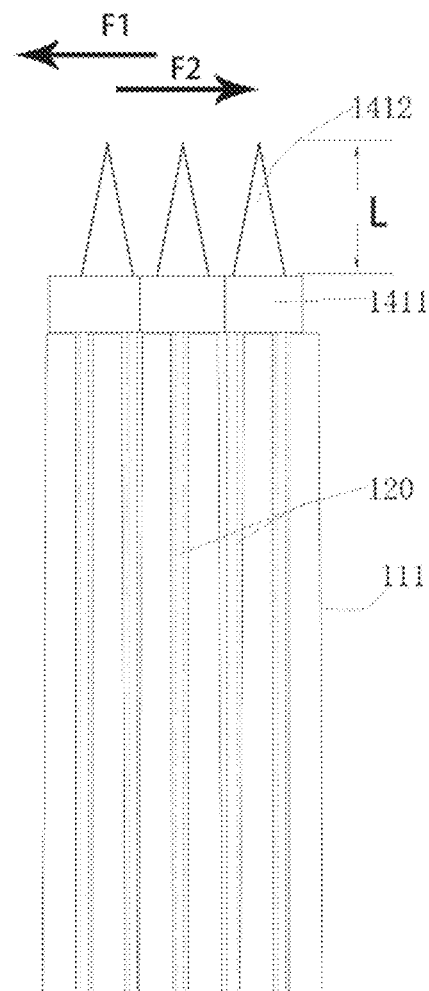
FIG. 16 is a structural schematic view of a liquid guiding post and a piercing projection according to an embodiment of the present disclosure.

Embodiment 11:

Different tattoo patterns and tattoo locations may require different tattoo needles to be used. The present disclosure further provides an introduction needle 100, and the piercing projection 141 of the introduction needle includes one or more substrates 1411. One needle tooth 1412 is arranged on each of the one or more substrates 1411. The one or more substrates 1411 are arranged into one row, and therefore, the corresponding needle teeth 1412 arranged on the corresponding one or more substrates 1411 are also arranged into one row, such as shown in FIG. 16.

As shown in FIG. 13(a) to FIG. 13(c), FIG. 14(a) to FIG. 14(c), and FIG. 15(a) to FIG. 15(c), for one introduction needle, more than one needle teeth are arranged in a row. This type of introduction needle may be configured to produce a tattoo having a relatively long linear pattern and a small transition arc. Compared to the introduction needle having a single needle tooth, the introduction needle having more than one needle teeth in the present embodiment may produce specific patterns more quickly. Of course, in order to produce a tattoo having dots or having large transition arcs between linear patterns, the introduction needle having the single needle tooth may be more advantageous.

Figure 19:
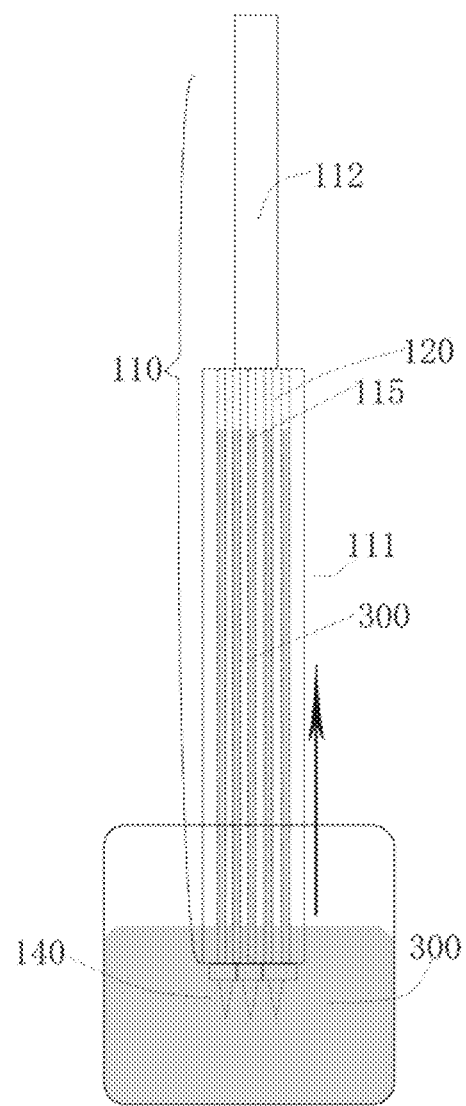
FIG. 19 is a schematic view showing a state of the introduction needle while the introduction needle is intaking ink, according to an embodiment of the present disclosure.
Figure 20:
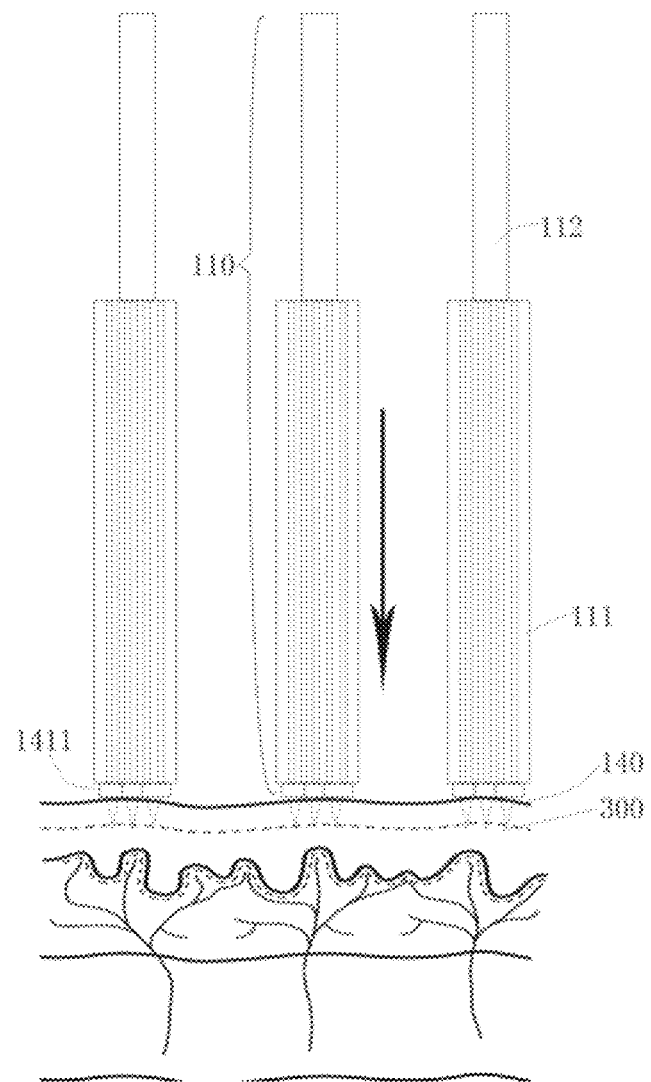
FIG. 20 is a schematic view showing a state of the introduction needle piercing into the skin, according to an embodiment of the present disclosure.

As shown in FIG. 19 and FIG. 20, FIG. 19 is a schematic view showing an in-use state of the introduction needle while intaking the ink. The needle piercing portion in the drawings has a plurality of substrates and a plurality of needle teeth. The ink in an ink bottle is adsorbed into the capillary liquid storage unit 120 from the end of the liquid guiding member. Further as shown in FIG. 20, when the introduction needle is being used to pierce into the skin, each of the plurality of substrates 1411 of the needle piercing portion 140 limits a depth that a corresponding one of the plurality of needle teeth 1412 pierces into the skin. As shown in the drawings, the plurality of needle teeth pierce into the skin at the same time. Such an arrangement of the substrates and the needle teeth allows the needle piercing portion to be more suitable for drawing lines.

Figure 21A:
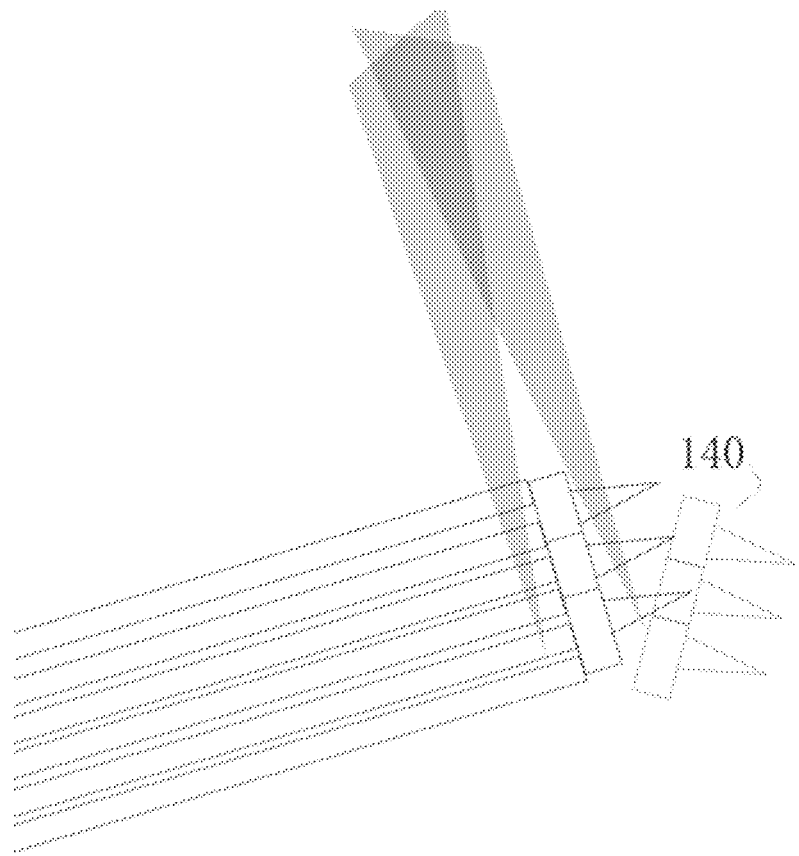
FIG. 21(a) is a schematic view showing a state of destroying an introduction needle after being used according to an embodiment of the present disclosure.
Figure 21B:
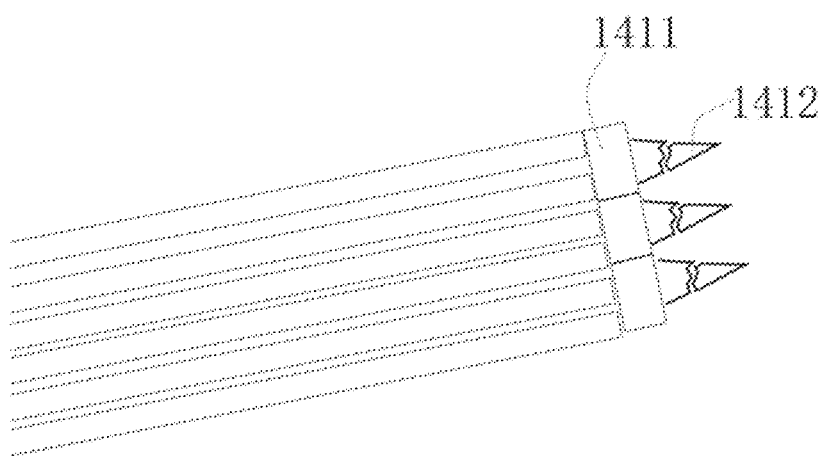
FIG. 21(b) is a schematic view showing a state of destroying an introduction needle after being used according to another embodiment of the present disclosure.

As shown in FIG. 21(a) and FIG. 21(b), the needle piercing portion having a single row of the plurality of needle teeth may also be destroyed simply.

Embodiment 12:

Based on the introduction needle of the present embodiment, the present disclosure further provides a tattoo device. The tattoo device includes any one of the above-mentioned introduction needles 100 and an external drive member that drives the liquid guiding member 110 of the introduction needle 100 to move.

In an embodiment, the external drive member includes a manual rod, a motorized rod, and an intelligent arm.

The present disclosure further provides a tattoo needle as shown in FIG. 26 to FIG. 45.

In order to colour the skin by block, by strip and by dot, the tattoo device in the art mainly takes a single row of metal needle filaments having sharpened tips as operating ends. Further, the single row of needle filaments is welded to a needle handle and are fixed to the tattoo rod through a fixed end of the needle handle. In this way, a device having a row of needles is formed. Usually, the device having a row of needles is used perform following three types of colouring methods. For a method 1, the device streaks a line to colour the skin. That is, the single row of needle filaments forms a longitudinal column, the row of needle filaments breaks the skin successively and repeatedly streak the broken skin, such that a coloured strip is obtained. For a method 2, the device sweeps the skin to colour the skin. That is, the single row of needle filaments are arranged into a horizontal column and move at the same time side-by-side. The single row of needle filaments repeatedly sweep the broken skin, such that a coloured block is obtained. For a method 3, the device pricks the skin at a dot to colour the skin. That is, the single row of needle filaments vertically face the skin, front ends of the needle filaments form a straight line parallel to the skin and repeatedly move up and down to pierce the skin, such that a row of coloured dots are obtained.

However, the above device having a row of needles has poor ink absorption and storage capacity. The device cannot be supplied with the ink for a long time. Therefore, a high rate of empty needles may be caused. Further, elastic vibration between adjacent needle filaments may be caused, resulting in colour pigments being sprayed around and a poor colouring effect.

Figure 26:
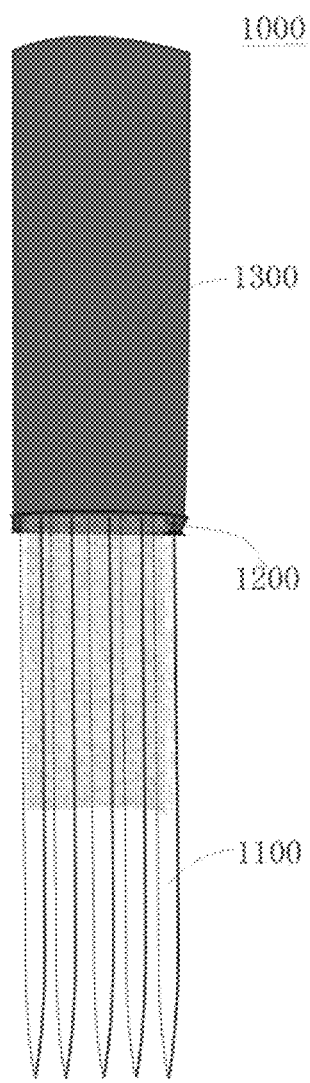
FIG. 26 is a schematic view of a device, in the art, having multiple needles arranged in a row.

As shown in FIG. 26 to FIG. 31, schematic views of the device having a row of needles in the art being used in various application scenarios are shown. The drawings show a device 1000 having a row of needles, metal needle filaments 1100; a welding zone 1200; a fixed end 1300; and a skin 2000. As shown in FIG. 26, the device 1000 having a row of needles in the art is shown and includes a plurality of metal needle filaments 1100 and the fixed end 1300 fixed to the tattoo rod.

Each of the plurality of metal needle filaments 1100 has a sharpened end. The plurality of metal needle filaments 1100 are welded to the welding zone 1200 and are spaced apart from each other equidistantly. For the device 1000 having a row of needles in the art, a length of each needle tip exposed out of the welding zone is generally in a range of 3 mm-30 mm, which is much greater than the thickness of the epidermis of the human face. An average thickness of the epidermis of the human face is in a range of 0.2-1.0 mm.

Figure 27:
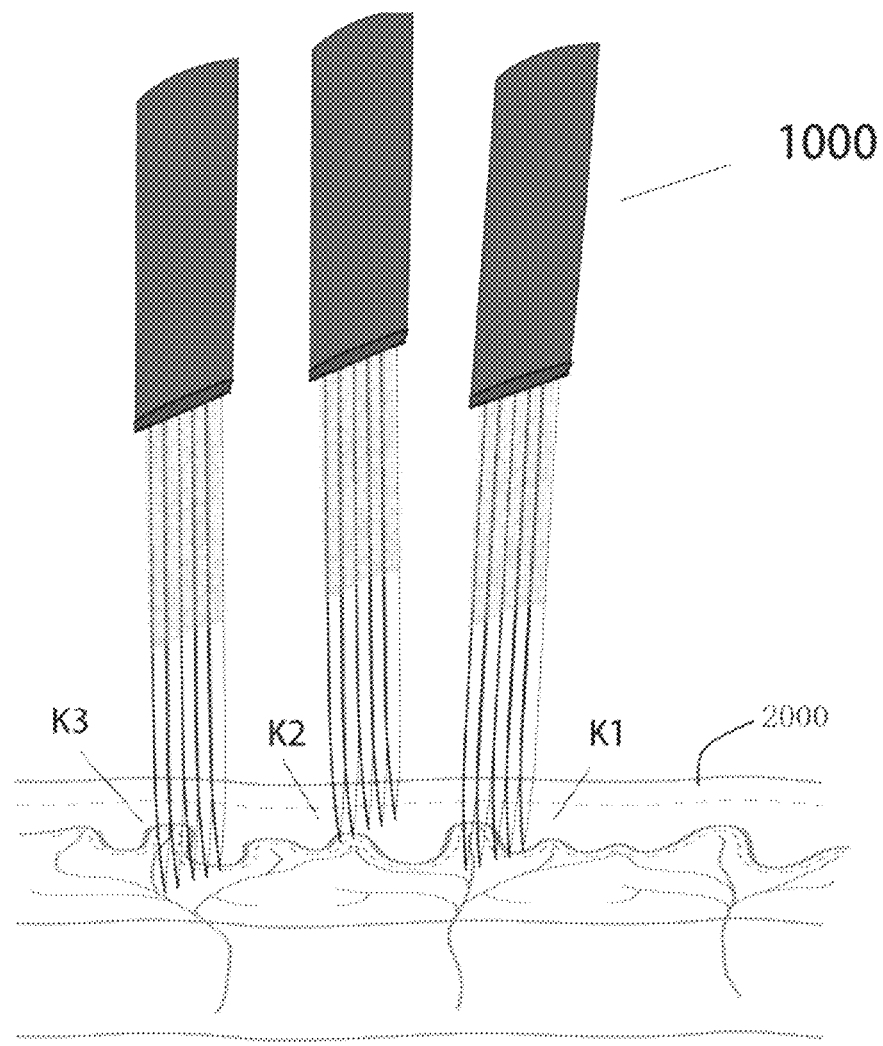
FIG. 27 is a schematic view of an in-use state of the device having multiple needles arranged in a row, as shown in FIG. 26, piercing into the skin.

As shown in FIG. 27, since a piercing depth into the skin is not determined, when the device 1000 having a row of needles is operating to apply colour to the epidermis 2000, the device may pierce to reach depths K1, K2, and K3 under the skin, where the depths K1, K2, and K3 are different from each other. Therefore, the skin may be colour unevenly or darker, or "colour fading" may be caused.

Figure 28:
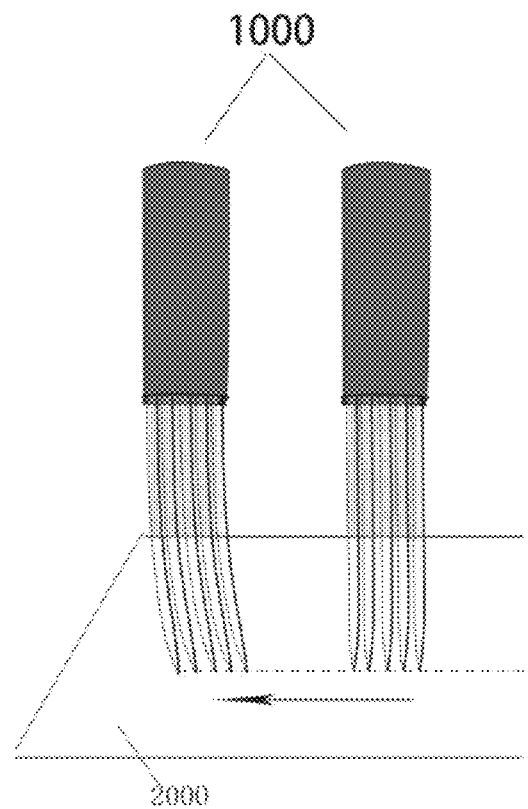
FIG. 28 is a schematic view of an in-use state of the device having multiple needles arranged in a row, as shown in FIG. 26, streaking lines to colour the skin.
Figure 29:
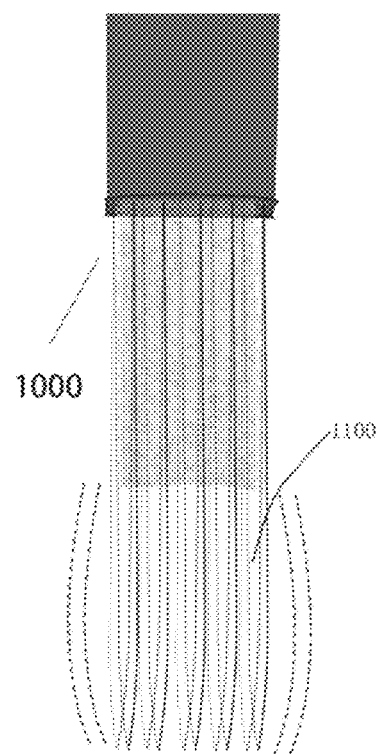
FIG. 29 is a schematic view of the device shown in FIG. 28 being elastically deformed after being used.

As shown in FIG. 28, when the device 1000 having a row of needles is streaking lines to colour the epidermis 2000, the single row of needle filaments forms a longitudinal column, successively break the skin in a direction indicated by arrows in FIG. 28, and repeatedly streak the skin. Further, when the device leaves the skin, as shown in FIG. 29, the needle filaments 1100 of the device 1000 may be elastically deformed. Therefore, the needle filaments may touch each other, resulting in the colouring pigments being splattered around.

Figure 30:
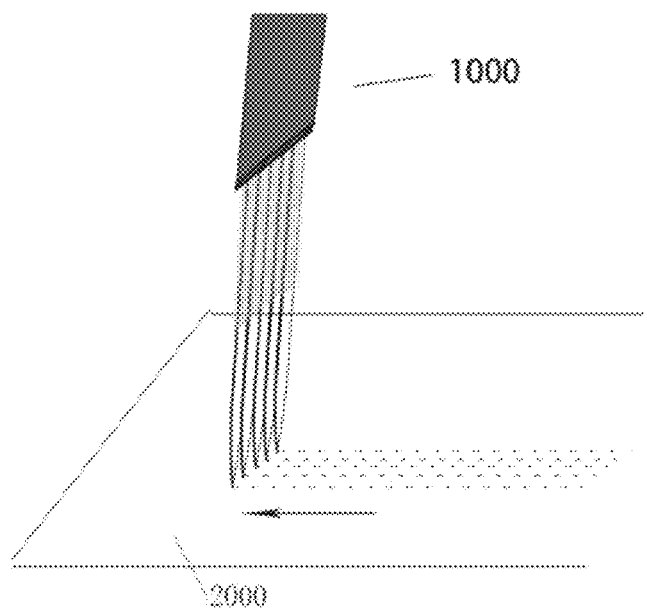
FIG. 30 is a schematic view of an in-use state of the device having multiple needles arranged in a row, as shown in FIG. 26, being used to regionally colour the skin.

As shown in FIG. 30, when the device 1000 having a row of needles does sweep to colour the epidermis 2000, the single row of needle filaments forms a horizontal column, move side-by-side at the same time in a direction indicated by arrows in FIG. 30, and repeatedly sweep the broken skin. In this case, spacings between every two adjacent needle filaments are required to be equal to each other, and the single row of needle filaments are required to pierce into the skin to reach the same depth, and only in this way, a coloured block having an even colour may be obtained.

Figure 31:
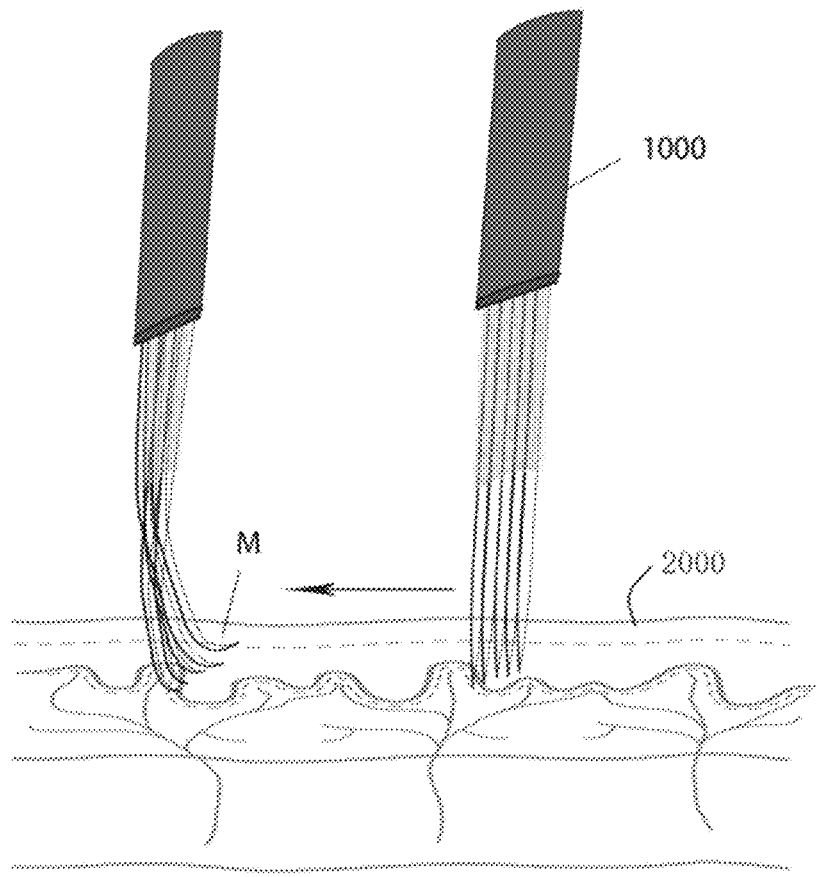
FIG. 31 is a schematic view of the device shown in FIG. 30 being elastically deformed after being used.

As shown in FIG. 31, the device 1000 having a row of needles pierces the skin and repeatedly sweeps to colour the skin. In this case, since stratum corneum of the skin has various thicknesses and toughnesses, the needle filaments of the device 1000 may be encountered by different resistance forces while moving in a direction indicated by arrows in FIG. 31. Therefore, tips M of the needle filaments may be bent to different extent, such that, when the needle filaments pierces into the skin again, spacings between adjacent needle filaments may be changed, and the needle filaments may pierce into the skin to reach different depths. Therefore, the skin may be damaged and may be coloured unevenly.

Therefore, in order to solve the deficiencies of the tattoo device in the art, the present disclosure provides a tattoo needle, which has a better colouring effect than the tattoo needle in the art.

Figure 32A:
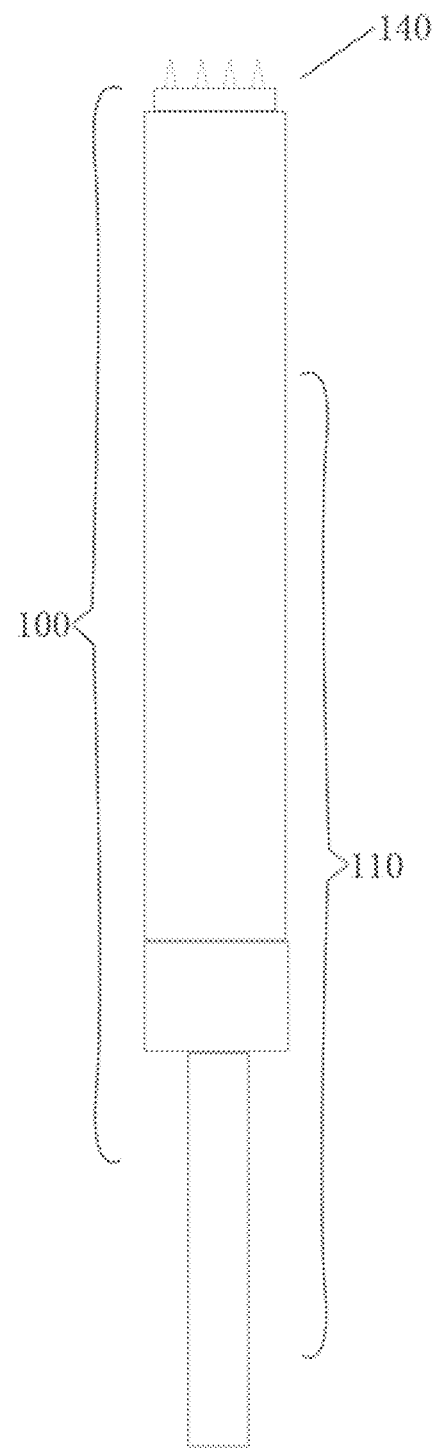
FIG. 32(a) is a structural schematic view of a tattoo needle according to an embodiment of the present disclosure.
Figure 32B:
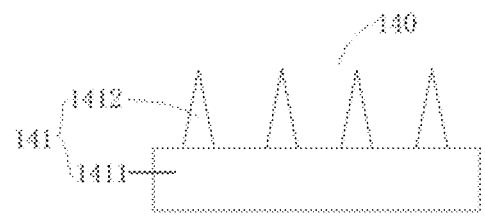
FIG. 32(b) is a structural schematic view of the needle piercing portion according to an embodiment of the present disclosure.
Figure 32C:
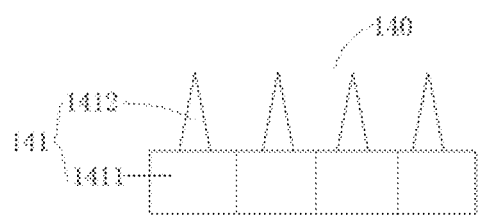
FIG. 32(c) is a structural schematic view of the needle piercing portion according to another embodiment of the present disclosure.

Embodiment 1:

FIG. 32(a) shows a tattoo needle 100 having a single row of needle filaments in which a piercing depth of the single row of needles piercing into the skin may be predefined accurately. The tattoo needle 100 includes a needle piercing portion 140 and a liquid guiding member 110. As shown in FIG. 32(b), in an embodiment, the needle piercing portion 140 includes a piercing projection 141. One piercing projection 141 includes four needle teeth 1412 and a substrate 1411. A length that each of four needle teeth 1412 pierces into the skin may be predefined. The four needle teeth 1412 are arranged on the substrate 1411. The substrate 1411 limits the piercing depth that the needle teeth 1412 can pierce into the skin. The substrate 1411 and the four needle teeth 1412 are configured as a one-piece and integral structure. As shown in FIG. 32(c), in another embodiment, the needle piercing portion 140 includes four piercing projections 141. Each of the four piercing projections 141 may include a needle tooth 1412 and a substrate 1411. A length that the needle tooth 1412 pierces into the skin may be predefined. The needle tooth 1412 is arranged on the substrate 1411. The substrate 1411 limits the piercing depth that the needle tooth 1412 can pierce into the skin. The substrate 1411 and the needle tooth 1412 are configured as a one-piece and integral structure.

Figure 32D:
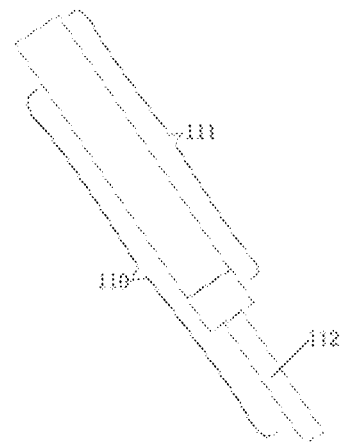
FIG. 32(d) is a structural schematic view of a liquid guiding member according to an embodiment of the present disclosure.

As shown in FIG. 32(d), the liquid guiding member 110 is a strip, including a liquid guiding post 111 and a connecting rod 112. The liquid guiding post 111 is a column, an upper portion and a lower portion of the liquid guiding post 111 are equal sized. The liquid guiding post 111 and the connecting rod 112 are connected and fixed with each other to form a one-piece component. The liquid guiding post 111 is fixedly connected to the piercing projection 141. The connecting rod 112 is connected to the tattooing rod for operation. An operator may directly hold the connecting rod for operation.

Figure 33:
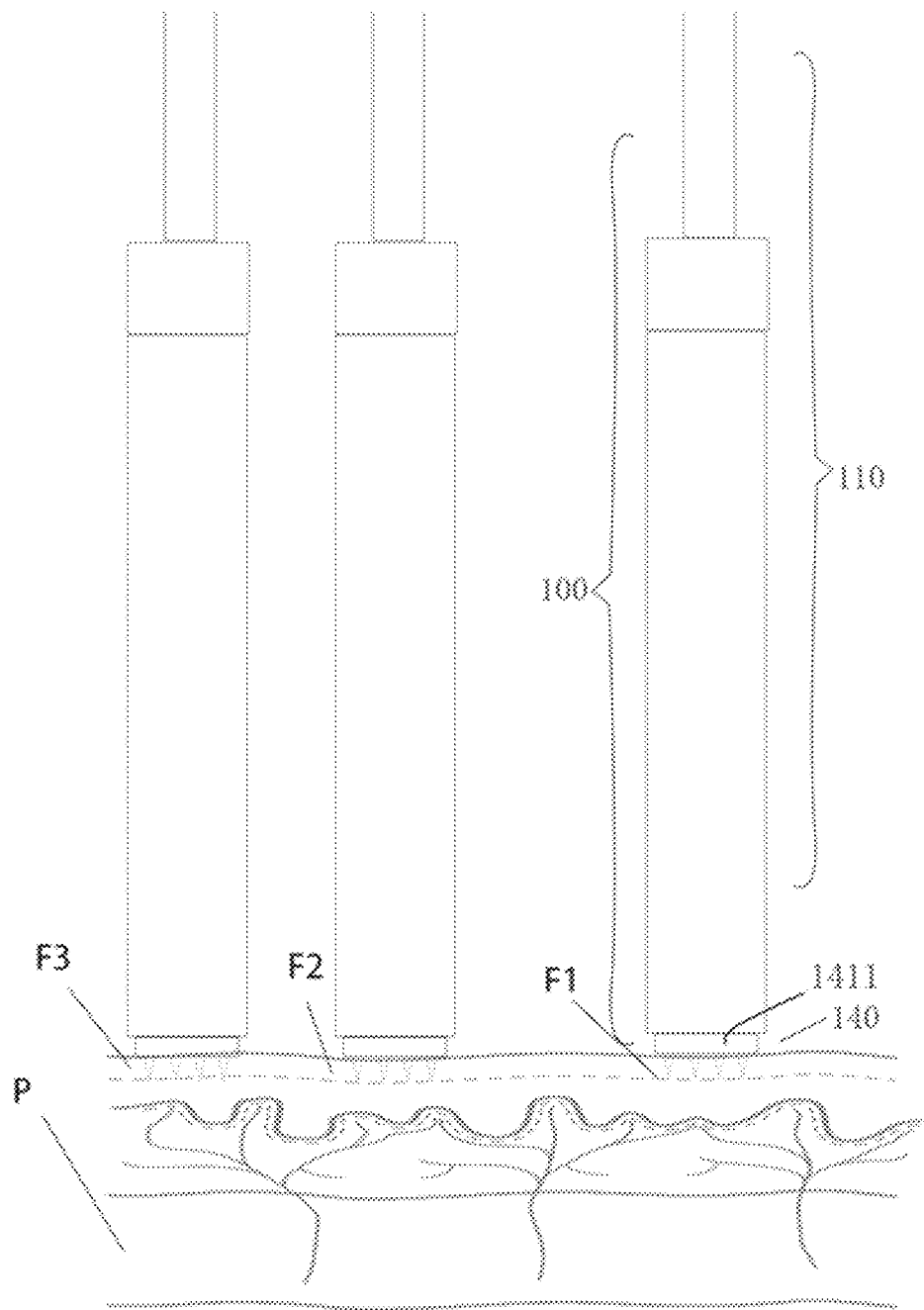
FIG. 33 shows a cross-sectional view of the tattoo needle piercing into the skin according to an embodiment of the present disclosure.

FIG. 33 shows a cross-sectional view of the tattoo needle in the present disclosure being used to pierces into the skin. The tattoo needle includes a single row of needles 100, and a piercing depth when the needles 100 pierce into the skin may be accurately limited in advance. When the tattoo needle pierces and colours the skin P, the substrate 1411 limit the piercing depth of the needles 100 piercing into the skin. In this way, depths F1, F2, and F3 reached by the needles 100 piercing into the skin in various times may be the same.

Figure 34:
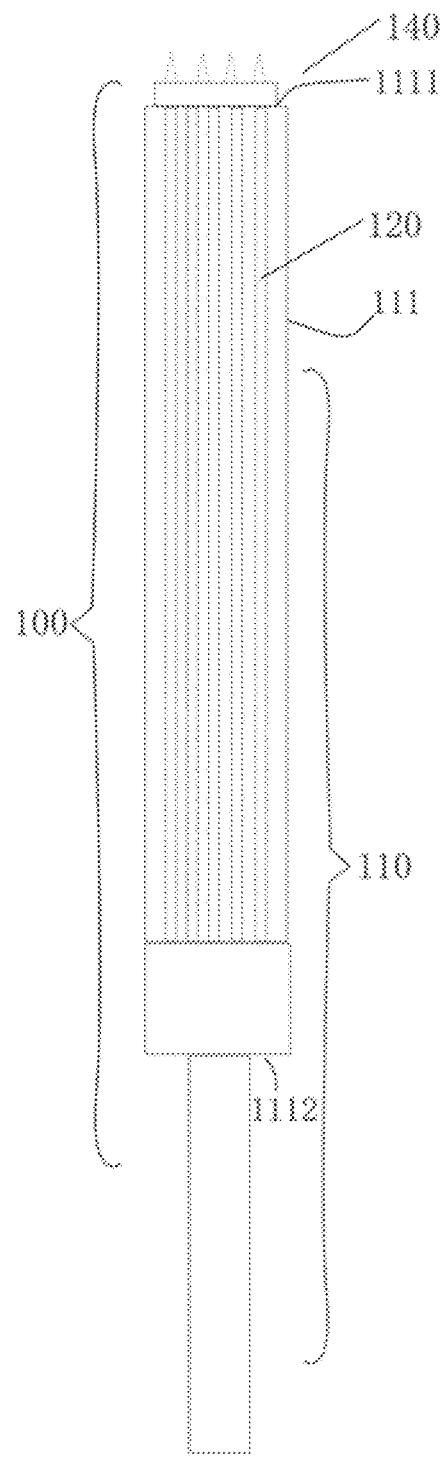
FIG. 34 is a structural schematic view of a tattoo needle according to an embodiment of the present disclosure.
Figure 35A:
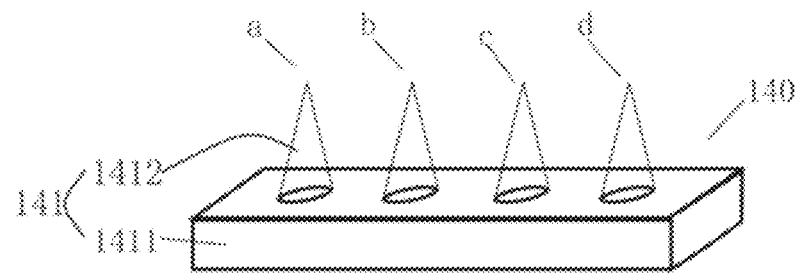
FIG. 35(a) is a structural schematic view of the needle piercing portion according to an embodiment of the present disclosure.
Figure 35B:
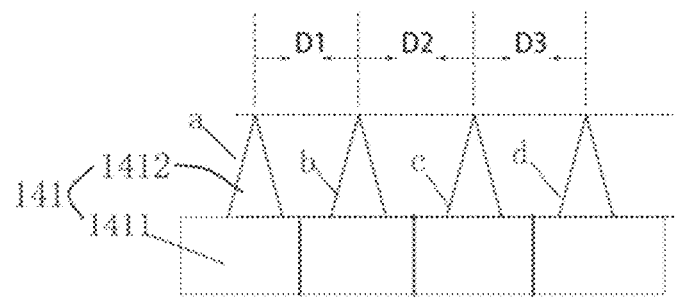
FIG. 35(b) is a cross-sectional view of the needle piercing portion according to an embodiment of the present disclosure, viewed from a viewing angle.
Figure 35C:
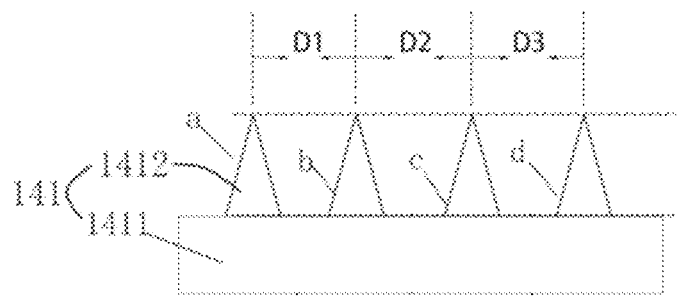
FIG. 35(c) is a cross-sectional view of the needle piercing portion according to another embodiment of the present disclosure, viewed from a viewing angle.

As shown in FIG. 34, the tattoo needle in FIG. 34 includes a needle piercing portion 140, a liquid guiding member 110, and a capillary liquid storage unit 120 arranged on an outer wall of the liquid guiding member 110. As shown in FIG. 35(a), the piercing projection 141 includes four needle teeth 1412 and a substrate 1412. A length that each of four needle teeth 1412 pierces into the skin may be predefined. The four needle teeth 1412 are arranged on the substrate 1411. As shown in the drawings, each of four needle teeth 1412 is conical. The substrate 1411 and the four needle teeth a, b, c, d are configured as a one-piece and integral structure. The substrate 1411 limits the piercing depth that each of four needle teeth 1412 pierces into the skin. As shown in FIG. 35(b), the piercing projection 141 includes four needle teeth 1412 and the substrate 1412. The length that each of four needle teeth 1412 pierces into the skin may be predefined. The four needle teeth 1412 are arranged on the substrate 1411. FIG. 35(c) shows a cross-sectional view of the needle piercing portion in an embodiment. The four needle teeth a, b, c, and d have a same height and are spaced apart from each other with equal spacing. A center spacing between the needle tooth a and the needle tooth b is D1, a center spacing between the needle tooth and the needle tooth c is D2, a center spacing between the needle tooth c and the needle tooth d is D3, and D1=D2=D3. The D1 is greater than 0 less than 1500 μm. The center spacing refers to a distance between a tip end of one needle tooth to a tip end of an adjacent needle tooth. It will be understood that, in other embodiments, the four needle teeth a, b, c, and d may have different heights and are non-equally spaced apart from each other.

Figure 35D:
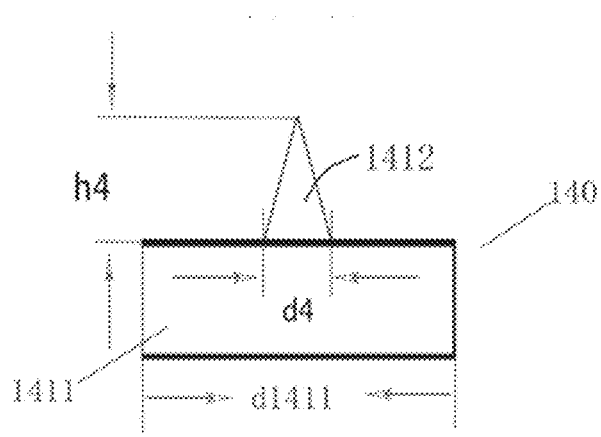
FIG. 35(d) is a cross-sectional view of the needle piercing portion according to an embodiment of the present disclosure, viewed from another viewing angle.

FIG. 35(d) shows a cross-sectional view of a short edge of the substrate on which the piercing projection is arranged. As shown in FIG. 35(d), a diameter of a bottom of the needle tooth of any piercing projection is d4, and a height of the needle tooth of any piercing projection is h4. Based on repeated experiments, in order to achieve a better effect of guiding the colour pigments, 20 μm≤d4≤500 μm, 50 μm≤h4≤1000 μm, and d4<h4.

As shown in FIG. 35(d), in an embodiment, the substrate 1411 of the present disclosure may be in any polygonal shape. The needle teeth 1412 may be arranged on a side surface of the substrate 1411. In order to obtain the better effect of guiding the colour pigments, a length of the shortest edge of the substrate 1411 is recorded as d1411, when d1411>d4, the better effect of guiding the colour pigments may be achieved. Based on this configuration, the colour pigments may flow from the thicker liquid guiding post 111 to the substrate 1411 and further flow from the substrate 1411 to the needle teeth 1412.

Figure 36A:
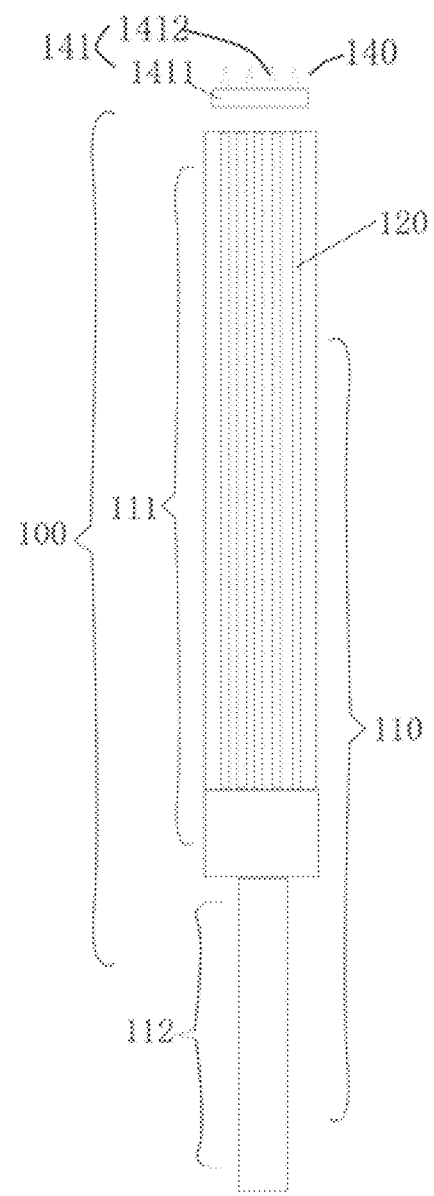
FIG. 36(a) is an exploded view of the tattoo needle according to an embodiment of the present disclosure.

As shown in FIG. 36(a), the liquid guiding member 110 is a strip and includes a liquid guiding post 111 and a connecting rod 112. The liquid guiding post 111 is disposed near the piercing projection 141. The liquid guiding post 111 may have an upper section and a lower section, and the upper section and the lower section are equal sized. The liquid guiding post 111 and the connecting rod 112 are fixedly connected with each other. The liquid guiding post 111 may be adhered to and fixed to the substrate 1411 of the piercing projection 141.

Figure 36B:
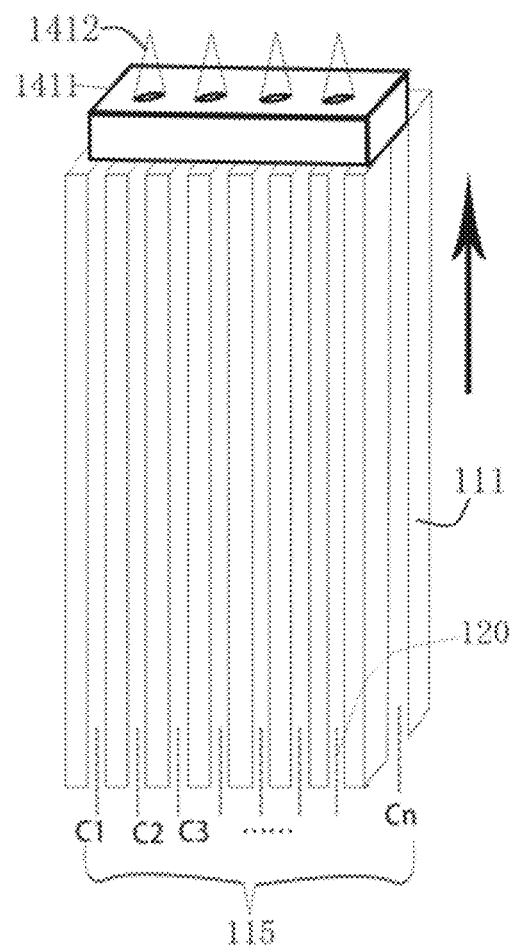
FIG. 36(b) is a perspective view of the tattoo needle according to an embodiment of the present disclosure, viewed from a viewing angle.

As shown in FIG. 36(b), the outer wall of the liquid guiding member 110 defines a plurality of channels C1, C2, C3 . . . , and Cn. A capillary liquid storage space of the plurality of channels 115 serves as the capillary liquid storage unit 120. Each of the plurality of channels C1, C2, C3 . . . , and Cn, is configured to guide the colour pigments to guide to flow to the piercing projection 141 in a direction as shown by the arrows in FIG. 36(b).

Figure 37A:
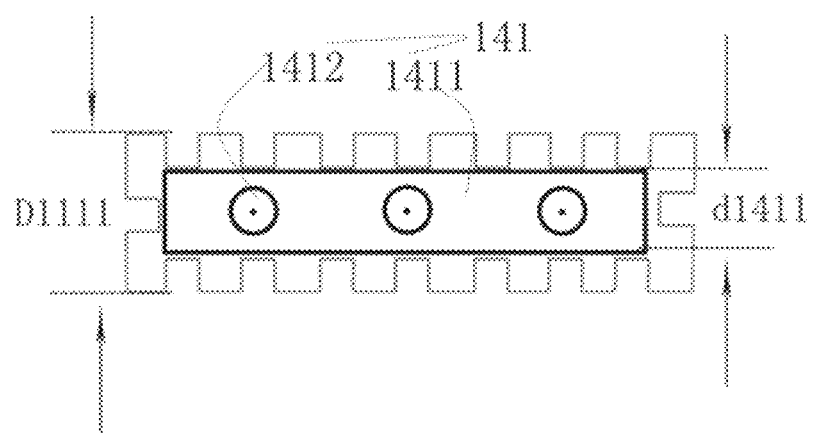
FIG. 37(a) is a planar schematic view of the tattoo needle described according to an embodiment of the present disclosure.
Figure 37B:
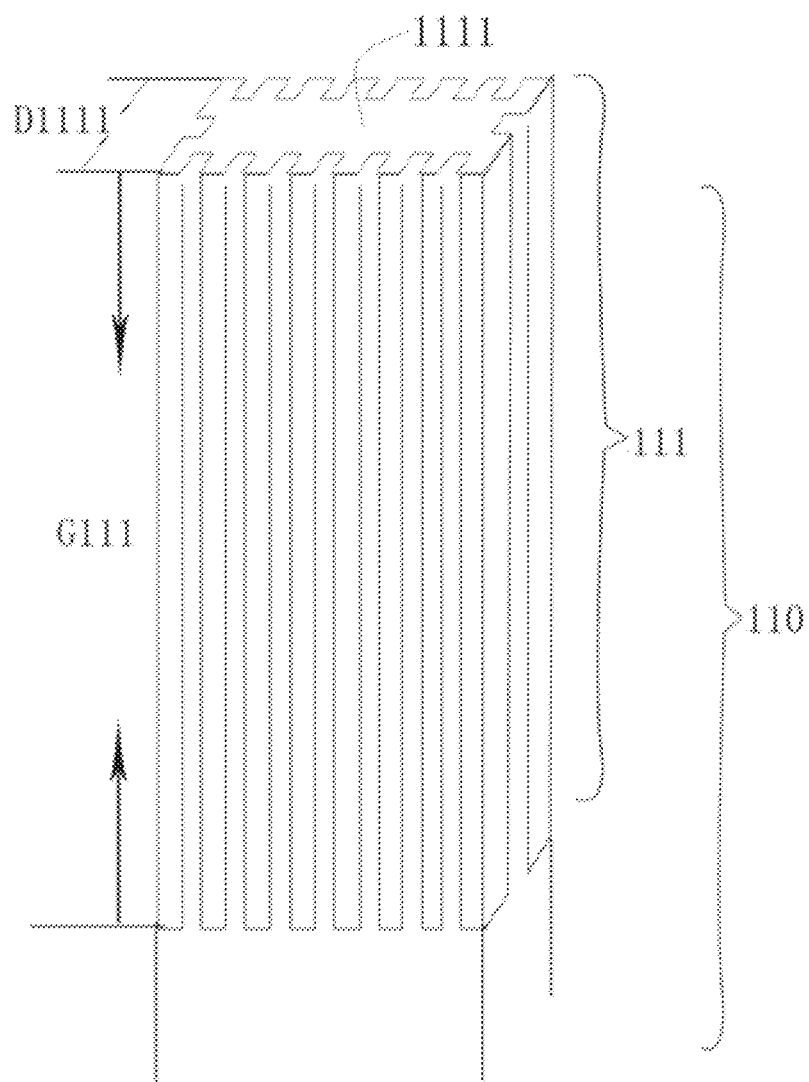
FIG. 37(b) is a perspective view of a liquid guiding member described according to an embodiment of the present disclosure.

As shown in FIG. 37(a) and FIG. 37(b), the length of the short edge of the substrate 1411 on which the piercing projection 141 is arranged is noted as d1411, the height of the liquid guiding post 111 of the liquid guiding member 110 is noted as G111, and the length of the shortest edge of the first end face 1111 of the liquid guiding post 111 is noted as D1111. Based on repeated experiments, in order to have a certain rigidity, 180 μm≤D1111≤1800 μm. In order to obtain the better effect of guiding the colour pigments, D1111 ≥ d1411. In the present embodiment, in order to allow an increased amount of ink to be carried and to allow the ink to be released continuously and slowly, G111>2×D111, and that is, the height G111 of the liquid guiding post 111 is greater than two times of the length D1111 of the shortest edge of the liquid guiding member 110 near the piercing projection 141. Of course, a cross section of the piercing projection 141, taken by the substrate 1411, may be arbitrary polygonal, for example, the cross section may be triangular, quadrilateral, pentagonal, or in other regular or irregular polygonal shapes. When the shape of the substrate 1411 is arbitrary polygonal, an axial length of the liquid guiding post 111 is at least two times of the length of the shortest edge of the first end face 1111 of the liquid guiding post 111, and the axial length of the liquid guiding post 111 is greater than the length of the longest edge of the first end face 1111. In an embodiment, each of the plurality of channels (115) extends vertically or spirally from the first end face (1111) to the second end face. An end of each of the plurality of channels (115) may extend through or approach the second end face (1112). Each of the plurality of channels (115) may extend vertically along the liquid guiding post (111) to reach the first end face (1111). Each of the plurality of channels (115) may be an annular groove defined in the outer wall of the liquid guiding post (111), and the plurality of annular grooves are spaced apart from each other and are defined in the outer wall of the liquid guiding post (111).

Figure 38A:
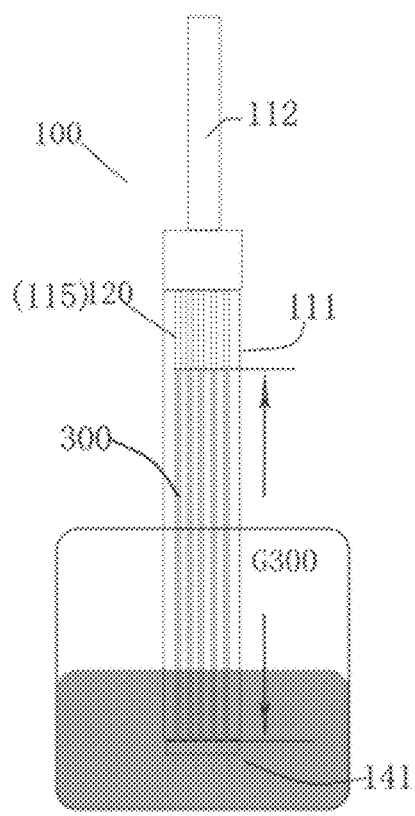
FIG. 38(a) is a schematic view of an in-use state of the tattoo needle absorbing ink according to an embodiment of the present disclosure.

As shown in FIG. 38(a), when the tattoo needle 100 is dipped into and intakes the colour pigments (the colour pigments and the ink in the present disclosure refer to dyes that can colour the skin), the capillary liquid storage unit 120 arranged on the tattoo needle 100 absorbs the colour pigments based on a capillarity absorption principle and temporarily stores colour pigments.

Figure 38B:
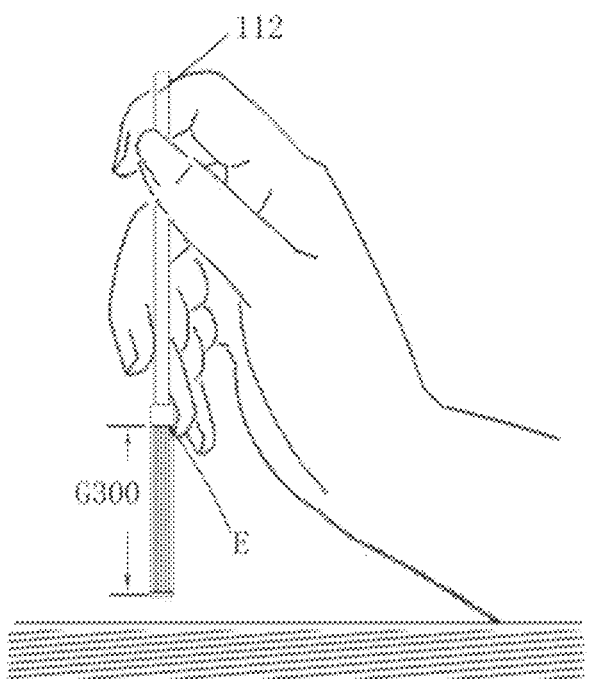
FIG. 38(b) is a schematic view of an in-use state of the tattoo needle in FIG. 13(a) piercing into the skin, after the absorbing ink, according to an embodiment of the present disclosure.

The colour pigments rises up along the channels of the capillary liquid storage unit 120 to form a pigment column, recorded as G300. By collecting and analyzing data, a density of the pigments in the art at room temperature is about 0.7-1.31 g/ml, and a surface tension of the pigments at the room temperature is almost equal to a surface tension of water, which is about 72 mN/m. A capillary formula is as follows: a height h that the liquid rises along a capillary tube=2*surface tension coefficient*cosθ/(density of the liquid*gravitational acceleration g*radius of the capillary tube r). The θ is an angle between a liquid surface and a wall of the capillary tube. The radius of the channel of the liquid storage unit 120 (or the depth and/or width of the channel) corresponds to the radius of the capillary tube r in the capillary formula. According to the experimental test and verification of the capillary formula, as the radius (or the depth and/or the width) of the channel of the capillary liquid storage unit 120 is reduced, the G300 is increased. That is, as the channel of the capillary liquid storage unit 120 is thinner, the height of the pigment column is higher, and more pigments may be carried. Therefore, the needle may not dip the pigments frequently, the tattooing may be performed continuously and efficiently. In the present embodiment, the liquid guiding member 110 of the tattoo needle 100 is made of plastics. Based on precision of the main production process in the art, the radius of the channel of the capillary liquid storage unit 120 may be made to have a precision of 0.1 mm, and the height of the pigment column G300 may be more than 100 mm. However, as shown in FIG. 38(*b*), according to a conventional way that the operator holds the tattoo needle 100 by hand and a measurement of dimensions of a general human hand, a lowest position E of the tattoo needle 100 that is held by the hand is generally not more than 50 mm from the needle tip. Therefore, the height of the channel of the capillary liquid storage unit 120 arranged on the tattoo needle 100 in the present embodiment is <50 mm.

Figure 39A:
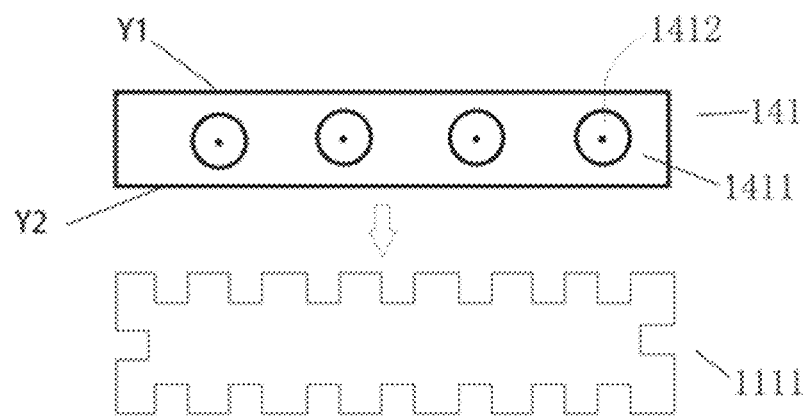
FIG. 39(a) is a schematic view of the needle piercing portion being mounted with the liquid guiding post according to an embodiment of the present disclosure.
Figure 39B:
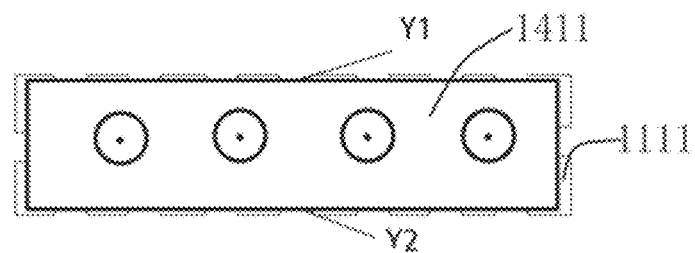
FIG. 39(b) is a schematic view of the substrate being mounted with the liquid guiding post according to an embodiment of the present disclosure.
Figure 39C:
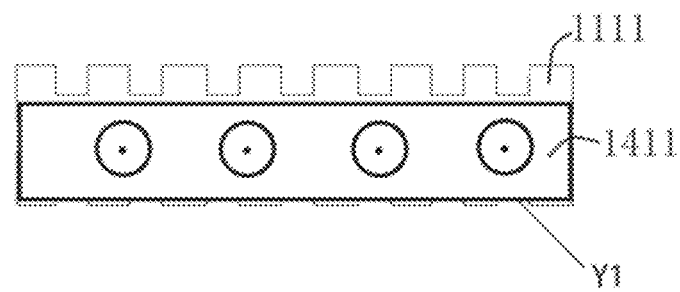
FIG. 39(c) is a schematic view of the substrate being mounted with the liquid guiding post according to another embodiment of the present disclosure.

As shown in FIG. 39(*a*), the piercing projection 141 may be adhered on the first end face 1111 of the liquid guiding post, obtaining structures shown in FIG. 39(*b*) and FIG. 39(*c*). In order to achieve the better effect of guiding the colour pigment, at least one side (Y1, Y2) of the substrate 1411 on which the piercing projection 141 is arranged is aligned (or infinitely approach) with an edge of an outer wall of the first end face 1111 of the liquid guiding member 110.

In an embodiment, at least one substrate 1411 of the piercing projection 141 is disposed at a middle of an end face of the liquid guiding member 110, and a distance from the edge of the outer wall of the liquid guiding member to one corner or one edge of the substrate is not more than 0.18 mm. That is, in an embodiment, the substrate may be disposed at a center of the first end face. However, in order to achieve the better effect of guiding the pigments, a distance from the edge of the outer wall of the liquid guiding member to one corner or one edge of the substrate is not more than 0.18 mm.

Figure 40:
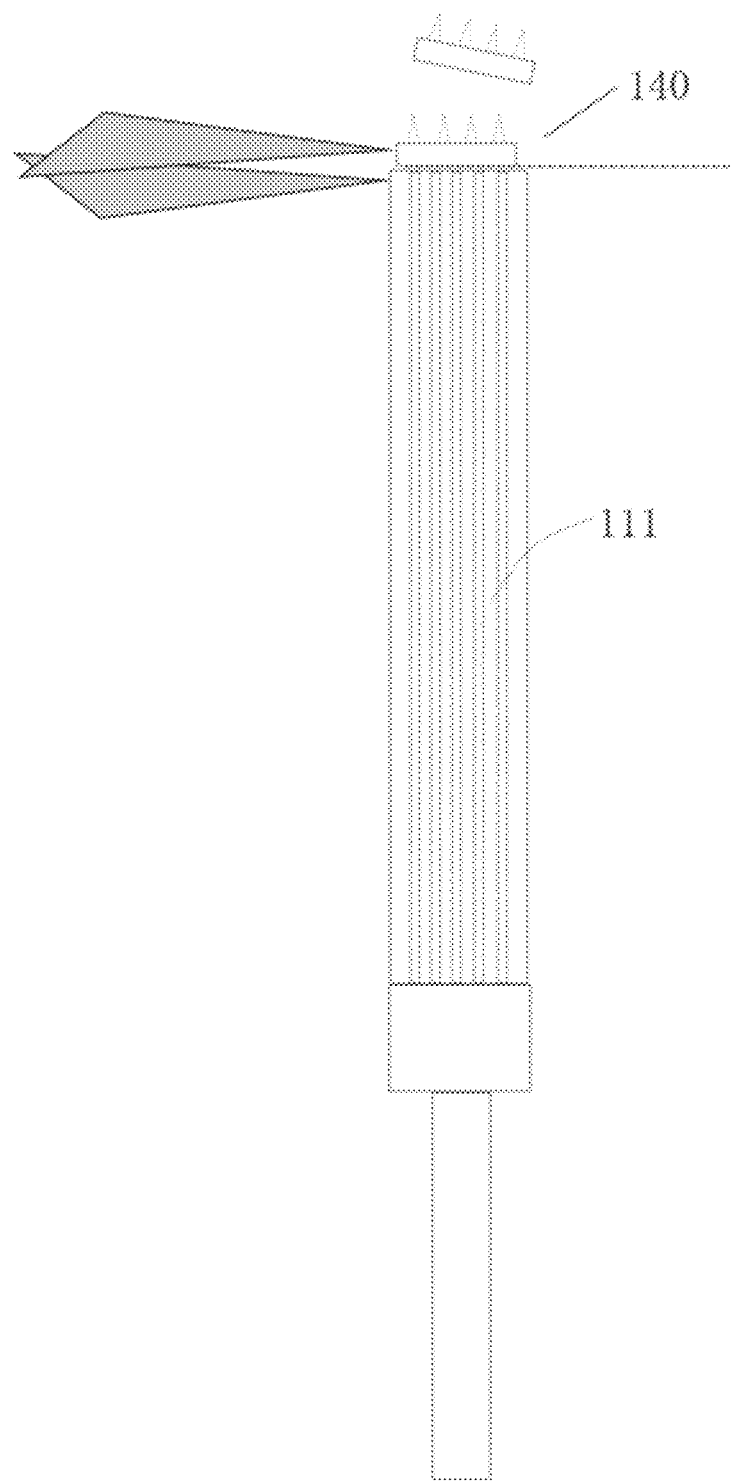
FIG. 40 is a schematic view of a state of destroying a used tattoo needle according to an embodiment of the present disclosure.

As shown in FIG. 40, for the tattoo needle 100 in the present embodiment, an adhesive seam is defined between the liquid guiding member 110 and the piercing projection 141. After use, the tattoo needle 100 may be functionally destroyed by separating, by any sharp instrument, the liquid guiding member 110 from the piercing projection 141.

Embodiment 2

Figure 41A:
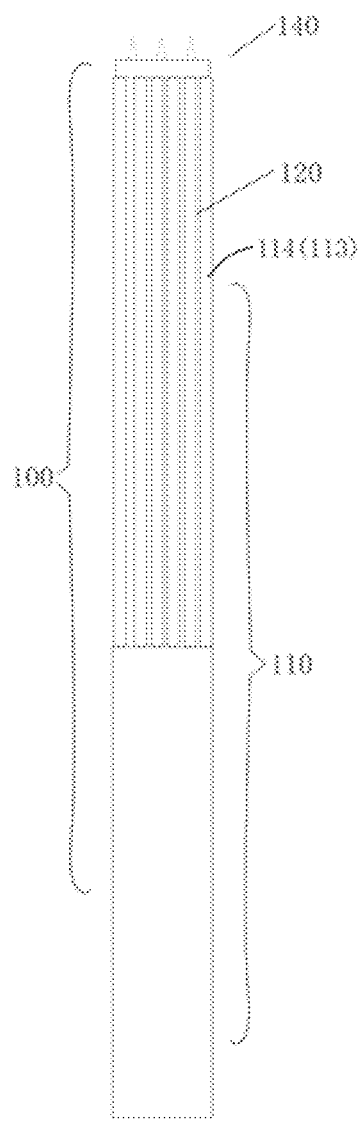
FIG. 41(a) is a schematic view of a tattoo needle according to an embodiment of the present disclosure.
Figure 41B:
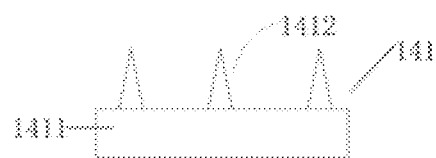
FIG. 41(b) is a schematic view of the needle piercing portion in FIG. 16(a).
Figure 41C:
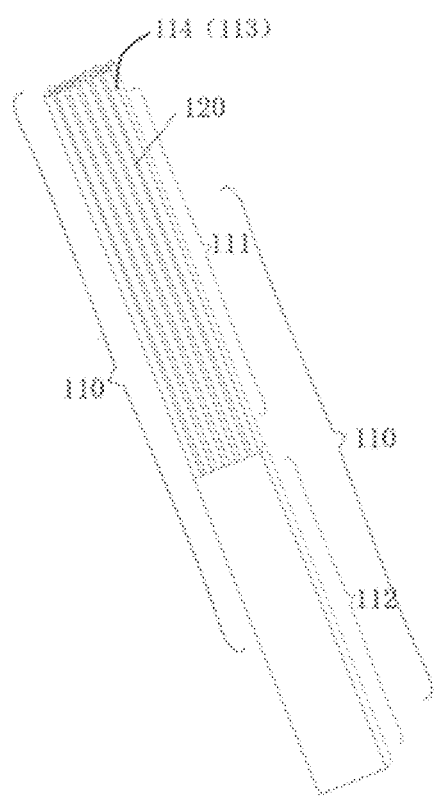
FIG. 41(c) is a schematic view of the liquid guiding member in FIG. 16(a).

In an embodiment, FIG. 41(*a*) shows a tattoo needle 100 having a single row of needles, and the piercing depth that the needles pierce into the skin can be predefined accurately. The tattoo needle 100 includes a piercing projection 141, a liquid guiding member 110, and a capillary liquid storage unit 120.

As shown in FIG. 41(*b*), the piercing projection 141 includes three needle teeth and one substrate 1411. The piercing depth that the three needle teeth pierce into the skin is predefined, and the three needle teeth 1412 are arranged on the substrate 1411. Each of the three needle teeth may be either tower-shaped or conical. FIG. 41(*b*) shows conical needle teeth. The substrate 1411 and the three needle teeth are configured as a one-piece and integral structure. The substrate 1411 limits the piercing depths that the three needle teeth pierce into the skin.

As shown in FIG. 41(*c*), the liquid guiding member 110 is a strip and includes a liquid guiding post 111 and a connecting rod 112. The liquid guiding post 111 is disposed near the piercing projection 141. The liquid guiding post 111 may have an upper section and a lower section, and the upper section and the lower section are equal sized. The liquid guiding post 111 includes twelve metal filaments, each of the twelve metal filaments has a flat-cut end (the filaments in the drawings are only schematic to show one configuration of the liquid guiding post, and the filaments may alternatively be referred to as flat-end needle filaments 113 or small posts 114), C1, C2, C3 . . . , and C12. The twelve metal filaments, C1, C2, C3 . . . , and C12, may be adjacent to each other and are not fixedly connected with each other. A gap between the twelve metal filaments may have the capillary effect and serves as the capillary liquid storage unit 120. The liquid guiding post 111 and the connecting rod 112 are fixedly welded with each other.

Figure 42A:
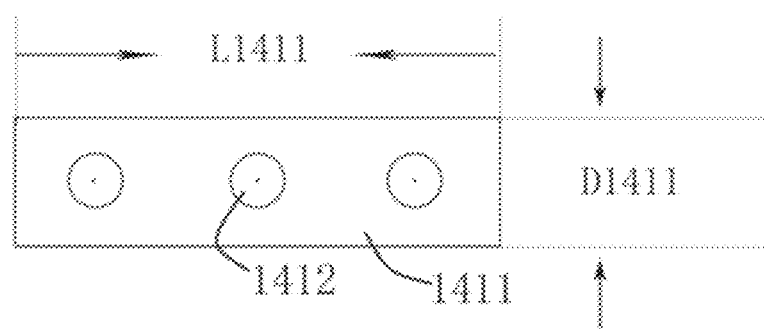
FIG. 42(a) is a planar schematic view of the needle piercing portion according to an embodiment of the present disclosure, viewed from a viewing angle.
Figure 42B:
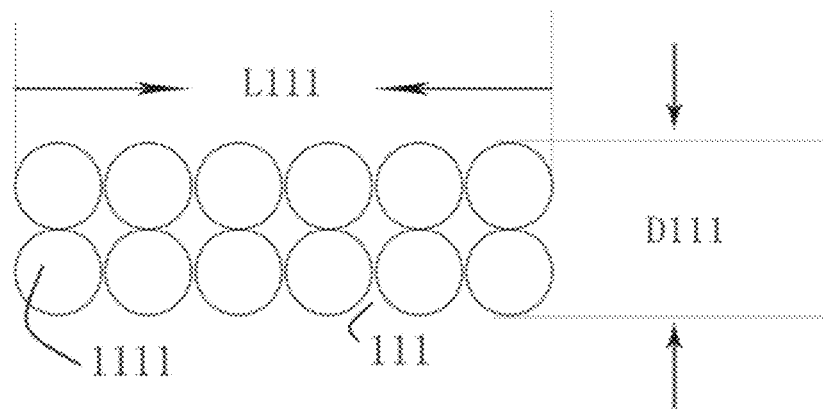
FIG. 42(b) is a cross-sectional view of the liquid guiding post (referred to as a planar schematic view of the first end face of the liquid guiding post) according to an embodiment of the present disclosure.

As shown in FIG. 42(*a*) and FIG. 42(*b*), in order to obtain the better effect of guiding the colour pigments, a longer edge L1411 of the cross section of the substrate 1411 is shorter than or equal to a longer edge L111 of the first end face 1111 of the liquid guiding member 111, and that is, L1411≤L111. The shorter edge D1411 of the cross section of the substrate 1411 is shorter than or equal to the shorter edge D1111 of the first end face 1111 of the liquid guiding member 111.

Figure 43A:
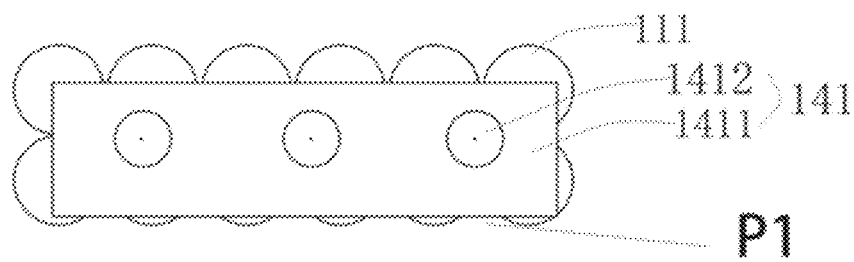
FIG. 43(a) is a schematic view of the needle piercing portion being disposed on the first end surface of the liquid guiding post according to an embodiment of the present disclosure.
Figure 43B:
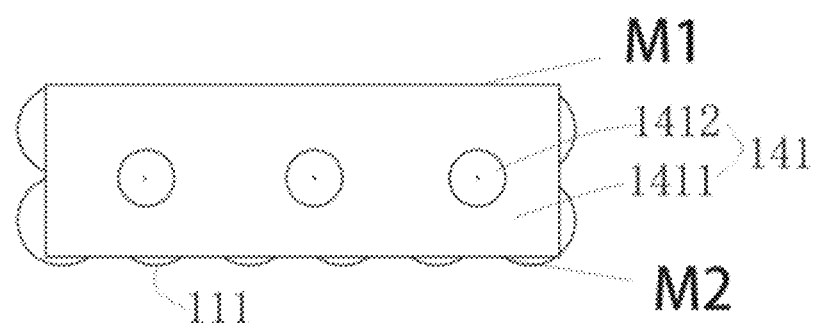
FIG. 43(b) is a schematic view of the needle piercing portion being disposed on the first end surface of the liquid guiding post according to another embodiment of the present disclosure.

As shown in FIG. 43(*a*) and FIG. 43(*b*), one longer edge P1 of the substrate 1411 of the piercing projection 141 is aligned (infinitely approach) with the edge of the outer wall of the liquid guiding post 111. Alternatively, as shown in FIG. 43(*b*), two longer edges M1, M2 of the substrate 1411 of the piercing projection 141 are aligned (infinitely approach) with the edge of the outer wall of the liquid guiding post 111.

Figure 44:
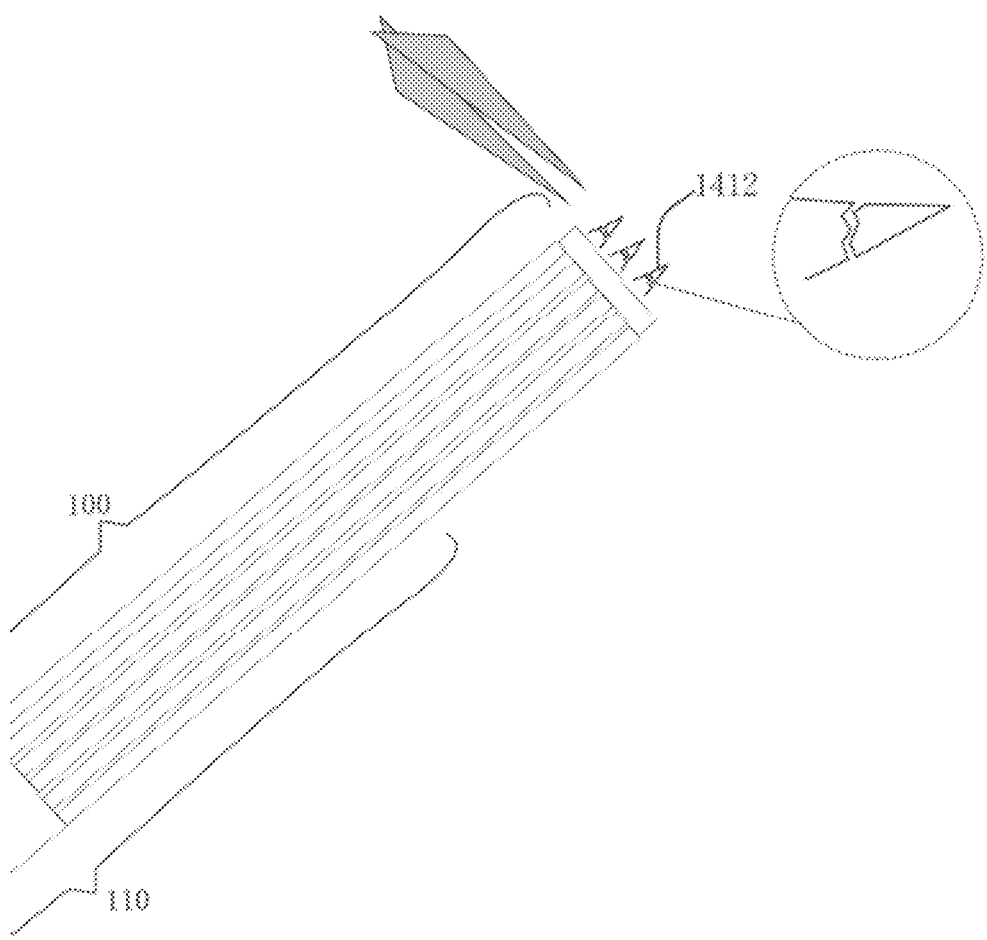
FIG. 44 is a schematic view of a state of destroying a used tattoo needle according to an embodiment of the present disclosure.

As shown in FIG. 44, for the tattoo needle 100 in the present embodiment, the liquid guiding member 110 and the piercing projection 141 are welded and fixed with each other. The piercing projection 141 may be made of monocrystalline silicon. The tattoo needle 100 may be functionally destroyed by using a sharp instrument to knock off the needle teeth.

Figure 45A:
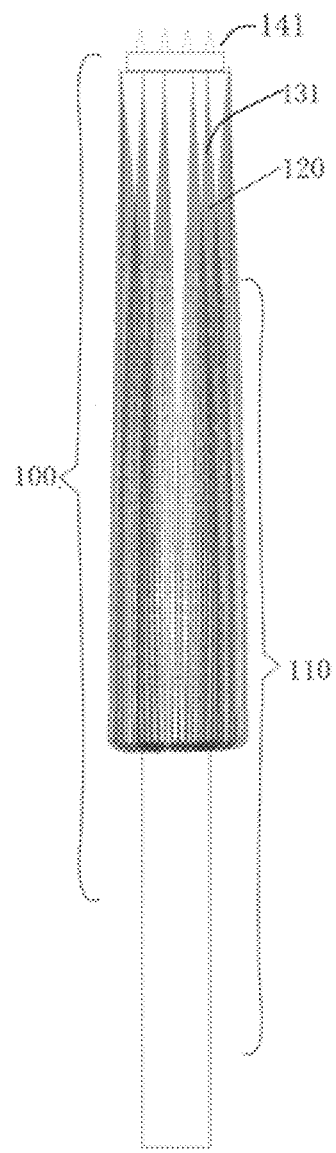
FIG. 45(a) is a schematic view of the tattoo needle according to an embodiment of the present disclosure.
Figure 45B:
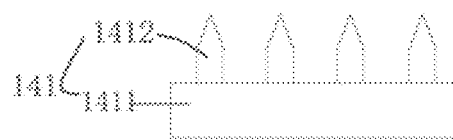
FIG. 45(b) is a cross-sectional view of the needle piercing portion in FIG. 20(a).
Figure 45C:
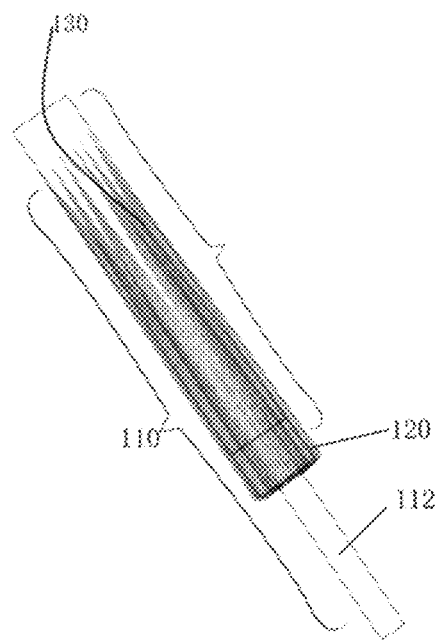
FIG. 45(c) is a schematic view of the liquid guiding member in FIG. 20(a).

Embodiment 3:

In an embodiment, FIG. 45(*a*) shows a tattoo needle 100 having a single row of needles, and the piercing depth that the needles pierce into the skin can be predefined accurately. The tattoo needle 100 includes a piercing projection 141, a liquid guiding member 110, and a capillary liquid storage unit 120.

The liquid guiding member 110 is fixed with the piercing projection 141. As shown in FIG. 45(*b*), the piercing projection 141 includes four needle teeth and a substrate 1411. The length that each of the four needle teeth pierces into the skin may be predefined, and the four needle teeth are arranged on the substrate 1411. Each of the four needle teeth is tower shaped, and the substrate 1411 and the four needle teeth are configured as a one-piece and integral structure. The substrate 1411 limits the piercing depth that the four needle teeth pierce into the skin. As shown in FIG. 45(*c*), in an embodiment, the liquid guiding member 110 is a strip and includes a liquid guiding post 111 and a connecting rod 112. A portion of the liquid guiding post 111 near the piercing projection 141 is columnar. A fibrous substance is attached to the outer wall or a side of the liquid guiding post 111. A gap inherently included in the fibrous substance and a gap between the fibrous substance and the outer wall of the liquid guiding post 111 serve as the capillary liquid storage unit 120.

As shown in FIG. 32(*a*) to FIG. 32(*d*), in an embodiment, a tattoo needle in the present embodiment includes a liquid guiding member 110 and a needle piercing portion 140 disposed at an end of the liquid guiding member 110. The needle piercing portion 140 includes at least one piercing projection 141. Each piercing projection 141 includes a substrate 1411 and a needle tooth 1412. The needle tooth 1412 is fixedly arranged on a side surface of the substrate 1411. The needle piercing portion shown in FIG. 32(*b*) includes one piercing projection 141, and the piercing projection 141 includes one substrate 1411 and four needle teeth 1412 arranged on the substrate 1411. The needle piercing portion shown in FIG. 32(c) includes four piercing projections 141.

Each of the four piercing projections 141 includes one substrate 1411 and one needle tooth 1412 arranged on the substrate 1411 (or a plurality of needle teeth on the substrate 1411, FIG. 32(c) shows one needle tooth arranged on the substrate).

As shown in FIG. 31, when the device 1000 having a row of needles pierces into the skin and repeatedly sweeps to apply colour to the skin, the needle filaments of the device 1000 encounter different resistance forces, needle tips M of the needle filaments are bent to different extent, and spacings between the needle filaments may be changed. As shown in FIG. 33, when the tattoo needle of the present disclosure is used to repeatedly sweep, streak, or prick at points to colour the skin, piercing depths that the needle teeth pierce into the skin is controllable through the substrate 1411. The needle teeth may not compress each other and may not be elastically deformed. While the tattoo needle is being used, the needle teeth may not impact each other, the piercing depths that the needle teeth pierce into the skin is controllable, and the needle teeth may not be bent. Therefore, the tattoo needle of the present disclosure has better effect and structural advantages over the device that has a row of needles in the art.

The present disclosure further provides a tattoo device as shown in FIGS. 46 to 53.

As shown in FIGS. 46 to 48b, the tattoo device includes an injection needle and an operating rod. The operating rod includes a shell 1 and a driving mechanism 2 arranged inside the shell. The bottom of the shell (an end where the injection needle is protruded) is arranged with a first fastener 3. The shell 1 is at least partially arranged inside a case 4. The first fastener is received inside a lower portion of the case (a portion near the end where the injection needle is protruded). A first internal fastener 5a is arranged on an inner wall of a bottom of the case.

A top of the case (an end away from the end where the injection needle is protruded) is screwed to the outer surface of the middle portion of the shell.

In the present embodiment, the tattoo device includes the operating rod and the injection needle 6 (which includes the substrate, the needle tooth, the liquid guiding member, and other structure as described in the above embodiments). The injection needle is mounted to the bottom of the operating rod. The driving mechanism is configured to drive the components of the injection needle to move to perform the tattooing. The first fastener is configured to connect to the injection needle. In the art, the operating rod is also connected to the injection needle through a fastener. However, if only one fastener is used for connection, the fastening connection may be loosen easily, causing safety hazards. Therefore, in the present disclosure, the case is arranged to receive the shell, and the first internal fastener is arranged on the bottom of the case. After the shell and the injection needle are connected through the first fastener, the case and the injection needle are also fastened to each other, such that two fastening connections are achieved. The injection needle is arranged with two fasteners, one of the two fasteners is fastened with the first fastener on the shell, and the other one of the two fasteners is fastened with the first inner fastener on the case. In this way, the operating rod and the injection needle are fastened to each other through two independent connections, and strength of the connection therebetween is higher. Even if one of the two fastening connections is loose, the other one of the two fastening connections enables the operating rod to be connected to the injection needle. Stability and safety of the tattooing process are ensured. In the art, only one fastening connection is achieved. When the operating rod is fastening with the injection needle, if a central axis of the injection needle does not coincides with a central axis of the operating rod, the operator may not notice any inclination or deviation. In this case, the tattooing process may not be performed accurately, and the user may be hurt. Therefore, in the present disclosure, the case is arranged to fasten to the injection needle to achieve the second fastening. Although one fastening may be inclined or deviated, it is very unlikely to have both fastening connections inclined or deviated. The operator may notice and correct the inclination and deviation, ensuring that the central axis of the operating rod coincides with the central axis of the injection needle, and accuracy and safety of the tattooing process can be achieved.

An annular limiting space 10 is defined between an outer surface of a middle portion of the shell and an inner surface of the case 3. A limiting member 12 is arranged on an outer surface of the other end portion of the case. The limiting member is received in the annular limiting space. The limiting member and the case are slidable along an axis of the shell. The limiting member and the case may rotate around the shell. A distance that the case can move along the axis of the shell is limited by the limiting member and the annular limiting space. That is, the limiting member and the case may slide and rotate outside the shell. Due to the annular limiting space, the limiting member is received in the annular limiting space, a vertical distance that the case slides along the shell is limited by a length of the annular limiting space. The case may move upwardly along the axis of the shell, and when the limiting member abuts against a top wall of the annular limiting space, the case is prevented from further moving upward. When the case moves downward along the axis of the shell and the limiting member abuts against a bottom wall of the annular limiting space, the case is prevented from further moving downward. That is, the limiting member and the annular limiting space cooperatively limit the vertical distance that the case moves along the shell.

A pushing member 10a is arranged in the annular limiting space. The pushing member is disposed between the top wall of the annular limiting space and a top wall of the limiting member. The pushing member applies a downward force to the limiting member to push the limiting member and the case to move downward to enable the limiting member to move away from the top wall of the annular limiting space.

A bottom of the shell (i.e., an end from which the injection needle is protruded out) is arranged with a fastener 3, and the fastener 3 is arranged coaxially with the shell. The bottom of the case is disposed outside the fastener. The case is coaxial with the fastener. When the bottom wall of the limiting member abuts against the bottom wall of the annular limiting space, the bottom of the case is located below a bottom of the fastener, i.e., the fastener is now completely received inside the case. When the top wall of the limiting member abuts against the top wall of the annular limiting space, the bottom of the case is located above the bottom of the fastener, i.e., the fastener is now at least partially protrudes out of the case; or the bottom surface of the case is aligned with the bottom surface of the fastener. When the case moves upward, the bottom surface of the case may be aligned with the bottom surface of the fastener or the fastener is at least partially protrudes out of the case. In this way, the fastener may be exposed to be fastened with the injection needle. In the present embodiment, when the case moves upward, the fastener is at least partially protrudes out of the case. The bottom of the case is arranged with a fastener, configured to be fastened with the injection needle. The fastener may be threads, and the threads may be outer threads or inner threads. In the present embodiment, the inner threads are arranged on an inner wall of the bottom of the case.

In the present embodiment, the fastener on the shell serves as a primary fastener to be fastened with the injection needle, and the fastener on the case serves as a secondary fastener to be fastened with the injection needle. The case may be rotatably connected to an outside of the shell. In addition, due to the limiting member and the annular limiting space, the case may rotate around the shell and may move along the axis of the shell. Since the case is not connected to the shell through threads, the inner threads at the bottom of the case may be easily threaded with the injection needle, and the case, when being processed, is required to be engaged with the threads on the injection needle only. By omitting the thread connection between the case and the shell, processing difficulty of the operating rod is effectively reduced, a production efficiency is improved, and production costs are reduced.

In the present embodiment, the bottom of the fastener of the shell is the primary fastener that is fastened with the injection needle, and the fastener of the case is the secondary fastener that is fastened with the injection needle. A bottom of the fastener of the shell may be arranged with threads, rubber, buckles, and so on, to be connected with the injection needle. However, in a case that the tattoo device is not in use, when the bottom of the fastener of the shell is exposed out of the case and the tattoo device is placed on a table, the fastener may be worn, affecting stability of the connection between the fastener and the injection needle and affecting the service life of the operating rod. Therefore, in the present embodiment, the pushing member is arranged to allow the bottom of the case to always move downward when the operating rod is not connected with the injection needle, i.e., the bottom wall of the limiting member is ensured to abut against the bottom wall of the annular limiting space, such that the fastener is always received inside the case. Therefore, the case shields and protects the fastener of the shell, preventing the fastener of the shell from being worn or damaged. Moreover, the threads of the case are inner threads, i.e., the threads of the case itself are also protected and cannot be worn or damaged.

The injection needle includes a first fastener and a second fastener. When the operating rod is connected to the injection needle, an operator grasps the shell and the case at the same time. Further, the operator applies an upward force to the case to overcome the downward force applied by the pushing member, such that the case moves upward along the shell to expose the fastener of the shell. In this way, the fastener of the shell is fastened to the first fastener on the injection needle to achieve the primary fastening. Subsequently, the upward force applied to the case may be released, and the case is pushed downward by the pushing member to receive the shell and to allow the fastener on the case to be fastened to the second fastener on the injection needle to achieve the second fastening. During performing the second fastening, the case rotates around and outside the shell, and the limiting member rotates in the annular limiting space. During rotating, the case moves downward gradually to allow the inner threads of the case to be threaded with the secondary fastener of the injection needle.

In the present embodiment, the pushing member applies the downward force to the case. After the operating rod is connected to the injection needle, the downward force increases a friction between the fastener of the case and the second fastener of the injection needle. In this way, the injection needle is prevented from being detached off from the operating rod during tattooing, ensuring stability of the tattooing operation and ensuring the tattooing effect.

Figure 46:
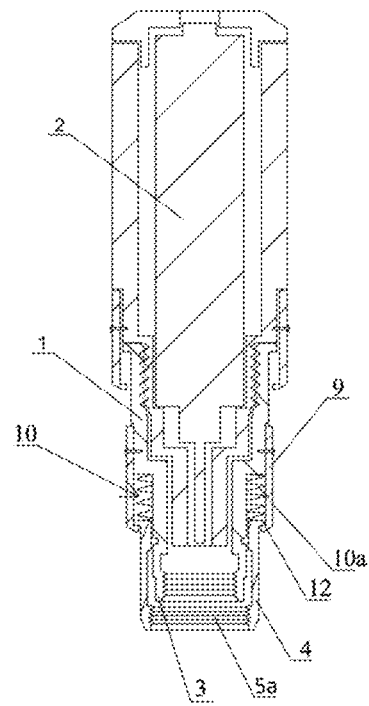
FIG. 46 is a structural schematic view of a tattoo needle according to an embodiment of the present disclosure.
Figure 47:
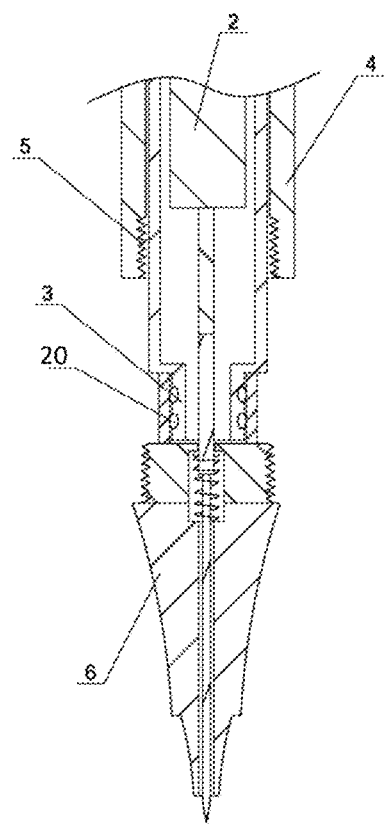
FIG. 47 is a structural schematic view of an operating rod connected to an injection needle where the case is omitted, according to an embodiment of the present disclosure.

As shown in FIGS. 46 and 47, the pushing member 10*a* includes a spring. A top of the spring abuts against the top wall of the annular limiting space, and a bottom of the spring abuts against the top wall of the limiting member.

In the present embodiment, the pushing member is the spring. The spring is constantly in a compressed state. Therefore, a restoring force of the spring constantly pushes the limiting member downwardly to push the limiting member and the case to move downward, such that the bottom wall of the limiting member abuts against the bottom wall of the annular limiting space. When the case needs to be moved upward, the operator may push the case upwardly to further compress the spring.

As shown in FIGS. 46 and 47, the limiting member is an annular protrusion and is arranged on the outer surface of the top end of the case.

A limiting ring 9 is arranged on the outer surface of the middle portion of the shell. The limiting ring has a lower inner wall, and an annular spacing is defined between the lower inner wall and the outer wall of the shell, and the top end of the case is received in the annular spacing.

The lower inner wall of the limiting ring defines an annular groove 10*b*. The annular limiting space is formed by the annular groove and the outer wall of the shell. The limiting member is arranged in the annular groove. The top end and the limiting member are inserted in the annular limiting space.

In the present embodiment, the limiting ring may be directly connected to the shell or connected to the shell through an adhesive. Alternatively, the limiting ring may be fixedly connected to the shell through bolts. The top end of the case is directly inserted between the limiting ring and the shell. In addition, the inner wall of the limit ring defines the annular groove, the annular limiting space is formed by the annular groove and the shell. The annular protrusion on the top end of the case is received in the annular groove. A height of the annular protrusion (the height refers to the thickness of the protrusion in the axial direction of the shell) is less than a height of the annular groove. In this way, the height of the annular groove is the maximum distance that the annular protrusion and the case can move up and down along the shell.

In some embodiments, the pushing member 10*a* may be two magnetic members. One of the two magnetic members is arranged on the top wall of the annular limiting space, and the other one of the two magnetic members is arranged on the top wall of the limiting member. The two magnetic members have a same polarity, and therefore, the two magnetic members repel from each other. When the case moves upward by a force, the limiting member approaches the top wall of the annular limiting space, the fastener 3 of the shell may be exposed, and the repelling force between the two magnetic members is increased, such that the top wall of the annular limiting space tends to push the case away from the top wall of the annular limiting space. When the force is released, the case is pushed away from the top wall of the annular limiting space, and the fastener 3 of the shell is received in the case 4.

Figure 48A:
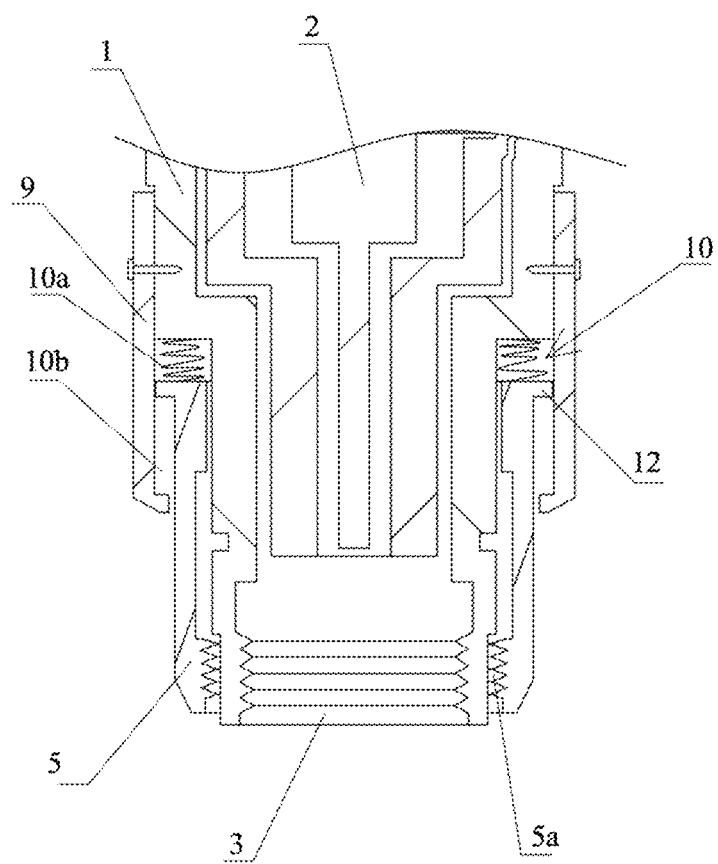
FIG. 48a is an enlarged view of a limiting ring in FIG. 46.
Figure 48B:
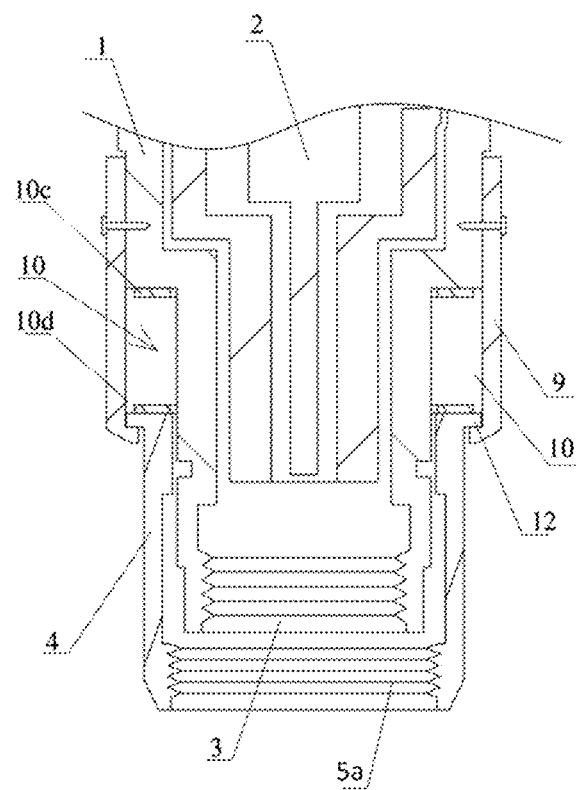
FIG. 48b is another enlarged view of a limiting ring in FIG. 46.

As shown in FIG. 48*b*, in the present embodiment, the pushing member includes a top magnetic ring 10*c* and a bottom magnetic ring 10*d*. The top magnetic ring 10*c* is arranged on the top surface of the annular limiting space, and the bottom magnetic ring 10*d* is arranged on the top surface of the limiting member. A magnetic pole on a bottom surface of the top magnetic ring 10*c* is the same as a magnetic pole on a top surface of the bottom magnetic ring 10*d*. In this way, a repelling force is constantly generated between the top magnetic ring 10*c* and the bottom magnetic ring 10*d*.

In the present embodiment, the magnetic rings having the same magnetic pole are arranged to face towards each other, the repulsive force therebetween pushes the case to move downward.

In some embodiments, when the annular limiting member is away from the top wall of the annular limiting space, a first magnetic repelling force is generated between the top magnetic ring and the bottom magnetic ring. When the annular limiting member is near the top wall of the annular limiting space, a second magnetic repelling force is generated between the top magnetic ring and the bottom magnetic ring. The second magnetic repelling force is larger than the first magnetic repelling force.

In order to allow the case to move and rotate smoothly and to prevent rigid friction between the case and the shell, lubricating oil may be coated between the case and the outer wall of the shell.

By applying the lubricating oil, the case may move and rotate more smoothly with respect to the shell, stucking may be reduced. In this way, the case is always pushed downward by the pushing member under normal circumstances, and the case receives and protects the fastener of the shell.

An adjustment member is arranged on a top of the shell (an end away from the end where the injection needle is protruded). The adjustment member is threaded to the top of the shell. When the adjustment member rotates, the driving mechanism is pushed to move downward or upward.

In the present embodiment, the driving mechanism includes a motor and a drive shaft. The motor pushes the drive shaft to move up and down. When the motor pushes the drive shaft to move downward, the injection needle is driven to move downward. When the motor drives the drive shaft to move upward, the injection needle is self-reset to move upward. That is, a top of the injection needle (for example, an end of the liquid guiding member away from the needle tooth) constantly contacts the drive shaft. Therefore, the driving mechanism drives the injection needle to move up and down reciprocally, achieving the tattooing. A power supply mechanism is connected to the adjustment member to supply power to the driving mechanism. The adjustment member is threaded to the operating rod. In this way, when the adjustment member and the operating rod are threaded and rotated relative to each other, the adjustment member drives the driving mechanism to move upward and downward. In this way, a length that the needle piercing portion of the injection needle protrudes out of the case of the operating rod is adjusted.

As shown in FIG. 47, at least one elastic seal 20 is arranged on an outer surface of a bottom of the first fastener, and the outer surface of the bottom of the first fastener defines at least one annular mounting slot. Each of the at least one elastic seal 14*a* is received in a corresponding one of the at least one annular mounting slot. The elastic seal is positioned by the annular mounting slot.

In the present embodiment, when the first fastener is fastened with the injection needle, the elastic seal is compressed and elastically deformed and applies a compression force to the injection needle and to increase a friction between the injection needle and the first fastener. In this way, an axial resistance opposite to a moving direction of the injection needle is generated, such that the injection needle is prevented from moving in the axial direction of the shell and prevented from being separated from the operating rod. In the present disclosure, more than 2 elastic seals are arranged and are spaced apart from each other. When mounting and positioning the injection needle, if only one elastic seal is arranged, the first fastener and the injection needle may shake with respect to each other. When two or more elastic seals are arranged, the two or more elastic seals stabilize the injection needle at two or more different positions, ensuring stability of the connection between the injection needle and the operating rod and ensuring stability of the tattoo device while being in use.

Figure 49:
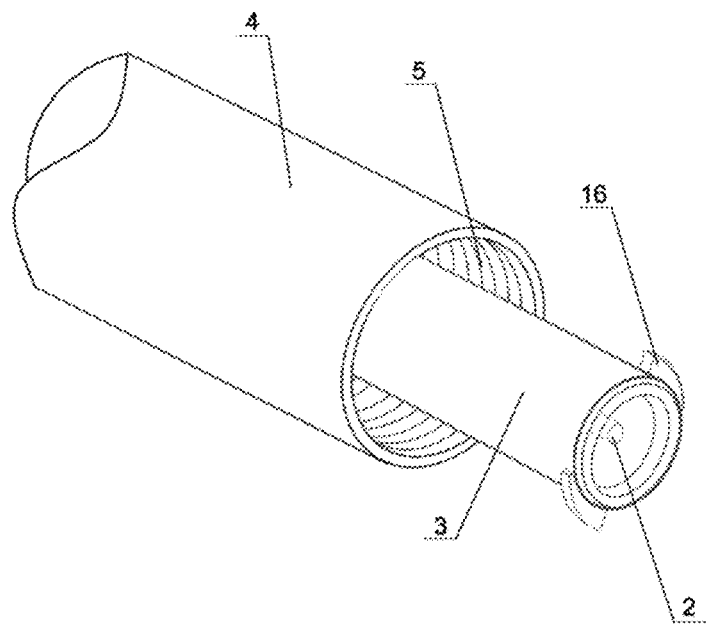
FIG. 49 is a perspective view of a first fastener according to an embodiment of the present disclosure.

As shown in FIG. 49, in the present embodiment, the outer surface of the bottom of the first fastener is arranged with two limiting snaps 16, and the two limiting snaps are located symmetrical to each other.

In the present embodiment, the injection needle defines two snap slots to be snapped with the two limiting snaps, forming a rotatable lock structure.

Figure 50:
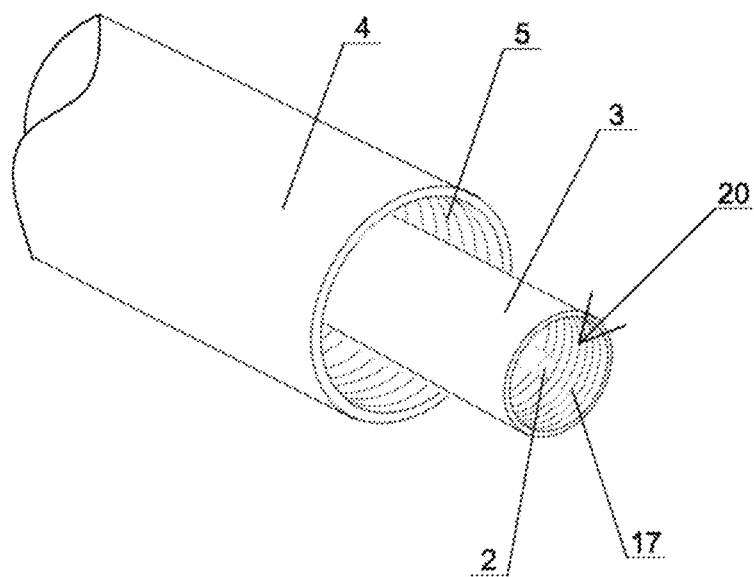
FIG. 50 is a perspective view of a first fastener according to another embodiment of the present disclosure.
Figure 51:
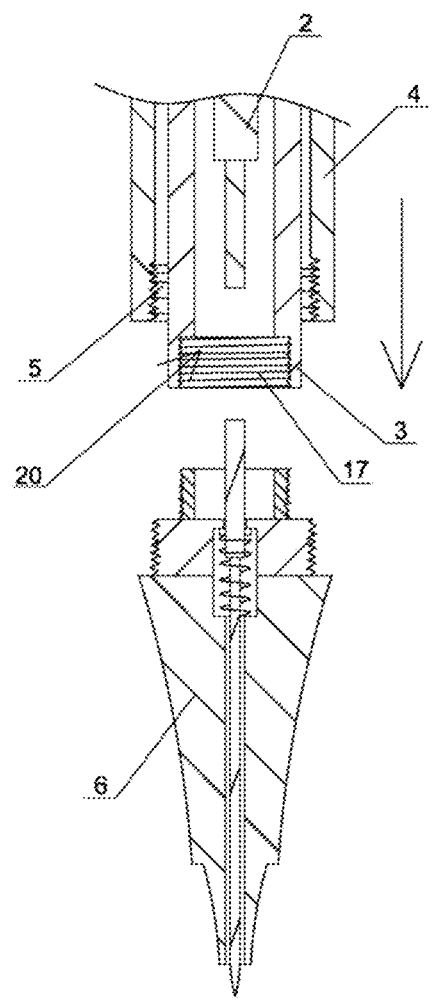
FIG. 51 is a structural schematic view of the operating rod connected to the injection needle according to an embodiment of the present disclosure.
Figure 52:
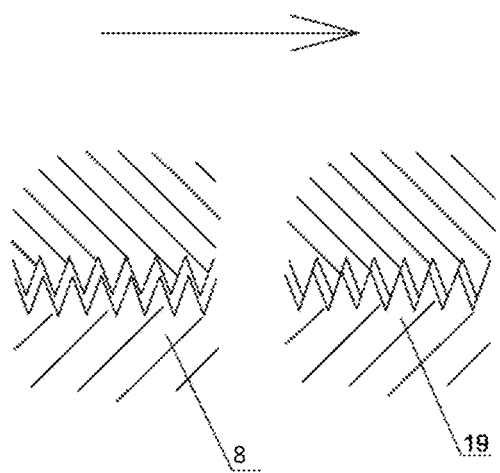
FIG. 52 is a structural schematic view of coarse threads and fine threads when the injection needle is loosened after the injection needle is fastened with the operating rod according to an embodiment of the present disclosure.

As shown in FIGS. 50 to 52, in the present embodiment, the bottom of the first fastener is arranged with bottom threads 17.

In the present embodiment, the first fastener and the injection needle are connected to each other by threading.

When the first fastener is threads (i.e., first threads) and the first inner fastener is inner threads (i.e., first inner threads), a helical direction of the first threads is opposite to a helical direction of the first inner threads. A pitch of the bottom threads is greater than a pitch of the first inner threads. The bottom threads may be coarse threads 8, and the first inner threads may be fine threads 19.

In the present embodiment, the first fastener may be the first threads, and the injection needle may be arranged with corresponding threads, such that the first fastener is fastened to the injection needle by threading the corresponding threads.

The coarse threads have a large rising angle. Since the coarse threads have the large rising angle and the large pitch, the number of threads is reduced for a certain threading distance. Therefore, for the coarse threads, the mounting accuracy is not highly required, and structures connected through the coarse threads can be easily connected with and detached apart from each other. However, the coarse threads have relatively weak anti-vibration performance, poor self-locking performance, and poor sealing performance, and therefore, the connection through the coarse threads may be loose easily. The fine threads have a small rising angle and a small pitch, and the number of threads is large for a certain threading distance. Therefore, a better sealing performance, a better anti-vibration performance, a better self-locking performance, and a better sealing performance can be achieved through the fine threads. The connection through the fine threads may not be loose easily, however, the mounting needs to be highly accurate.

In the present embodiment, when the operating rod is connected to the injection needle. The first fastener is inserted into the injection needle (the injection needle is arranged with the coarse threads corresponding to the first fastener and the fine threads corresponding to the case). The injection needle is quickly aligned and connected to the operating rod through the coarse threads, such that the primary fastening is achieved. The case and the injection needle are connected to each other through the fine threads. The primary fastening guides and positions the case and the injection needle, such that the connection and alignment between the case and the injection needle can be achieved quickly. Therefore, configuration of both the coarse threads and the fine threads ensures the strength and stability of the connection and enables the connection to be achieved smoothly and conveniently.

As shown in FIG. 52, in the present embodiment, after a long-time and high-frequency vibration, the coarse threads may be loose firstly. That is, the injection needle moves downward relative to the operating rod, and that is, the coarse threads of the injection needle moves downward relative to the coarse threads of the first fastener of the shell. That is, the connection therebetween is loosened. However, the rising angle of the coarse threads is larger than that of the fine threads. When a same external force is applied, a loosening extent of the coarse threads is larger than that of the fine threads. During the loosening, a gap between the fine threads of the case and the fine threads of the injection needle is gradually reduced, and the fine threads of the case and the fine threads of the injection needle may be compressed against each other. As the compression force is gradually increased, a contact area and a friction between the fine threads of the case and the fine threads of the injection needle increase. In this way, the fastening between the case and the injection needle is increased. That is, the fastening between the operating rod and the injection needle is increased. Therefore, in the present embodiment, the helical direction of the bottom threads is opposite to the helical direction of the first inner threads, such that reverse forces are applied to improve the fastening effect. Furthermore, both the fine threads and the coarse threads are arranged to restrict each other to further improve the fastening effect. In this way, stability, firmness and safety of the tattooing is improved, preventing the injection needle from falling off from the operating rod.

In the present embodiment, the bottom of the first fastener defines a cavity 20, a bottom of the driving mechanism is inserted into the cavity. The threads at the bottom are inner threads that are arranged on an inner wall of the cavity.

Figure 53:
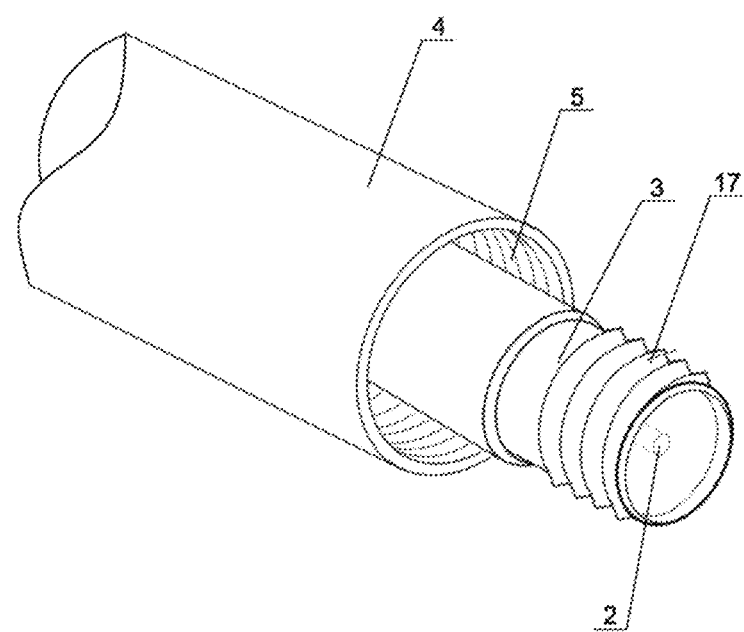
FIG. 53 is a perspective view of the first fastener according to another embodiment of the present disclosure.

As shown in FIG. 53, the threads 17 at the bottom of the first fastener are outer threads that are arranged on an outer wall of the first fastener.

In another embodiment, an elastic clamp may be detachably disposed between the case and the first fastener. An outer wall of a top of the elastic clamp is arranged with outer connection threads. The elastic clamp takes the outer connection threads to connected to the first inner threads of the case. A gap is defined between the elastic clamp and the first fastener. When the case moves downward relative to the elastic clamp, the elastic clamp is pushed to have the bottom of the elastic clamp being closed. When the case moves upward relative to the elastic clamp, the elastic clamp is reset automatically, such that the bottom of the elastic clamp is opened.

The elastic clamp includes a connection portion and a plurality of elastic jaws arranged at a bottom of the connection portion. A deformation gap is defined between every two adjacent elastic jaws. The outer connection threads are disposed on a top outer surface of the connection portion. Each elastic jaw has an inclining and guiding surface, inclining towards the first fastener and towards the top of the first fastener. The bottom of the case abuts against the inclining and guiding surface. When the case moves downward relative to the elastic clamp, the bottom of the case compresses the inclining and guiding surface, pushing bottoms of the elastic jaws to move towards an axis of the elastic clamp, such that the elastic clamp is closed. When the case moves upward relative to the elastic clamp, the bottoms of the elastic jaws are reset automatically, such that the elastic clamp is opened.

In the above embodiments, the secondary fastening is achieved by the first inner threads at the bottom of the case being threaded with the threads on the injection needle. In some embodiments, the secondary fastening may be achieved by other means, such as by the elastic clamp.

Even when the outer surface of the injection needle is arranged with the outer threads that can be threaded with the first inner threads of the case, the elastic clamp can also clamp the injection needle properly.

When connecting the injection needle with the operating rod, the first fastener of the operating rod is connected to the injection needle firstly. Subsequently, when the case is fastening with the shell and is moving downward, the elastic clamp is driven to move downward. When the elastic clamp reaches a clamping position, the operator presses the elastic clamp (or, if the elastic clamp abuts against the injection needle and cannot further move down, there is no need for the operator to press the elastic clamp). In this way, the elastic clamp does not move as the case rotates or moves. The case continues to move downward, and at this moment, the case is threaded with the first inner threads through the outer connection threads. The case rotates and moves downward relative to the elastic clamp. Due to the inclining and guiding surface, the case pushes the bottom of the elastic jaws to be deformed inwardly, and that is, the elastic chucks are closed to clamp the injection needle to achieve the secondary fastening. When loosening the case, the case moves upward relative to the elastic clamp, and the elastic jaws are reset automatically, such that the elastic clamp is opened, and the secondary fastening is released.

In the present embodiment, the case drives the elastic clamp to be opened and closed to realize the secondary fastening. Even if the outer surface of the injection needle is smooth and is not arranged with any thread, the injection needle can still be locked and limited.

Moreover, the elastic clamp is detachably connected to the case. When the operating rod needs to be arranged to an injection needle of a previous version, i.e., the injection needle has only one fastener and does not have the outer fastener to be fastened with the first inner fastener of the case, the elastic clamp may be arranged to directly cover and clamp the injection needle. In this way, the injection needle of the previous version can also be fastened twice. Therefore, costs of replacing the injection needle is avoided.

The present disclosure provides an injection needle as shown in FIG. 54 to FIG. 64.

As shown in FIG. 54 to FIG. 57, an injection needle includes a needle body 1 and a needle piercing assembly 2 that is arranged inside the needle body and is capable of moving upwardly to be reset automatically. A top of the needle body is arranged with a first docking portion 3. A second docking portion 4 is connected to an end of the first docking portion 3. An outer diameter of the second docking portion is larger than an outer diameter of the top of the needle body. An outer surface of the second docking portion 5 is arranged with second outer threads. In the present disclosure, the second docking portion may be located on an outer surface of the first docking portion, or the second docking portion is connected to an upper end of the first docking portion, or the second docking portion is connected to a lower end of the first docking portion. In the present embodiment, the second docking portion is connected to the lower end of the first docking portion.

Figure 54:
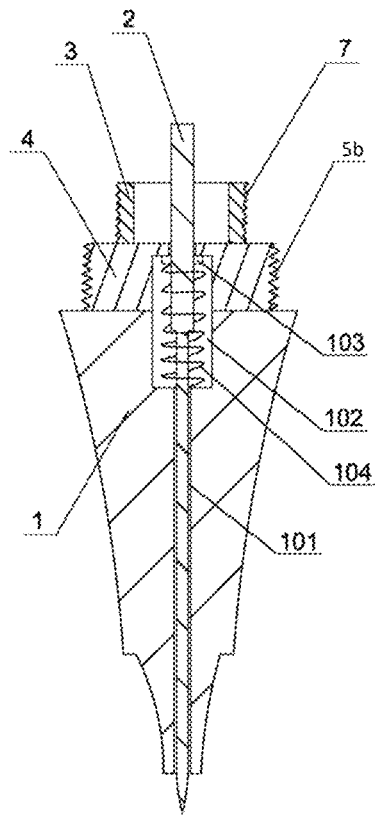
FIG. 54 is a structural schematic view of an injection needle according to an embodiment of the present disclosure.
Figure 56:
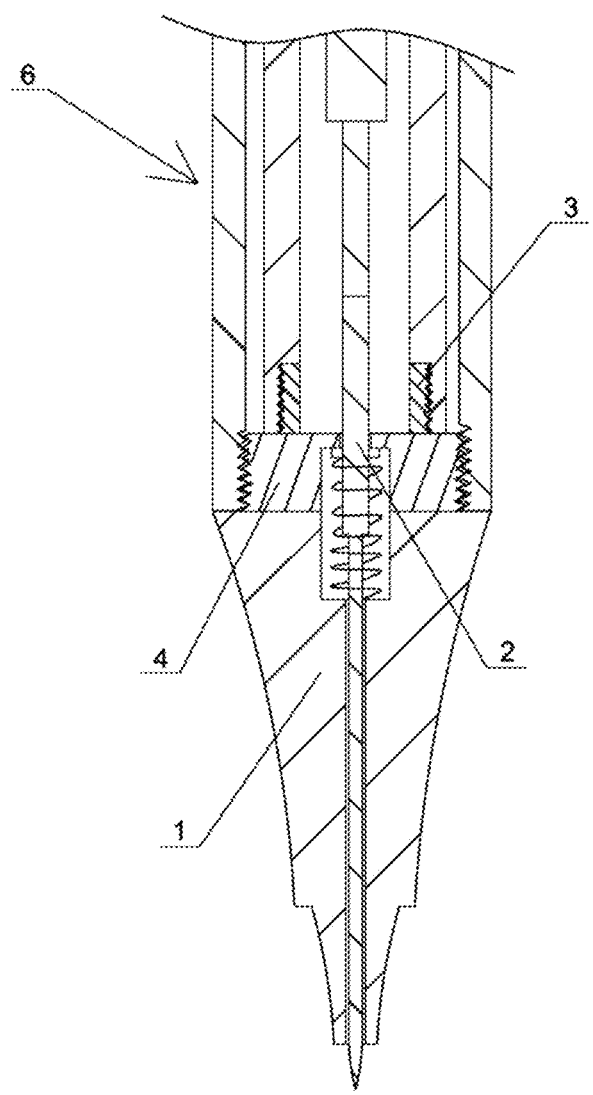
FIG. 56 is a structural schematic view of the injection needle being connected to an operating rod according to an embodiment of the present disclosure.

As shown in FIG. 54 and FIG. 56, a middle of the needle body defines a through hole 101. A middle of the needle piercing assembly is movably inserted into the through hole. The needle body further defines a reservation hole 102 located at a middle of the through hole 101. A diameter of the reservation hole is larger than a diameter of the through hole. An outer surface of a middle portion of the needle piercing assembly is arranged with a ring-shaped bump 103. The ring-shaped bump is received in the reservation hole. A spring 104 sleeves the middle portion of the needle piercing assembly. A bottom of the spring abuts against a bottom wall of the reservation hole, and a top of the spring abuts against a bottom surface of the ring-shaped bump. The spring pushes the ring-shaped bump and the needle piercing assembly to move towards to reset the needle piercing assembly. When a force is applied to push the needle piercing assembly to move downward, the spring is compressed. When the downward force is released, the spring is automatically reset and drives the needle piercing assembly to move upward to be reset automatically.

In the present embodiment, the needle body is connected with the operating rod 6. A driving mechanism is arranged inside the operating rod to drive the needle piercing assembly to extend out of the operating rod to perform the tattooing. In the art, when the operating rod is connected to the needle body, the connection is achieved through the first docking portion only, i.e., one fastening is achieved. However, for this configuration, one fastening may not provide the optimal connection. The tattoo device may vibrate at a high frequency for a long period of time for tattooing, and therefore, the only one fastening between the injection needle and the operating rod may be loose, causing the tattooing operation to have poor precision. Alternatively, during tattooing, the injection needle may be detached from the operating rod, which may hurt the user potentially. Therefore, in the present embodiment, after the needle body is connected to the operating rod by the first docking portion to achieve a primary fastening, the needle body may further take second outer threads of the second docking portion to connect to the operating rod to achieve a secondary fastening. That is, two fastenings are achieved between the injection needle and the operating rod. Even if one of the two fastenings is loosened, the other one of the two fastenings may prevent the connection therebetween from being loosened, stability and safety of the tattooing may be improved.

Figure 55:
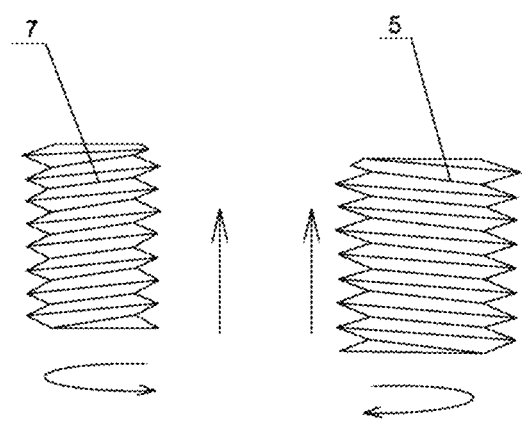
FIG. 55 is a structural schematic view of a helical direction the first connection threads and a helical direction of the second outer threads according to an embodiment of the present disclosure.

As shown in FIGS. 54 to 56, a top of the first docking portion is arranged with first connection threads 7.

In the present embodiment, the needle body takes the first docking portion to be threaded to the operating rod, such that the primary fastening therebetween is achieved.

A helical direction of the first connection threads is opposite to a helical direction of the second outer threads.

In the present embodiment, the helical direction of the first connection threads is opposite to the helical direction of the second outer threads. In an example, when the needle body is threaded to the operating rod by rotating in a clockwise direction to achieve the primary fastening, the needle body is threaded to the operating rod by rotating in an anti-clockwise direction to achieve the secondary fastening. That is, the two fastenings are achieved in two opposite threading directions. Therefore, regardless of which one of the two fastenings being loosened, the un-loosened one of the two fastenings has an increased locking strength, exhibiting an improved locking effect. In addition, due to the two fastenings having opposite fastening directions, connection strength and tightness between the needle body and the operating rod are improved, preventing the needle body and the operating rod from being loosened from each other, improving stability and safety of the tattooing process. Therefore, the colouring material (such as the ink) in the needle body entering the operating rod, caused by the needle body and the operating rod being loosened from each other, may be prevented, such that the operating rod is prevented from being contaminated.

A pitch of the first connection threads is greater than a pitch of the second outer threads.

The first connection threads are coarse threads 8, and the second outer threads are fine threads 9.

A rising angle of the coarse threads is larger. Since the coarse threads have a larger rising angle and a larger pitch, the number of threads for a certain threading distance is smaller. Therefore, for the coarse threads, the mounting accuracy is not highly required, and structures connected through the coarse threads can be easily connected with and detached apart from each other. However, the coarse threads have relatively weak anti-vibration performance, poor self-locking performance, and poor sealing performance, and therefore, the connection through the coarse threads may be loose easily. The fine threads have a small rising angle and a small pitch, and the number of threads is large for a certain threading distance. Therefore, a better sealing performance, a better anti-vibration performance, a better self-locking performance, and a better sealing performance can be achieved through the fine threads. The connection through the fine threads may not be loose easily, however, the mounting needs to be highly accurate.

Therefore, in the present embodiment, in order to enable the operating rod and the needle body to achieve the primary fastening more conveniently, the operating rod is also arranged with coarse threads corresponding to the coarse threads on the injection needle and fine threads corresponding to the fine threads on the injection needle. Threading between the coarse threads is the primary fastening. In this way, the coarse threads on the operating rod and the coarse threads on the injection needle may be aligned with and threaded with each other quickly, i.e., the primary fastening may be achieved quickly. The second outer threads (for the secondary fastening) are the fine threads. The primary fastening provides guidance to the fine threads to enable the fine threads on the injection needle and the fine threads on the operating rod to be aligned to each other, such that the secondary fastening may be achieved directly and quickly. If the fine threads on the injection needle is to be aligned to and threaded to the fine threads on the operating rod firstly, the alignment may not be performed easily, or slippage between the fine threads may occur.

Figure 57:
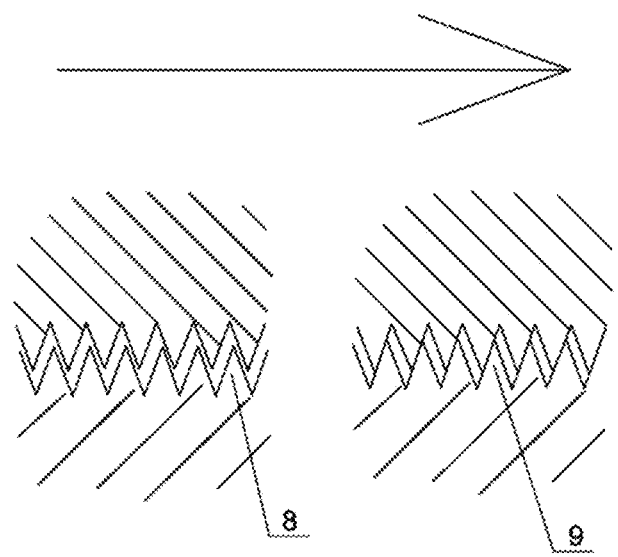
FIG. 57 is a structural schematic view of the coarse threads and the fine threads when the injection needle being loosened from the operating rod according to an embodiment of the present disclosure.

As shown in FIG. 57, after a long-time and high-frequency vibration, the coarse threads may be loose firstly. That is, the injection needle moves downward relative to the operating rod, and that is, the coarse threads of the injection needle moves downward relative to the coarse threads of the operating rod. That is, the connection therebetween is loosened. However, the rising angle of the coarse threads is larger than that of the fine threads. When a same external force is applied, a loosening extent of the coarse threads is larger than that of the fine threads. During the loosening, a gap between the fine threads of the operating rod and the fine threads of the injection needle is gradually reduced, and the fine threads of the operating rod and the fine threads of the injection needle may be compressed against each other. As the compression force is gradually increased, a contact area and a friction between the fine threads of the operating rod and the fine threads of the injection needle increase. In this way, the fastening force between the operating rod and the injection needle is increased, i.e., the fastening force of the secondary fastening is increased. Furthermore, both the fine threads and the coarse threads are arranged to restrict each other to further improve the fastening effect. In this way, stability, firmness and safety of the tattooing is improved, preventing the injection needle from falling off from the operating rod.

At the same time, in the present embodiment, the first docking portion has the primary fastening with the operating rod. In a case that the central axis of the needle body does not coincide with the central axis of the operating rod during the primary fastening, i.e., the needle body is deviated from the operating rod, threading between the fine threads may not be performed subsequently. Therefore, the operator is aware that the coarse threads on the needle body are not threaded to the coarse threads on the operating rod properly. The operator may disassemble and re-fasten the primary fastening. In this way, the needle piercing assembly is prevented from receiving forces unevenly, and the tattooing effect is ensured.

As shown in FIG. 54 to FIG. 56, the first connection threads are first outer threads, and the first outer threads are disposed on the outer surface of the top of the first docking portion. The second outer threads are disposed below the first outer threads and on the outer surface of the needle body. In the present embodiment, an outer diameter of the second outer threads is larger than an outer diameter of the first outer threads. In this way, the primary fastening and the secondary fastening do not interfere with each other.

In the present embodiment, the first docking portion is arranged with the outer threads, the operating rod is arranged with corresponding inner threads, such that the outer threads and the inner threads are threaded to each other correspondingly.

Figure 58:
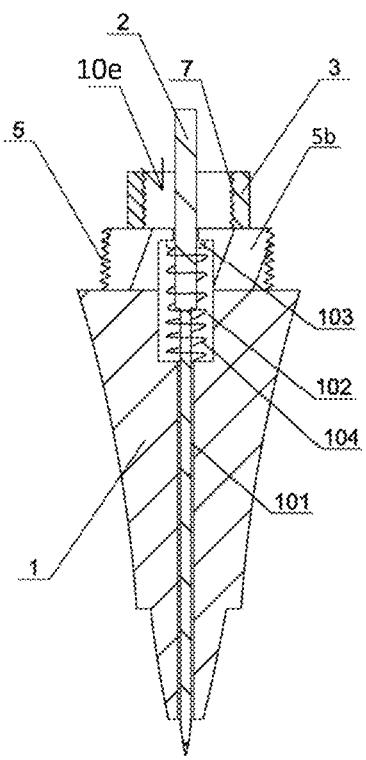
FIG. 58 is a structural schematic view of an injection needle according to another embodiment of the present disclosure.
Figure 59:
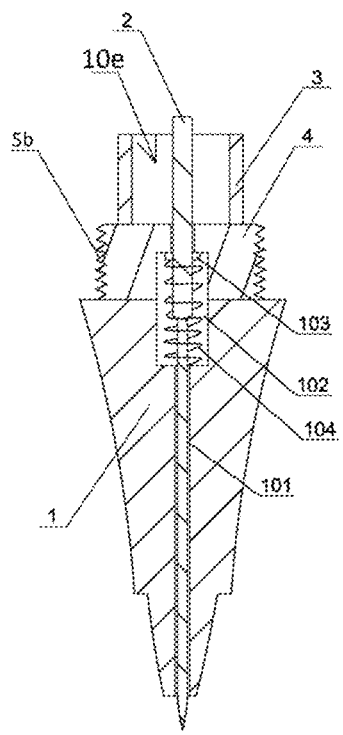
FIG. 59 is a structural schematic view of an injection needle according to still another embodiment of the present disclosure.

In another embodiment, as shown in FIG. 58, the first docking portion 3 defines a cavity 10e. The top of the needle piercing assembly is inserted in the cavity, or the top of the needle piercing assembly extends through the cavity to be located above the first docking portion. The first connection threads are first inner threads, and the first inner threads are disposed on an inner wall of the cavity. In the present embodiment, the first inner threads are disposed on an inner wall of a top portion of the cavity. The second outer threads are disposed below the first outer threads and located on the outer surface of the needle body.

In the present embodiment, the first connection threads are inner threads. In addition, the second docking portion is located below the first docking portion, and an outer diameter of the second docking portion is larger than an outer diameter of the first docking portion.

Figure 60:
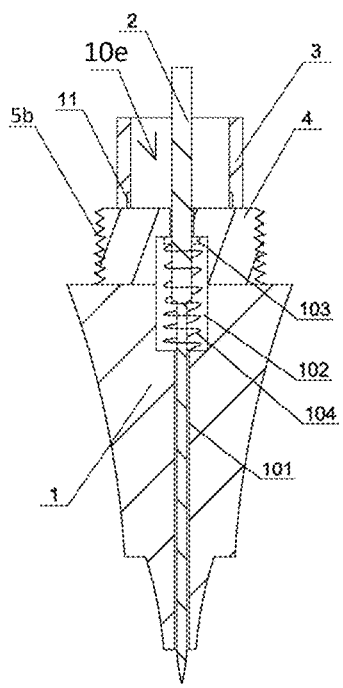
FIG. 60 is a structural schematic view of an injection needle according to still another embodiment of the present disclosure.

In another embodiment, as shown in FIG. 60, the injection needle includes the needle body 1 and the needle piercing assembly 2, which is arranged inside the needle body 1 and is capable of moving upwardly to be reset automatically. The top of the needle body is arranged with the first docking portion 3. The second docking portion 4 is connected to an end of the first docking portion, and the outer diameter of the second docking portion is larger than the outer diameter of the first docking portion 3. The second outer threads 5 are disposed on the outer surface of the second docking portion.

The first docking portion defines the cavity 10e. The top of the needle piercing assembly is inserted in the cavity, or the top of the needle piercing assembly extends through the cavity to be located above the first docking portion. The outer surface of the first docking portion and the inner wall of the cavity are smooth. The bottom of the operating rod has a first fastening portion is connected to the first docking portion in an insertion manner. The first fastening portion may be inserted into the cavity. A sealing ring is arranged on an outer surface of the first fastening portion to seal the first docking portion with the operating rod.

In the present embodiment, the second outer threads are threaded to the operating rod to achieve the secondary fastening, and the primary fastening is achieved in the insertion manner. That is, two fastenings are achieved.

Figure 61:
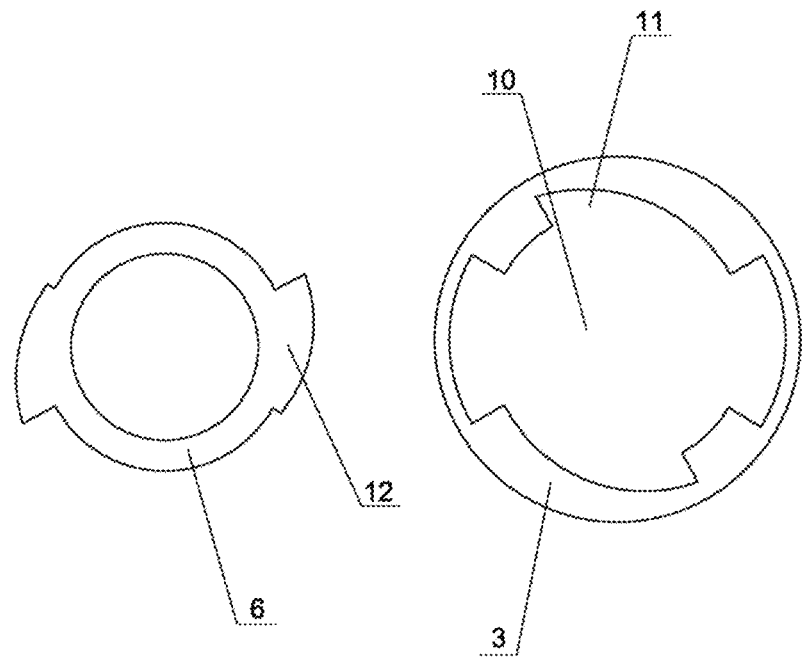
FIG. 61 is a structural schematic view of an end face of a first docking portion of the injection needle connected to the operating rod according to an embodiment of the present disclosure.
Figure 62:
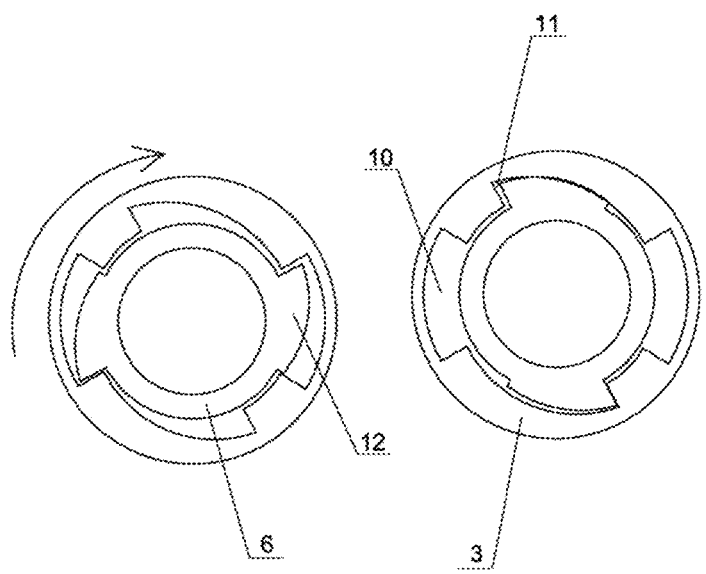
FIG. 62 is a process during which the end face of the first docking portion of the injection needle connected to the operating rod according to an embodiment of the present disclosure.

In another embodiment, as shown in FIG. 60 to FIG. 62, the injection needle includes the needle body 1 and the needle piercing assembly 2, which is arranged inside the needle body 1 and is capable of moving upwardly to be reset automatically. The top of the needle body is arranged with the first docking portion 3. The second docking portion 4 is connected to an end of the first docking portion, and the outer diameter of the second docking portion is larger than the outer diameter of the first docking portion 3. The second outer threads 5b are disposed on the outer surface of the second docking portion.

The first docking portion defines the cavity 10e. The top of the needle piercing assembly is inserted in the cavity, or the top of the needle piercing assembly extends through the cavity to be located above the first docking portion. The inner wall of the cavity defines two slots 11, and the two slots 11 are located symmetrical about the central axis of the cavity.

In the present embodiment, the second outer threads are threaded to the operating rod 6 to achieve the secondary fastening. A snap 12 is arranged on an outer surface of a bottom of the operating rod to be snap-fitted with the slots. The snap 12 is inserted and rotated in the slots to achieve the snap-fitting. Therefore, in the present embodiment, the two fastenings include one fastening in the threading manner and one fastening in the snap-fitting manner.

Figure 63:
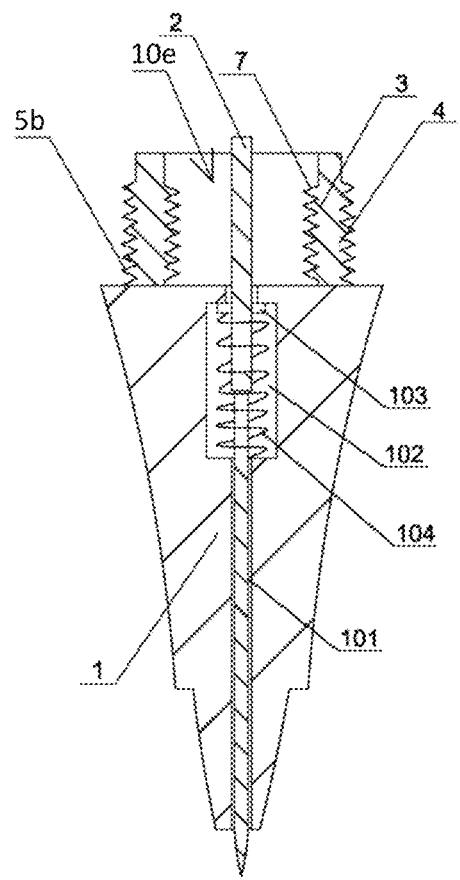
FIG. 63 is a structural schematic view of an injection needle according to still another embodiment of the present disclosure.

In another embodiment, as shown in FIG. 63, the first inner threads are disposed on the inner wall of the top portion of the cavity, and the second outer threads are disposed on an outside of the first inner threads. The second outer threads and the first inner threads are located on a same plane.

Figure 64:
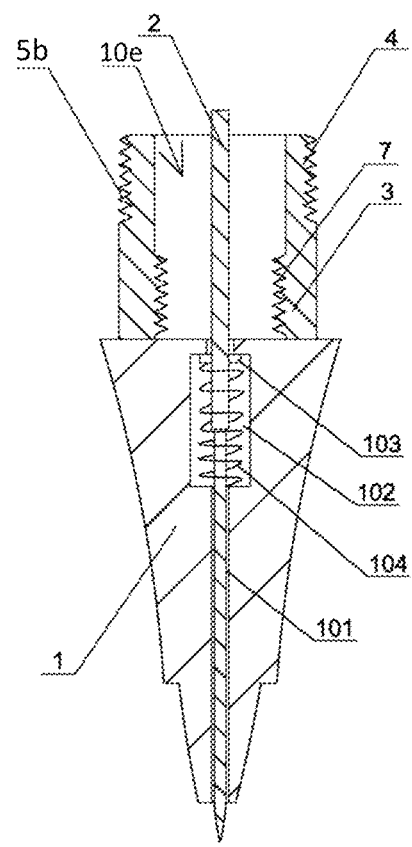
FIG. 64 is a structural schematic view of an injection needle according to still another embodiment of the present disclosure.

In another embodiment, as shown in FIG. 64, the first inner threads are disposed on the inner wall of a bottom portion of the cavity, and the second outer threads are disposed on the outer surface of a top portion of the cavity. That is, the second outer threads are located above the first inner threads.

The present disclosure provides a tattoo device as shown in FIG. 65 to FIG. 78.

As shown in FIG. 65 to FIG. 68, a tattoo device having two fastenings is provided and includes an operating rod 1 and an injection needle 2a connected to the operating rod. A top portion (an end away from the tip end) of the injection needle is arranged with a first docking portion 3. A bottom portion (a portion near the tip end of the injection needle) of the operating rod is arranged with a first fastener 4. The first fastener is detachably connected to the first docking portion. A second docking portion 5 is connected to a bottom end of the first docking portion, and an outer diameter of the second docking portion is larger than an outer diameter of the first docking portion. A second fastener 6 is disposed on an outer surface of the operating rod. The second fastener is detachably connected to the second docking portion. In the present embodiment, the first fastener, the second fastener, the first docking portion and the second docking portion are coaxially arranged with each other.

In the present embodiment, the tip end of the injection needle is denoted as the "bottom", and the operating rod is connected to the top portion of the injection needle.

In the present embodiment, when the operating rod is connected to the injection needle, the operating rod is quickly connected to the first docking portion of the injection needle through the first fastener, and subsequently, the operating rod is connected to the second docking portion through the second fastener. In this process, in a case that the central axis of the needle body does not coincide with the central axis of the operating rod after the first fastener is fastened to the first docking portion, i.e., the needle body is deviated from the operating rod, the second fastener may not be fastened to the second docking portion properly. Therefore, the operator is aware that the fastening between the first fastener and the first docking portion is not performed properly. The operator may disassemble and re-fasten the first fastener and the first docking portion to correct the deviation. In this way, the injection needle is prevented from receiving forces unevenly, and the tattooing effect is ensured. In the present embodiment, the first fastener is fastened to the first docking portion to achieve the primary fastening between the operating rod and the injection needle, and the second fastener is fastened to the second docking portion to achieve the secondary fastening between the operating rod and the injection needle. Fastening between the operating rod and the injection needle is improved, preventing the injection needle and the operating rod from being loosened from each other, improving stability and safety of the tattooing process. By configuring the two fastenings, in a case that one of the two fastenings is not effective, the other one of the two fastenings may be effective, improving the fastening between the operating rod and the injection needle, improving the sealing effect therebetween, and preventing the operating rod from being contaminated.

Figure 65:
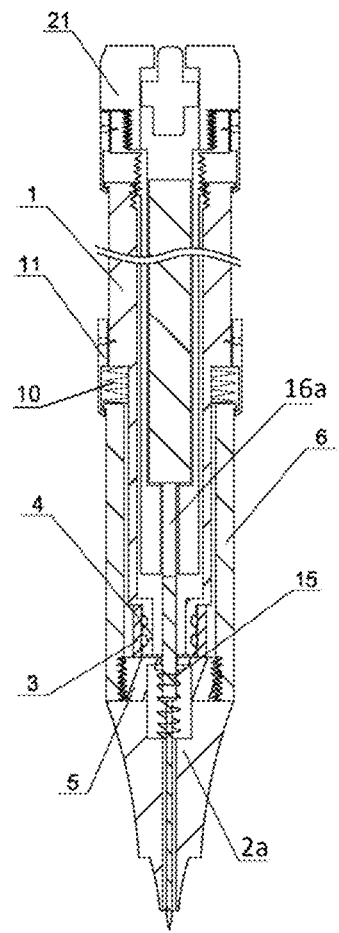
FIG. 65 is a structural schematic view of a tattoo device according to an embodiment of the present disclosure.
Figure 66:
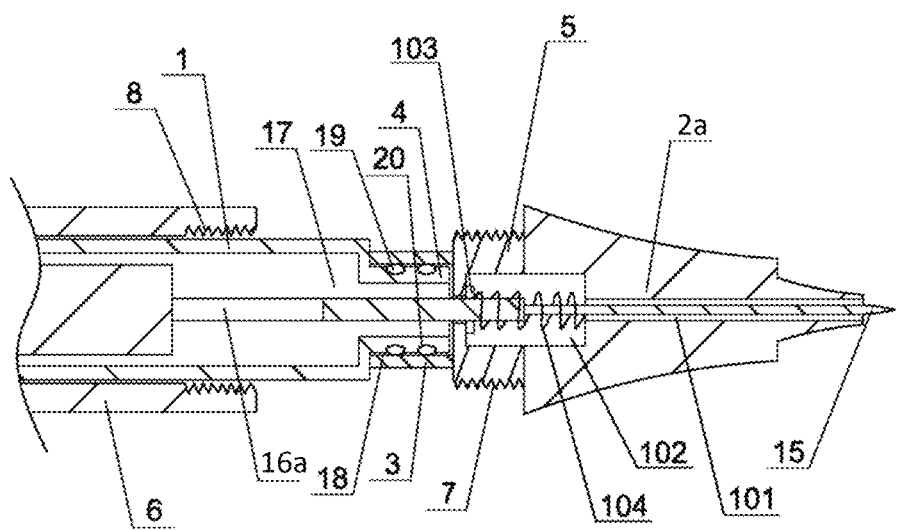
FIG. 66 is a structural schematic view of an operating rod connected to an injection needle according to an embodiment of the present disclosure.
Figure 67:
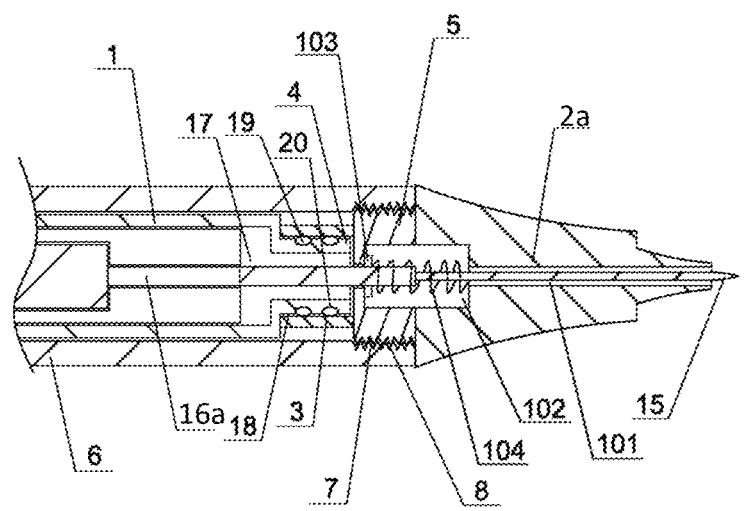
FIG. 67 is another structural schematic view of the operating rod connected to the injection needle according to an embodiment of the present disclosure.

As shown in FIG. 65 to FIG. 67, an inner wall of a bottom portion of the second fastener is arranged with inner threads 8. The second fastener is fastened to the second docking portion by threading the outer threads to the inner threads.

An outer diameter of the outer threads is smaller than an outer diameter of the injection needle. When the second fastener is connected with the second docking portion, a bottom end surface of the second fastener abuts against a top surface of the injection needle.

In the present embodiment, the fastening between the second fastener and the second docking portion is achieved by threads. Therefore, the secondary fastening is achieved quickly and conveniently. In addition, connection strength of threading is higher. When the second fastener is connected to the second docking portion, the second fastener abuts against the top surface of the injection needle. That is, the operating rod abuts against the injection needle, an anti-loosening force is provided, and a space for loosening is avoided, further preventing the operating rod and the injection needle from being loosened from each other, and improving the fastening effect.

Figure 68:
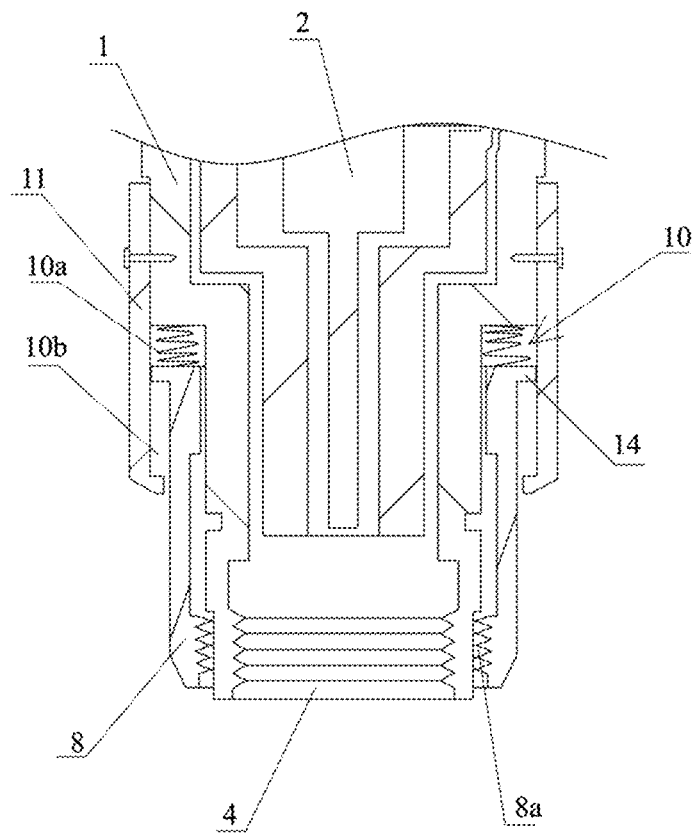
FIG. 68 is an enlarged view of the limiting ring shown in FIG. 65.

As shown in FIG. 65 and FIG. 68, when the second fastener is not connected to the second docking portion, the second fastener moves upwards along the operating rod. After the first fastener is connected to the first docking portion, the second fastener moves downwards. In the above process, the inner threads at the bottom portion of the second fastener is threaded to the outer threads of the second docking portion, such that the second fastener is fastened to the second docking portion. The operating rod is arranged with a limiting structure to limit the movement of the second fastener. In this way, after the second fastener is fastened to the second docking portion, the second fastener does not move relative to the injection needle or the operating rod, such that the second fastener, the injection needle, and the operating rod are fixed relative to each other, and the tattoo device may be structurally stable.

As shown in FIG. 65 and FIG. 68, a limiting ring 11 is arranged at the outer wall of the middle portion of the operating rod. A annular gap 10 is defined between the limiting ring and the outer wall of the middle portion of the operating rod. An inner wall of the limiting ring defines an annular slot 10b that faces directly towards the outer wall of the operating rod. An outer edge of a top end of the second fastener is arranged with an annular protrusion 14, which is movably received in the annular slot.

In the present embodiment, the annular protrusion on the outer edge of the top end of the second fastener is located in the annular slot of the limiting ring. In this way, when the second fastener is moving up and down, the annular protrusion of the second fastener is limited by the annular slot and the limiting ring, preventing the second fastener from being detached from the operating rod.

In the present embodiment, each of the limiting ring and the operating rod defines a screw hole. The limiting ring is fixed to the operating rod by arranging a bolt into the screw hole. Alternatively, the limiting ring may also be adhered to the operating rod, or connected to the operating rod by other means.

As shown in FIG. 65 to FIG. 67, the injection needle includes a needle piercing assembly 15 that can move upwards to be reset automatically. A driving assembly 16a may be arranged in the operating rod to drive the needle piercing assembly to extend downwardly out of the operating rod.

The driving assembly may include a motor and a drive shaft. The motor drives the drive shaft to move up and down. When the drive shaft is driven to move down, the needle piercing assembly is pushed to move downward. When the drive shaft is driven to move up, the needle piercing assembly moves upward automatically to be reset. In this way, a top portion of the needle piercing assembly constantly contacts a bottom end of the drive shaft. Therefore, the driving assembly drives the needle piercing assembly to move up and down reciprocally to perform the tattooing.

As shown in FIG. 65 to FIG. 67, a middle portion of the injection needle defines a mounting hole 101. A middle portion of the needle piercing assembly is movably inserted in the mounting hole. The middle portion of the injection needle further defines a reservation hole 102, located at a middle portion of the mounting hole 101. A diameter of the reservation hole is larger than a diameter of the mounting hole. An outer surface of a middle portion of the needle piercing assembly is arranged with an annular bump 103, received in the reservation hole. A spring 104 sleeves the middle portion of the needle piercing assembly. A bottom end of the spring abuts against a bottom wall of the reservation hole. A top end of the spring abuts against a bottom surface of the annular bump. The spring pushes the annular bump and the needle piercing assembly to move towards to be reset. When a downward force is applied to the needle piercing assembly, the spring is compressed, enabling the needle piercing assembly to move downward. When the downward force is released, the spring is automatically reset to push the needle piercing assembly to move upward to be reset.

As shown in FIG. 65 to FIG. 67, the first fastener defines a first cavity 17. A bottom end of the driving assembly is received in the first cavity. The first docking portion defines a through hole 18. A top end of the needle piercing assembly extends through the through hole to be received in the first cavity and connected to the driving assembly. A bottom end of the first fastener is inserted in the through hole. A top end of the first docking portion abuts against a bottom surface of the operating rod.

At least one elastic sealing member 19 is disposed between the first fastener and an inner wall of the through hole. An outer edge of a bottom portion of the first fastener defines at least one annular mounting slot 20. Each of the at least one elastic sealing member 19 is received in a respective one of the at least one annular mounting slot 20. An outer wall of each elastic sealing member abuts against the inner wall of the through hole. In the present embodiment, more than two elastic sealing members are arranged and are spaced apart from each other. In this way, when the injection needle is mounted and positioned, the more than two elastic sealing members stables the injection needle at more than two positions, preventing the injection needle from shaking relative to the first fastener, ensuring the connection therebetween to be stable and ensuring the tattoo device to be stable when being in use.

In the present embodiment, the first fastener is directly inserted into the first docking portion is fastened and sealed to the first docking portion by the elastic sealing member. In this way, the first fastener is in a tight fit connection with the first docking portion, and a primary fastening between the operating rod and injection needle is achieved. In the present embodiment, the first fastener and the first docking portion are connected to each other quickly in an insertion and tight-fitting manner.

In the present embodiment, when the first fastener is fastened with the first docking portion, the elastic sealing member is compressed and is elastically deformed, generating a compression force to the injection needle and increasing a friction for the injection needle. Therefore, an axial resistance force, opposite to a moving direction of the needle piercing assembly is generated, such that the injection needle along the axial direction is limited, preventing the injection needle from being detached from the operating rod.

In the present embodiment, the elastic sealing member serves as a sealing member and an elastic limiting member, furthermore, the elastic sealing member serves as an anti-slip member, preventing the injection needle from moving axially with respect to the operating rod. That is, the elastic sealing member limits the injection needle in the axial direction.

In the present embodiment, operations to be performed to connect the operating rod to the injection needle include the following.

In an operation 1, the operating rod approaches the injection needle, the first fastener is placed directly facing towards the first docking portion. The first fastener is inserted into the first docking portion, until the top end of the first docking portion abuts against the bottom surface of the operating rod. The first fastener is fastened to the first docking portion, such that the primary fastening is achieved.

In the operation 1, when the first fastener is inserted into the first docking portion, the first fastener and the first docking portion cooperatively compress the elastic sealing member, and the elastic sealing member is deformed. The compressive deformation optimally reduce any shaking between the first fastener and the first docking portion, preventing any axial movement between the first fastener and the first docking portion. That is, a resistance against the axial movement is increased, such that the injection needle is prevented from being detached from the operating rod.

In an operation 2, the operator rotates the second fastener to move the second fastener spirally downward. The bottom portion of the second fastener is fastened to the second docking portion by fastening the inner threads to the outer threads, until the second fastener contacts the top end of the injection needle. A threading force generated by the threading drives the operating rod to approach the injection needle, such that it is even more difficult for the injection needle to be separated from the operating rod, and the secondary fastening is achieved.

In the present embodiment, the elastic sealing member provides a first limitation to the axial movement between the operating rod and the injection needle. Furthermore, the threading force provides a second limitation to the axial movement between the operating rod and the injection needle. In this way, the injection needle is prevented from being loosened from the operating rod during the tattooing process, ensuring stability and safety of the tattooing.

In the present embodiment, an adjustment member 21 is disposed at a top portion of the operating rod. The adjustment member is arranged with a power supply mechanism to supply power to the driving mechanism. The adjustment member is threaded to the operating rod. Therefore, when the adjustment member is rotated with respect to the operating handle to be threaded to the operating handle, the adjustment member drives the driving mechanism to move up or down to adjust a length that the needle piercing assembly protrudes out of the operating rod.

Figure 69:
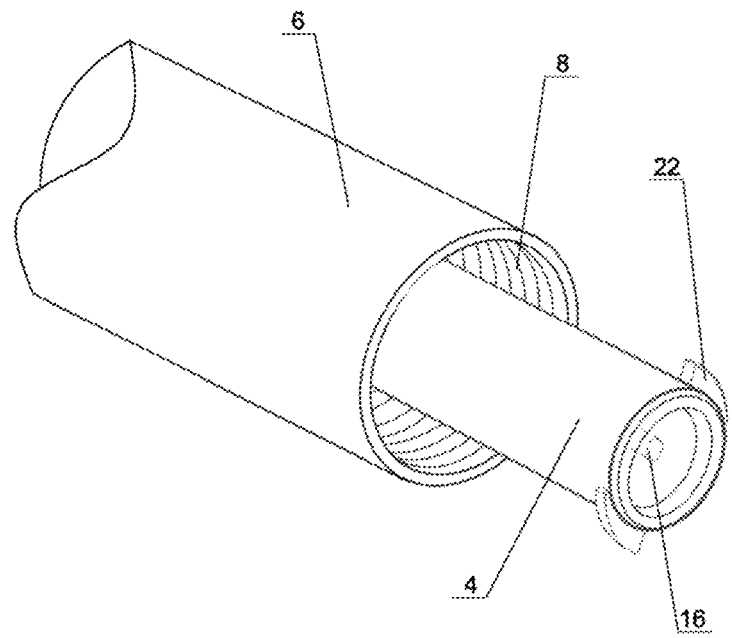
FIG. 69 is an enlarged view of an end of an operating rod according to another embodiment of the present disclosure.
Figure 70A:
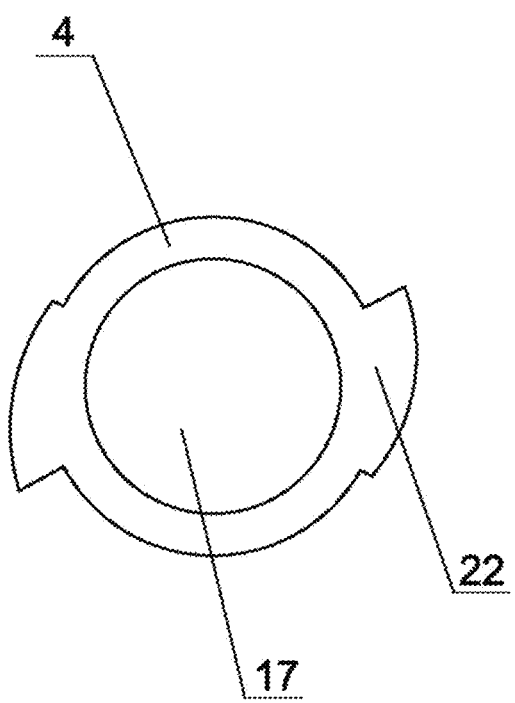
FIG. 70a is a structural schematic view of an end face of a first fastening portion according to another embodiment of the present disclosure.
Figure 70B:
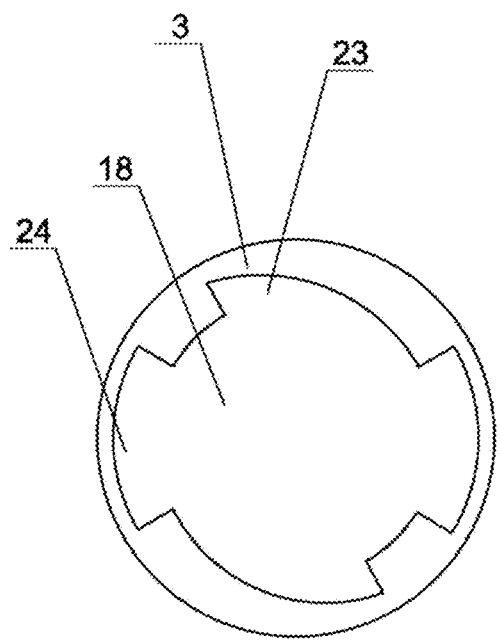
Figure 71:
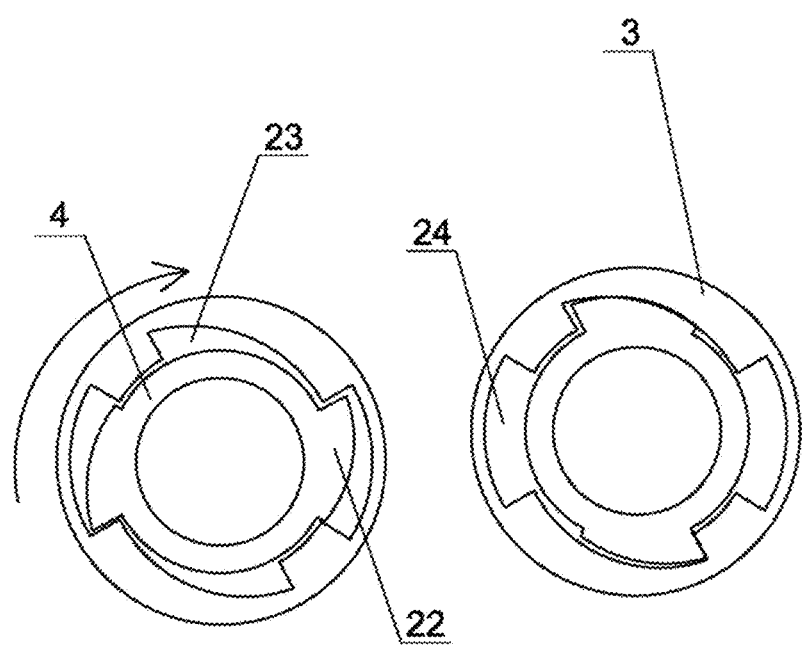
Figure 72:
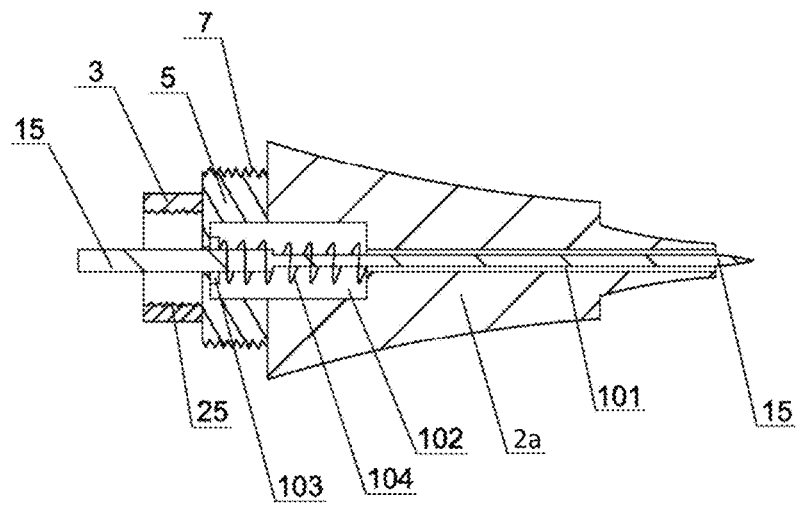
Figure 73:
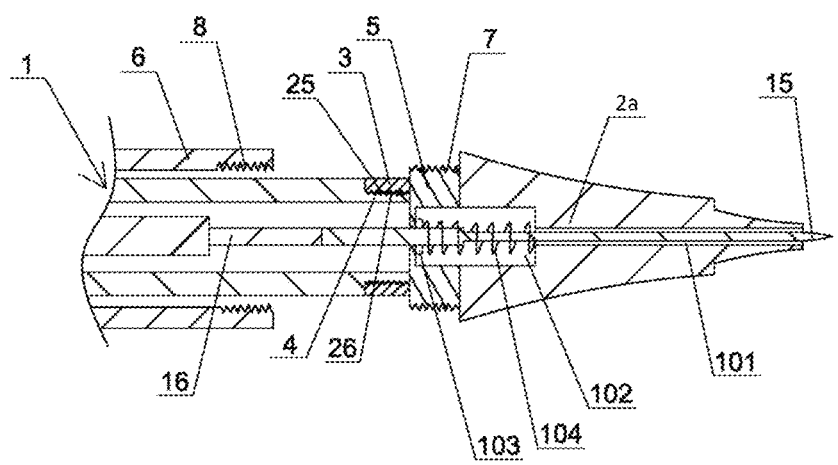
Figure 74:
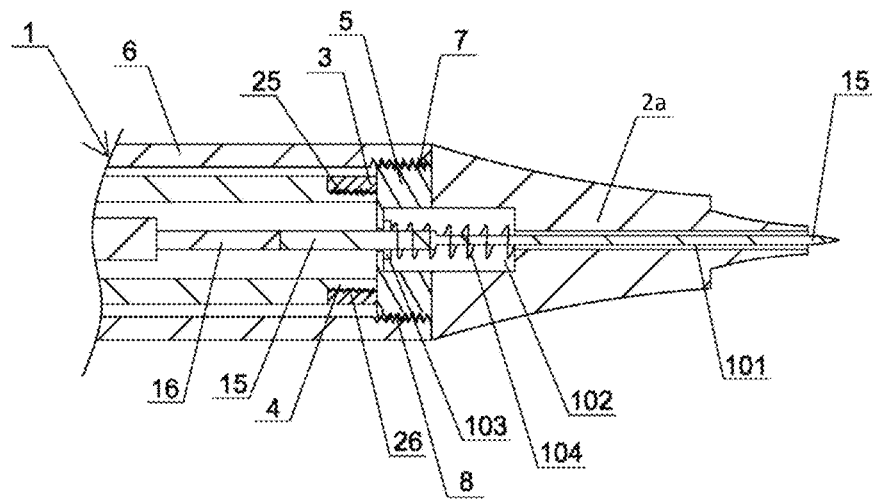
Figure 75:
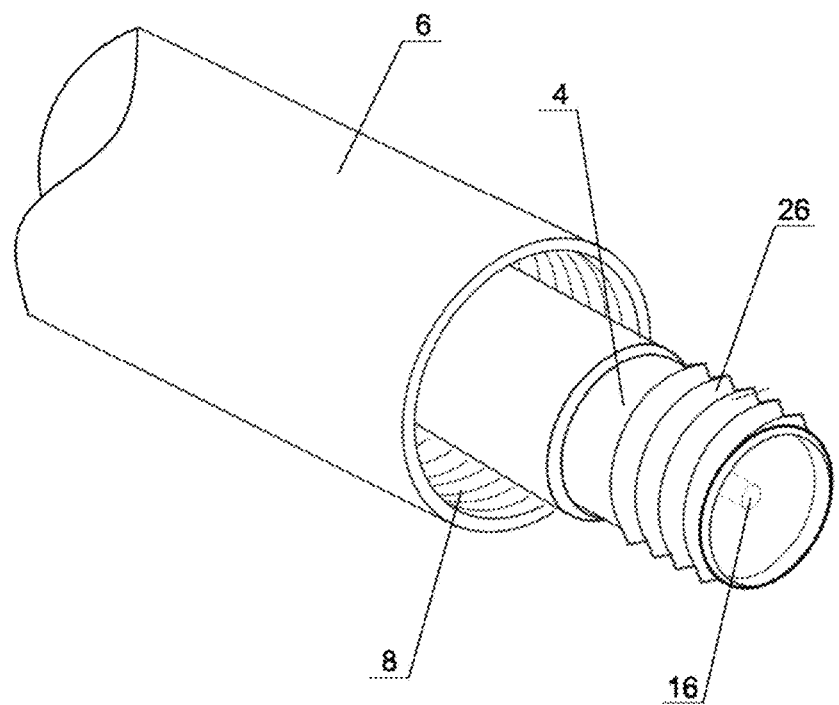

In another embodiment, as shown in FIG. 69 to FIG. 71, the first fastener and the first docking portion are connected to each other through a helical locking structure. The outer surface of the bottom portion of the first fastener defines two snap members 22. An inner wall of the through hole defines two snap slots 23, and the two snap slots 23 are located symmetrical to each other. The two snap members 22 are snapped to the two snap slots 23, and the two snap members 22 and the two snap slots 23 cooperatively form the helical locking structure.

Each snap member 22 has a curved outer surface, an edge of the curved outer surface is located near the outer surface of the first fastener, and the other edge of the curved outer surface is extending away from the outer surface of the first fastener. The inner wall of the through hole defines two notches 24 that are located symmetrical about the central axis of the through hole. Each notch is located between two adjacent snap slots. The snap portion is snapped to and is in tight fit with the snap slot correspondingly. When the first fastener is mounted with the second docking portion, the snap portion firstly passes through the notch to be inserted into the first docking portion. Subsequently, the first fastener is rotated to enable the snap portion to be snapped into the snap slot. In this way, the snap portion is snapped to and is in tight fit with the snap slot, and therefore, the first fastener can be tightly fastened to the second docking portion, and the assembling can be performed easily.

To summarize the above, in the present embodiment, the primary fastening is achieved through the helical locking structure.

In the present embodiment, an end of the snap portion is disposed near the outer surface of the first fastener, and the other end of the snap portion is disposed away from the outer surface of the first fastener. An end of a slot wall of the snap slot is connected to the inner wall of the curved snap portion, and the other end of the slot wall of the snap slot is connected to the inner wall of the curved snap portion. When the snap portion is snapped to the snap slot, the snap portion is inserted into the notch and is rotated to move downward and move to a side (i.e., move spirally or helically). In this process, a portion of the curved outer surface near the outer surface of the first fastener is gradually rotated to be received in the corresponding snap slot. The snap portion is further rotated, and due to the curved outer surface, the snap portion compresses the first docking portion. After the snap portion is completely received in the snap slot, the inner wall of the snap slot, which is also a curved surface, fits with the curved outer surface of the snap portion, and the snap portion is in tight fit with the snap slot. In this way, the snap slot limits rotation of the snap portion.

In the present embodiment, the second fastener and the second docking portion are connected to each other by threading, and the first fastener and the first docking portion are connected to each other by the helical locking structure. For the primary fastening, the snap portion is tightly snapped to the snap slot, enabling the first fastener to be tightly fastened with the first docking portion. The snap slot limits circumferential rotation of the snap portion. The tight fitting between the snap slot and the snap portion limits any axial movement between the snap slot and the snap portion. In this way, the injection needle is prevented from being loose from the operating rod, improving stability and safety during the tattooing.

In the present embodiment, when the helical locking between the first fastener and the first docking portion is achieved by rotating the first fastener in a clockwise direction, the second fastener needs to be rotated in an anti-clockwise direction to be fastened with the second docking portion. That is, a direction in which the first fastening is achieved is opposite to a direction in which the second fastening is achieved. Therefore, the two fastenings restrict each other, and the locking effect is better.

In another embodiment, as shown in FIG. 72 to FIG. 76, another tattoo device having two fastenings is provided. In the present embodiment, the first docking portion is arranged with top threads 25, and the bottom portion of the first fastener is arranged with bottom threads 26. The first docking portion is fastened to the first fastener by threading the top threads to the bottom threads.

In the present embodiment, the primary fastening is achieved by threading the top threads to the bottom threads.

Further, in the present embodiment, a threading direction between the top threads and the bottom threads is opposite to the threading direction between the inner threads and the outer threads. When the top threads and the bottom threads are left-handed threads, the inner threads and the outer threads are right-handed threads, or vice versa.

The top threads and the bottom threads are coarse threads, and the inner threads and the outer threads are fine threads. In this way, a pitch of the top threads and the bottom threads is greater than a pitch of the inner threads and the outer threads.

The coarse threads have a large rising angle. Since the coarse threads have the large rising angle and the large pitch, the number of threads is reduced for a certain threading distance. Therefore, for the coarse threads, the mounting accuracy is not highly required, and structures connected through the coarse threads can be easily connected with and detached apart from each other. However, the coarse threads have relatively weak anti-vibration performance, poor self-locking performance, and poor sealing performance, and therefore, the connection through the coarse threads may be loose easily. The fine threads have a small rising angle and a small pitch, and the number of threads is large for a certain threading distance. Therefore, a better sealing performance, a better anti-vibration performance, a better self-locking performance, and a better sealing performance can be achieved through the fine threads. The connection through the fine threads may not be loose easily, however, the mounting needs to be highly accurate.

Therefore, in the present embodiment, in order to enable an initial connection between the operating rod and the injection needle to be achieved conveniently and to improve an assembling efficiency, the first fastener and the first docking portion are connected to each other by coarse threads.

When the operating rod is connected to the injection needle, the first fastener is inserted into the first docking portion, and the first fastener is aligned with the first docking portion quickly through the coarse threads, such that the first fastener and the first docking portion can be quickly locked and positioned, achieving the primary fastening. Furthermore, connection between the second fastener and the second docking portion is achieved by the fine threads. The primary fastening enables the fine threads on the second fastener and the second docking portion to be aligned to each other, such that the fine threads on the second fastener may be threaded to the fine threads on the second docking portion quickly. If threading between the fine threads is performed directly, alignment between the fine threads may not be achieved easily, or slippage between the fine threads may occur. Therefore, the first fastener and the first docking portion are connected to each other by the coarse threads, and the second fastener and the second docking portion are connected to each other by the fine threads. Strength and stability of the connection are ensured, and mounting between the operating rod and the injection needle is performed smoothly and conveniently.

Figure 76:
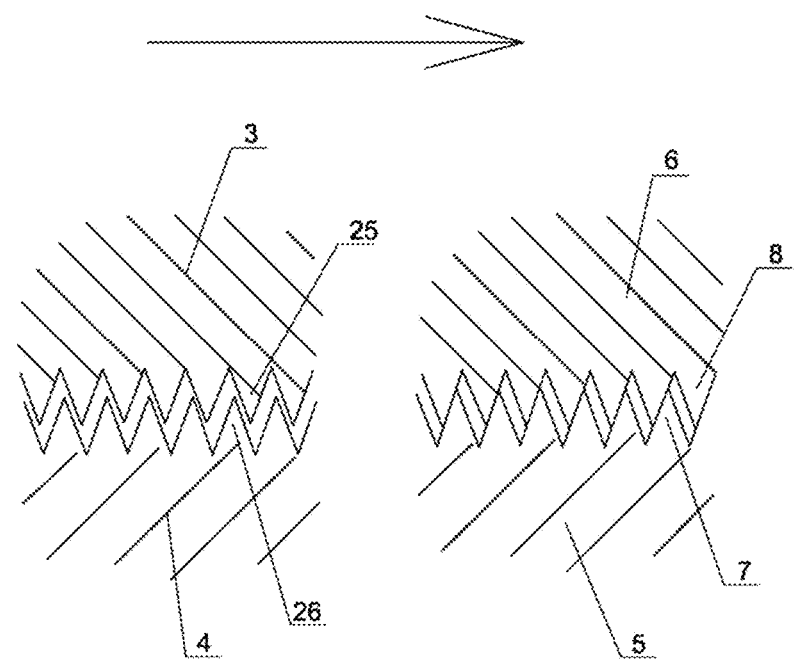
Figure 77:
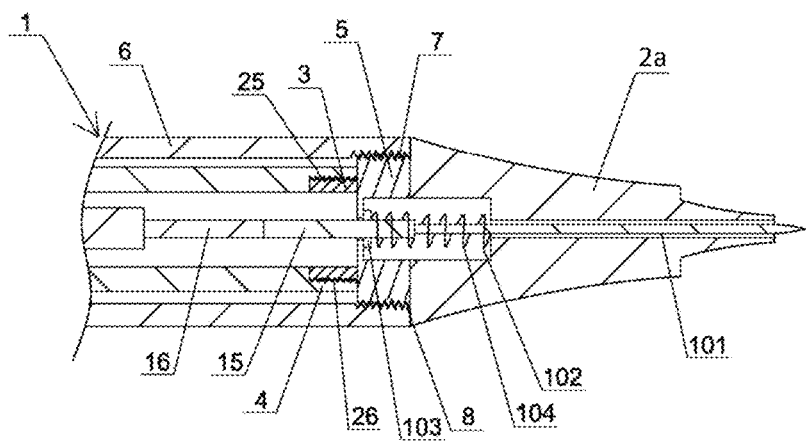

As shown in FIG. 76, in the present embodiment, after a long-time and high-frequency vibration, the coarse threads may be loose firstly. That is, the injection needle moves downward relative to the operating rod, and that is, the top threads moves downward relative to the bottom threads. That is, the connection therebetween is loosened. However, the rising angle of the coarse threads is larger than that of the fine threads. When a same external force is applied, a loosening extent of the coarse threads is larger than that of the fine threads. During the loosening, a gap between the outer threads and the inner threads is gradually reduced, and the outer threads and the inner threads may be compressed against each other. As the compression force is gradually increased, a contact area and a friction between the outer threads and the inner threads increase. In this way, the fastening force between the operating rod and the injection needle is increased, i.e., the fastening force of the secondary fastening is increased. In the present embodiment, the threading direction of the first fastening is opposite to the threading direction of the second fastening, such that fastening effect between the operating rod and the injection needle is improved. Furthermore, both the fine threads and the coarse threads are arranged to restrict each other to further improve the fastening effect. In this way, stability, firmness and safety of the tattooing is improved, preventing the injection needle from falling off from the operating rod.

In the present embodiment, the top threads are top inner threads, and the bottom threads are top outer threads. The top inner threads are disposed on the inner wall of the through hole.

Figure 78:
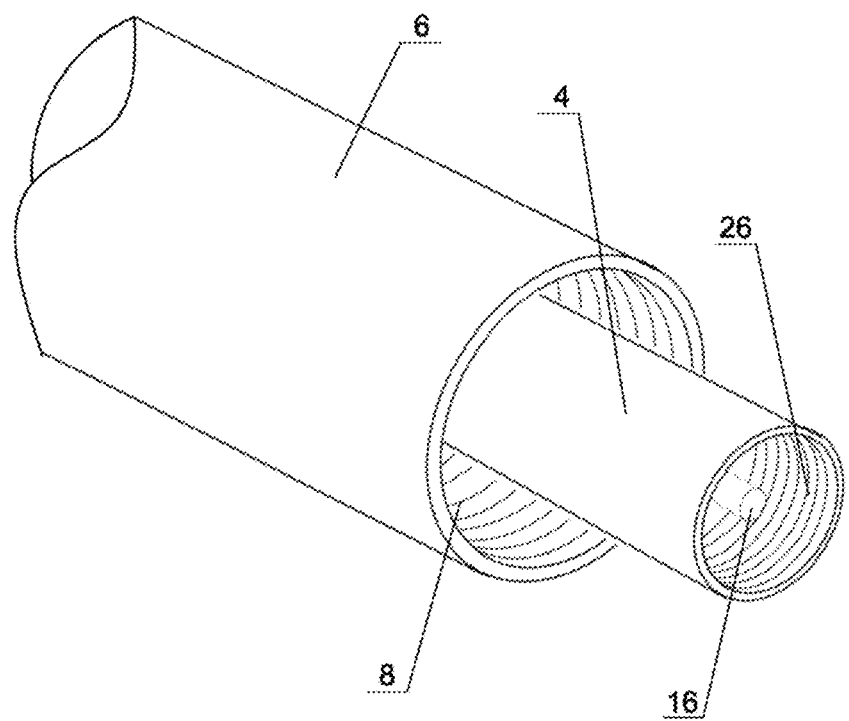

In another embodiment, as shown in FIG. 76 and FIG. 78, the top threads are top outer threads, and the bottom threads are top inner thread.

In the description of the present disclosure, the terms "an embodiment", "some embodiments", "examples", "specific examples", or "some examples" mean that specific features, structures, materials or characteristics described in one embodiment or one example are included in at least one embodiments or examples of the present disclosure. In the present specification, exemplary expressions of the above terms may not be directed to the same embodiment or the same example. Moreover, the specific features, structures, materials, or characteristics described may be combined in any one or more embodiments or examples in a suitable manner. In addition, any ordinary skilled person in the art may join and combine different embodiments or examples described in the present specification.

Although embodiments of the present disclosure have been shown and described above, it is to be understood that the above embodiments are exemplary and are not to be interpreted as a limitation of the present disclosure. Any ordinary skilled person in the art may perform changes, modifications and variations on the above embodiments within the scope of the present disclosure.

What is claimed is:

1. An operating rod for a tattoo device, the operating rod comprising:
    a drive mechanism, configured to drive an injection needle assembly of the tattoo device to move;
    a first rod body, having a receiving cavity and a first fastening portion, wherein the receiving cavity is configured to receive the drive mechanism, and the first fastening portion is configured to be detachably fastened with the injection needle assembly; and
    a second rod body, connected to at least part of the first rod body in a sleeved manner and configured with a second fastening portion, wherein the second fastening portion is configured to detachably connect to the injection needle assembly;
    wherein, during tattooing, the first fastening portion is configured to be fixedly fastened with a first portion of the injection needle assembly, and the second fastening portion is configured to be fixedly fastened with a second portion of the injection needle assembly, the second portion is different from the first portion; and
    during tattooing, both the first rod body and the second rod body have displacement with respect to a needle rod of the injection needle assembly.

2. The operating rod according to claim 1, wherein the first rod body and the second rod body are movably connected to each other in the sleeved manner, the second rod body is configured to reciprocately move relative to the first rod body in an extending direction of the first rod body;
    when the first rod body and the second rod body are moved to be connected to each other at a first position, the first fastening portion is received inside the second rod body; and
    when the first rod body and the second rod body are moved to be connected to each other at a second position, the first fastening portion extends out of the second rod body.

3. The operating rod according to claim 2, further comprising a resetting member, wherein,
    the resetting member is disposed between the first rod body and the second rod body; and
    when the first rod body and the second rod body are moved to be connected to each other at the second position, the resetting member is configured to drive the first rod body and the second rod body to move relative to each other to reset the first rod body and the second rod body to the first position.

4. The operating rod according to claim 3, wherein, a portion of an outer surface of the first rod body is recessed towards the receiving cavity, and the second rod body sleeves the recessed portion of the outer surface of the first rod body; and
    the resetting member is disposed between an end portion of the second rod body and the first rod body.

5. The operating rod according to claim 4, further comprising a limiting member, wherein the limiting member comprises:
    a connecting segment, fixedly connected to an un-recessed portion of the outer surface of the first rod body; and
    a limiting segment, extending in the extending direction of the first rod body towards the recessed portion of the outer surface of the first rod body, wherein a limiting space is defined between the limiting segment and the recessed portion of the outer surface of the first rod body;
    wherein, the resetting member and the end portion of the second rod body are received in the limiting space, the limiting space is configured to limit a distance that the end portion of the second rod body is capable of moving along the first rod body.

6. The operating rod according to claim 5, wherein, a protrusion is protruding from an outer surface of the end portion of the second rod body away from the second rod body;
    the limiting segment is arranged with a snap hook, the protrusion and the snap hook cooperatively limit the distance that the end portion of the second rod body is capable of moving along the first rod body.

7. The operating rod according to claim 6, wherein,
    when the first rod body and the second rod body are connected to each other at the first position, the protrusion abuts against the snap hook; and
    when the first rod body and the second rod body are connected to each other at the second position, the protrusion is spaced apart from the snap hook.

8. The operating rod according to claim 3, wherein,
    the resetting member is a resilient resetting member;
    when the first rod body and the second rod body are connected to each other at the first position, the resilient resetting member is not compressed or is compressed to have a first deformation amount;
    when the first rod body and the second rod body are connected to each other at the second position, the resilient resetting member is compressed to have a second deformation amount; and
    the second deformation amount is larger than the first deformation amount.

9. The operating rod according to claim 3, wherein,
    the resetting member is a magnetic resetting member and comprises a first magnetic member arranged on the first rod body and a second magnetic member arranged on the second rod body;
    the first magnetic member and the second magnetic member have a same polarity;
    when the first rod body and the second rod body are connected to each other at the first position, a first distance is between the first magnetic member and the second magnetic member, and a first magnetic repelling force is generated between the first magnetic member and the second magnetic member;

when the first rod body and the second rod body are connected to each other at the second position, a second distance is between the first magnetic member and the second magnetic member, and a second magnetic repelling force is generated between the first magnetic member and the second magnetic member;

the second distance is less than the first distance, and the second magnetic repelling force is larger than the first magnetic repelling force.

10. The operating rod according to claim 1, wherein, the first fastening portion comprises a resilient seal configured to resiliently abut against the injection needle to fix the first fastening portion to the injection needle; and the second fastening portion is second fastening threads configured to be threaded with the injection needle.

11. The operating rod according to claim 10, wherein, the resilient seal comprises at least two resilient members, the at least two resilient members are spaced apart from each other and are distributed in the extending direction of the first rod body, the at least two resilient members are configured to resiliently abut against at least two positions of the injection needle.

12. The operating rod according to claim 1, wherein, the first fastening portion comprises a snap portion configured to snap with the injection needle to secure the injection need;

the second fastening portion is second fastening threads configured to be threaded with the injection needle; and the snap portion is configured to rotationally snap with the injection needle.

13. The operating rod according to claim 12, wherein the snap portion comprises at least two snap members and are located symmetrically with respect to a central axis of the first fastening portion.

14. The operating rod according to claim 1, wherein the receiving cavity extends through the first fastening portion, and the drive mechanism is at least partially inserted into the receiving cavity in the first fastening portion to be connected to the injection needle assembly.

15. An operating rod for a tattoo device according to claim 1, wherein, the operating rod comprises:

a drive mechanism, configured to drive an injection needle assembly of the tattoo device to move;

a first rod body, having a receiving cavity and a first fastening portion, wherein the receiving cavity is configured to receive the drive mechanism, and the first fastening portion is configured to be fastened with the injection needle assembly; and a second rod body, connected to at least part of the first rod body in a sleeved manner and configured with a second fastening portion, wherein the second fastening portion is configured to connect to the injection needle assembly;

the first fastening portion is first fastening threads configured to be threaded with the injection needle assembly;

the second fastening portion is second fastening threads configured to be threaded to the injection needle assembly;

the first fastening portion and the second fastening portion are threaded to different portions of the injection needle assembly.

16. The operating rod according to claim 15, wherein, a threading direction of the first fastening threads is opposite to a threading direction of the second fastening threads.

17. The operating rod according to claim 16, wherein a pitch of the first fastening threads is larger than a pitch of the second fastening threads.

18. A tattoo device, comprising:

an operating rod; and an injection needle assembly, wherein the operating rod comprises:

a drive mechanism, configured to drive the injection needle assembly to move;

a first rod body, having a receiving cavity and a first fastening portion, wherein the receiving cavity is configured to receive the drive mechanism, and the first fastening portion is fastened with the injection needle assembly; and a second rod body, connected to at least part of the first rod body in a sleeved manner and configured with a second fastening portion, wherein the second fastening portion is fastened to the injection needle assembly;

wherein the injection needle assembly is at least partially received in the operating rod and connected to the drive mechanism, wherein the drive mechanism is configured to drive the injection needle assembly to reciprocately extend out of or to be received in the operating rod;

wherein the injection needle assembly comprises:

a first docking portion, fastened with the first fastening portion; and a second docking portion, fastened with the second fastening portion, wherein, an outer diameter of the second docking portion is larger than an outer diameter of the first docking portion.

19. The tattoo device according to claim 18, wherein, the injection needle assembly further comprises:

a needle piercing portion, comprising at least one needle tooth and a substrate, wherein, the at least one needle tooth is fixedly arranged on a portion of a side surface of the substrate; the remaining portion of the side surface of the substrate is configured to abut against skin when the at least one needle tooth pierces into the skin.

20. The tattoo device according to claim 19, wherein, the injection needle assembly further comprises a liquid guiding member configured to guide liquid to the at least one needle tooth; the needle piercing portion is arranged at an end of the liquid guiding member; an other side surface of the substrate is fixed to the liquid guiding member; an extending direction of the liquid guiding member is substantially parallel to a central axis of each needle tooth, the central axis of each needle tooth is perpendicular to the side surface of the substrate.

* * * * *